US010751313B2

(12) United States Patent
Hoffman et al.

(10) Patent No.: US 10,751,313 B2
(45) Date of Patent: *Aug. 25, 2020

(54) COMPOSITIONS AND METHODS FOR TREATING AUTISM

(71) Applicant: HOFFMAN TECHNOLOGIES LLC

(72) Inventors: Steven Hoffman, Mahwah, NJ (US); John Rothman, Lebanon, NJ (US)

(73) Assignee: Yamo Pharmaceuticals LLC, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/040,393

(22) Filed: Jul. 19, 2018

(65) Prior Publication Data

US 2019/0015364 A1 Jan. 17, 2019

Related U.S. Application Data

(63) Continuation-in-part of application No. 15/695,327, filed on Sep. 5, 2017, now Pat. No. 10,085,959, which is a continuation of application No. 15/138,733, filed on Apr. 26, 2016, now Pat. No. 9,757,348, which is a continuation of application No. 14/520,116, filed on Oct. 21, 2014, now Pat. No. 9,326,962, which is a continuation-in-part of application No. 14/062,165, filed on Oct. 24, 2013, now abandoned.

(60) Provisional application No. 61/894,261, filed on Oct. 22, 2013.

(51) Int. Cl.
A61K 31/198 (2006.01)
A61K 9/00 (2006.01)
A61K 31/19 (2006.01)
A61K 31/4166 (2006.01)
A61K 31/55 (2006.01)
A61P 25/00 (2006.01)
A61K 45/06 (2006.01)

(52) U.S. Cl.
CPC .......... *A61K 31/198* (2013.01); *A61K 9/0019* (2013.01); *A61K 9/0053* (2013.01); *A61K 31/19* (2013.01); *A61K 31/4166* (2013.01); *A61K 31/55* (2013.01); *A61P 25/00* (2018.01); *A61K 45/06* (2013.01); *A61K 2300/00* (2013.01)

(58) Field of Classification Search
CPC .................................................. A61K 31/198
See application file for complete search history.

(56) References Cited

U.S. PATENT DOCUMENTS

| 4,117,161 | A | 9/1978 | Pozuelo |
| 4,165,382 | A | 8/1979 | Pozuelo |
| 4,189,604 | A | 2/1980 | Umezawa et al. |
| 4,240,975 | A | 12/1980 | Umezawa et al. |
| 5,073,541 | A | 12/1991 | Taylor et al. |
| 5,206,018 | A | 4/1993 | Sehgal et al. |
| 5,225,435 | A | 7/1993 | Pawelek et al. |
| 5,576,290 | A | 11/1996 | Hadley |
| 5,674,839 | A | 10/1997 | Hruby et al. |
| 5,683,981 | A | 11/1997 | Hadley et al. |
| 5,714,576 | A | 2/1998 | Hruby et al. |
| 6,359,001 | B1 | 3/2002 | Drago |
| 7,452,868 | B2 | 11/2008 | Kuzma et al. |
| 8,003,689 | B2 | 8/2011 | Veverka |
| 8,481,498 | B1 | 7/2013 | Hoffman |
| 9,308,188 | B2 * | 4/2016 | Hoffman ............ A61K 31/4166 |
| 9,326,962 | B2 | 5/2016 | Hoffman |
| 9,757,348 | B2 | 9/2017 | Hoffman |
| 9,763,903 | B2 * | 9/2017 | Hoffman .............. A61K 9/0053 |
| 10,085,959 | B2 | 10/2018 | Hoffman |
| 2002/0128304 | A1 | 9/2002 | D'Amato |
| 2003/0059471 | A1 | 3/2003 | Compton et al. |
| 2006/0063699 | A1 | 3/2006 | Larsen |
| 2006/0122181 | A1 | 6/2006 | Ikemoto et al. |
| 2009/0030067 | A1 | 1/2009 | Wosikowski-Buters et al. |
| 2010/0216781 | A1 | 8/2010 | Perrin-Ninkovic et al. |
| 2013/0183263 | A1 | 7/2013 | Hoffman |
| 2013/0184214 | A1 | 7/2013 | Hoffman |
| 2013/0243873 | A1 | 9/2013 | Aversa et al. |
| 2015/0111878 | A1 | 4/2015 | Hoffman |
| 2015/0111937 | A1 | 4/2015 | Hoffman |
| 2015/0216827 | A1 | 8/2015 | Hoffman |
| 2015/0290279 | A1 | 10/2015 | Hoffman |

FOREIGN PATENT DOCUMENTS

| JP | 54062325 A | 5/1979 |
| JP | 2008515801 A | 5/2008 |
| WO | 0178704 A2 | 10/2001 |
| WO | WO 2002/100885 | 12/2002 |
| WO | WO 2009/054001 | 4/2009 |
| WO | WO 2009/109649 | 9/2009 |
| WO | WO 2009/131631 | 10/2009 |
| WO | WO 2010/022243 | 2/2010 |
| WO | WO 2010/118419 | 10/2010 |
| WO | WO 2011/112576 | 9/2011 |
| WO | WO 2012/123819 | 9/2012 |

(Continued)

OTHER PUBLICATIONS

Demser, 1979.*

(Continued)

*Primary Examiner* — Rei Tsang Shiao
(74) *Attorney, Agent, or Firm* — BakerHostetler

(57) ABSTRACT

The invention provides compositions and methods of treating autism. Specifically, the invention relates to treating the core symptoms of autism by administering α-methyl-DL-tyrosine.

19 Claims, 48 Drawing Sheets

(56) References Cited

FOREIGN PATENT DOCUMENTS

| WO | WO 2012/165984 | 12/2012 |
|---|---|---|
| WO | WO 2015/061328 | 4/2015 |
| WO | WO 2016/167944 | 10/2016 |

OTHER PUBLICATIONS

DEMSERDose, 1979.*
Cools's CAS: 77: 96941, 1972.*
Pasca et al., 2011, Nature medicine, 17(12); 1657-1662.*
Oberman et al., Expert Opinion on Investigational drugs, 2012, 21(12): 1819-1825.*
U.S. Appl. No. 15/695,327, filed Sep. 5, 2017.
U.S. Appl. No. 15/138,733, filed Apr. 26, 2016.
U.S. Appl. No. 15/059,602, filed Mar. 3, 2016.
U.S. Appl. No. 14/686,545, filed Apr. 14, 2015.
U.S. Appl. No. 14/520,116, filed Oct. 21, 2014.
U.S. Appl. No. 14/062,165, filed Oct. 24, 2013.
Bloemen et al., "Challenge and Therapeutic Studies Using Alpha-Methyl-para-Tyrosine (AMPT) in Neuropsychiatric Disorders: A Review," Central Nervous System Agents in Medicinal Chemistry, 8(4), Dec. 2008, 249-56.
Boni et al., "Radioiodine-labelled Alpha-methyl-tyrosine in Malignant Melanoma: Cell Culture Studies and Results in Patients," British Journal of Dermatology, Jul. 1997, 137(1), 96-100.
Brogden et al., "Alpha-Methyl-p-tyrosine: A Review of its Pharmacology and Clinical Use," Drugs, Feb. 1981, 21(2), 81-89.
Cabrera Lopez et al., "Effects of Rapamycin on Angiomyolipomas in Patients with Tuberous Sclerosis," Nefrologia, Apr. 2011, 31(3), 292-98.
Chen et al., "Progress in the Development of Bestatin Analogues as Aminopeptidases Inhibitors," Current Medical Chemistry, Mar. 2011, 8(7), 964-76.
Chhun et al., "7. The Cytochrome P-450 2C9/2C19 but Not the ABCB1 Genetic Polymorphism May Be Associated With the Liver Cytochrome 3A4 Induction by Phenytoin," Journal of Clinical Psychopharmacology, Jun. 2012, 32(3), 429-31.
Chiu et al., "Lipid-Based Nanoparticulate Systems for the Delivery of Anti-Cancer Drug Cocktails: Implications on Pharmacokinetics and Drug Toxicities," Current Drug Metabolism, 2009,10, 861-74.
De Kort et al., "Leaky Gut and Diabetes Mellitus: What is the Link?" Obesity Reviews, 2011, 12,449-58.
Dorr et al., "Evaluation of Melanotan-II, A Superpotent Cyclic Melanotropic Peptide in a Pilot Phase-I Clinical Study," Life Sciences, Apr. 1996, 58(20), 1777-84.
Ell, "Brain Tumor Uptake of Iodo-alpha-methyl-tyrosine," Journal of Nuclear Medicine, Nov. 1991, 32(11), 2193-94.
Espeillac et al., "S6 Kinase 1 is Required for Rapamycin-sensitive Liver Proliferation After Mouse Hepatectomy," The Journal of Clinical Investigation, Jul. 2011, 121(7), 2821-32.
Fan et al., "Impact of System L Amino Acid Transporter 1 (LAT1) on Proliferation of Human Ovarian Cancer Cells: A Possible Target for Combination Therapy with Anti-Proliferative Aminopeptidase Inhibitors," Biochemical Pharmacology, Sep. 15, 2010, 80(6), 811-18.
Fitzgerald et al., "Effect of MELANOTAN, [Nle(4), D-Phe(7)]-alpha-MSH, on Melanin Synthesis in Humans with MC1 R Variant Alleles," Peptides, Feb. 2006, 27(2), 388-94.
Fujimori et al., Mechanisms of Hyperglycemic Response to Chlorpromazine Administered into Lateral Ventricle in Rats-I, Possible Role of Dopaminergic Nervous System, Neuropharmacology, Pergamon Press, Oxford, 13(4), Apr. 1974.
Ichimura et al., "Immunohistochemical Expression of Aminopeptidase N (CD13) in Human Lung Squamous Cell Carcinomas, with Special Reference to Bestatin Adjuvant Therapy," Pathology International, Jun. 2006, 56(6), 296-300.
Kargiotis et al., "Epilepsy in the Cancer Patient," Cancer Chemotherapy and Pharmacology, Mar. 2011, 67(3), 489-501.
Krige et al., "CHR-2797: An Antiproliferative Aminopeptidase Inhibitor that Leads to Amino Acid Deprivation in Human Leukemic Cells," Cancer Research, Aug. 15, 2008, 68(16), 6669-79.
Kulke et al., "Future Directions in the Treatment of Neuroendocrine Tumors: Consensus Report of the National Cancer Institute Neuroendocrine Tumor Clinical Trials Planning Meeting," Journal of Clinical Oncology, Mar. 2011, 29(7), 934-43.
Landmark, "Antiepileptic Drugs in Non-Epilepsy Disorders—Relations Between Mechanisms of Action and Clinical Efficacy," CNS Drugs, 2008, 22(1), 27-47.
Liu et al., "Combinatorial Effects of Lapatinib and Rapamycin in Triple-Negative Breast Cancer Cells," Molecular Cancer Therapeutics, Aug. 2011, 10, 1460-69.
Longhurst et al., "Effects of Catecholamine Depletion with AMPT (alpha-methyl-para-tyrosine) in Obsessive-Compulsive Disorder," Biological Psychiatry, Elsevier Science, NY, 46(4), Aug. 1999, 573-76.
Longo et al., "Efficacy and Tolerability of Long-Acting Octreotide in the Treatment of Thymic Tumors: Results of a Pilot Trial," American Journal of Clinical Oncology, Apr. 2012, 35(2), 105-09.
Nakagami, "A Case of Malignant Pheochromocytoma Treated with 1311-metaiodobenzylguanidine and alpha-methyl-p-tyrosine," Japanese Journal of Medicine, May-Jun. 1990, 29(3), 329-33.
Ram et al., "Failure of alpha-methyltyrosine to Prevent Hypertensive Crisis in Pheochromocytoma," Archives of Internal Medicine, Nov. 1985, 145(11), 2114-15.
Russo, "Correlation Between Hepatocyte Growth Factor (HGF) and Gamma-Aminobutyric Acid (GABA) Plasma Levels in Autistic Children," Biomarker Insights, Jun. 1, 2013, 69-75.
Ryakhovsky et al., "The First Preparative Solution Phase Synthesis of Melanotan II," Beilstein Journal of Organic Chemistry, 2008, 4, 1-6.
Standards of Medical Care in Diabetes—2013, American Diabetes Association, Jan. 2013, vol. 36, Supp. 1, S11-S66.
Steinsapir et al., "Metyrosine and Pheochromocytoma," Archives of Internal Medicine, Apr. 1997, 157(8), 901-06.
Tada et al., "Three Cases of Malignant Pheochromocytoma Treated with Cyclophosphamide, Vincristine, and Dacarbazine Combination Chemotherapy and alpha-methyl-p-tyrosine to Control Hypercatecholaminemia," Hormone Research, Jan. 1998, 49(6), 295-97.
Taveria-DaSilva et al., "Sirolimus Therapy in Patients with Lymphangioleiomyomatosis," Summaries for Patients, Annals of Internal Medicine, Jun. 21, 2011, 154(12), 144.
Terauchi et al., "Inhibition of APN/CD 13 Leads to Suppressed Progressive Potential in Ovarian Carcinoma Cells," BMC Cancer, 2007, 7, 1-12.
Tsukamoto et al., "Aminopeptidase N (APN)/CD13 Inhibitor, Ubenimex, Enhances Radiation Sensitivity in Human Cervical Cancer," BMC Cancer, Mar. 2008, 8:74, 8 pages.
"Tyrosine Derivatives for Sale," Sigma-Aldrich, 2012, 1 page.
Voorhess, "Effect of alpha-methyl-p-tyrosine on 3,4-dihydroxyphenylalanine (DOPA) Excretion of Hamsters with Melanotic Melanoma," Cancer Research, Mar. 1968, 28, 452-54.
Yamada et al., "Involvement of Adrenaline in Diazepam-Induced Hyperglycemia in Mice," Life Sciences, Pergarmon Press, Oxford, 66(13), Feb. 18, 2000, 1213-21.
Zimmermann et al., "Prolonged Inhibition of Presynaptic Catecholamine Synthesis With a-Methyl-Para-Tyrosine Attenuates the Circadian Rhythm of Human TSH Secretion," J. Soc. GynecolInvesting, May/Jun. 2001, 8(3), 174-78.
Ziying et al., "Observation of Cabamazepine Treating Painful Diabetic Neuropathy," Medical Recapitulate, 15(8), Apr. 30, 2009, 1270-71.
He et al.,"Cytoplasm-predominant Pten associates with increased region-specific brain tyrosine hydroxylase and dopamine D2 receptors in mouse model with autistic traits" Molecular Autism, vol. 6, No. 63, 2015, 10 Pages.
Kato, "Intestinal First-Pass Metabolism of CYP3A4 Substrates" Drug Metab. Pharmacokinet., vol. 23, No. 2, pp. 87-94, 2008.

(56) References Cited

OTHER PUBLICATIONS

Sumida et al., Jpn. J. Clin. Pharmacol Ther., vol. 31, No. 2, Mar. 2000, pp. 305-306.

* cited by examiner

BP=blood pressure; SBP=systolic blood pressure; DBP=diastolic blood pressure and Pul=pulse

COMPOSITIONS AND METHODS FOR TREATING AUTISM

CROSS-REFERENCE TO RELATED APPLICATIONS

This application is a continuation-in-part (CIP) application of U.S. patent application Ser. No. 15/695,327, filed Sep. 5, 2017, which is a continuation of U.S. patent application Ser. No. 15/138,733, filed Apr. 26, 2016, now issued as U.S. Pat. No. 9,757,348, which is a continuation of U.S. patent application Ser. No. 14/520,116, filed Oct. 21, 2014, now issued as U.S. Pat. No. 9,326,962, which is a continuation-in-part of U.S. patent application Ser. No. 14/062,165, filed Oct. 24, 2013, now abandoned, which claims priority to and the benefit of U.S. Provisional Patent Application No. 61/894,261, filed Oct. 22, 2013, all of which are incorporated by reference herein in their entirety.

FIELD OF THE INVENTION

The invention relates to compositions and methods of treating autism. Specifically, the invention relates to treating the core symptoms of autism by administering α-methyl-DL-tyrosine.

BACKGROUND OF THE INVENTION

Autism spectrum disorder (ASD) or autism is defined in the Diagnostic and Statistics Manual of Mental Disorders V (DSM-5) by "difficulties in social communication and social interaction, and restricted and repetitive behavior, interests or activities". Childhood autism is more prevalent than childhood cancer, juvenile diabetes, and pediatric acquired immunodeficiency syndrome (AIDS) combined, with an estimated prevalence of 1.5 million in the United States (US), 3 million children in Europe and tens of millions throughout the rest of the world. Autism also represents a substantial economic burden in both children and adults. More disturbing is that, for no explicable reason, childhood autism appears to be increasing at a rate of 10-17% per year. Lastly, there are currently no approved medications that address the core symptoms of autism. Autism is a serious disease that represents an area of significant economic burden and unmet medical need.

Autism was first described in 1943 by Dr. Leo Kanner who described his 5 year old patient as, " . . . happiest when left alone, almost never cried to go with his mother, did not seem to notice his father's homecomings, and was indifferent to visiting relatives . . . wandered about smiling, making stereotyped movements with his fingers . . . spun with great pleasure anything he could seize upon to spin . . . . Words to him had a specifically literal, inflexible meaning . . . . When taken into a room, he completely disregarded the people and instantly went for objects", as cited by Lai, M. C., et al. Autism. *Lancet*, 2014. 383 (9920): p. 896-910.

Originally autism was thought to be a form of childhood schizophrenia. However, in the mid-1980s, it was found that autism is a heritable disorder and believed to have a genetic etiology. Currently, autism is defined diagnostically in the *Diagnostic and Statistical Manual of Mental Disorders, 5th Edition* (DSM-5) (2013) by "difficulties in social communication and social interaction, and restricted and repetitive behavior, interests or activities." The diagnostic criteria in DSM-5 for the features "difficulties in social communication and social interaction" of ASD include (1) deficits in social-emotional reciprocity, ranging, for example, from abnormal social approach and failure of normal back-and-forth conversation; to reduced sharing of interests, emotions, or affect; to failure to initiate or respond to social interactions; (2) Deficits in nonverbal communicative behaviors used for social interaction, ranging, for example, from poorly integrated verbal and nonverbal communication; to abnormalities in eye contact and body language or deficits in understanding and use of gestures; to a total lack of facial expressions and nonverbal communication; and (3) deficits in developing, maintaining, and understanding relationships, ranging, for example, from difficulties adjusting behavior to suit various social contexts; to difficulties in sharing imaginative play or in making friends; to absence of interest in peers.

Typically displayed in early childhood, autism is associated with many co-morbidities that include epilepsy, Fragile-X syndrome, Retts syndrome, attention deficit/hyperactivity disorder (ADHD), abnormal sensory or motor responses, disturbed sleep, reduced cognitive functionality, anxiety and aggression.

In 2010, the CDC reported the rate of autism in the US to be 1 in 68 children, with boys being 5 times more susceptible than girls. This means that 1 in 42 boys are diagnosed with autism. There was an increase of about 30% since the assessment of autism prevalence conducted in 2014, and more than double the rate that was reported only 12 years and the problem is growing rapidly. In New Jersey the observed rate of autism was 1 in 46 children, which means that 1 in 29 boys born in New Jersey are likely to be autistic.

The financial cost of raising an autistic child was estimated in 2014 to be $3.2M more than the cost of raising a non-autistic child, and this does not take into account the societal costs of maintaining this population as adults once their families are no longer able to do so. The societal costs of autism are broad and deep, and many have never been explored. For example, it was only in mid-2017 that information was developed on the rate of healthcare utilization by autistics and it was found that their need for psychiatric care as well as care for the high incidence of autism associated comorbidities was far beyond that of the general population or other elements of the psychiatric patient population. Similarly, it was not until September of 2017 that the rate of school suspension and expulsion was dramatically higher in the autistic population, and growing as the autistic population grew in numbers.

Recently, attention has been brought to bear on autism associated mortality rates. Although autism is not typically considered to be a fatal disease, a number of investigators have reported a significantly increased mortality in the autistic population with the major cause of death being suicide. A matched case cohort study based upon the Swedish National Patient Registry and the Cause of Death Registry looked at deaths between 1987 and 2009, and found a 256% greater death rate in autistic patients compared to the general population. The mean age at the time of death was 70.2 years for the general population and 58.39 for patients with autism, with suicide associated with better performing patients. A review of 1,706 children and adolescents reported an 18% increased risk of suicidal ideation or attempts in autism. 35% of patients with Asperger's syndrome were reported in a Canadian study to have attempted suicide. Similarly, in Japan, Australia, England, and Belgium. In a French review of the PubMed literature, it was found that overall 21.3% of autism patients reported suicidal ideation or had attempted suicide, with the noteworthy observation that " . . . the methods used are often violent".

Enormous resources are being spent on research into the causes of autism. Genetic, dietary, developmental, pharmacologic, environmental, and behavioral elements have all been implicated as potential causes of this syndrome.

A purified, single enantiomer presentation of molecule—α-methyl-L-tyrosine, currently marketed as Demser®, is known to inhibit tyrosine hydroxylase, which is the rate limiting enzyme in the biosynthesis of catecholamine's consequent to enzyme-mediated conversion of L-tyrosine to DOPA (dihydroxy-phenylalanine). This first step in catecholamine synthesis is highly stereospecific for L-tyrosine. L-AMPT, a methylated L-tyrosine, acts as a competitive inhibitor for tyrosine hydroxylase (Demser® Prescribing Information, 2015; FDA Summary Basis of Approval [SBA] for Demser®, 1979). Demser® was initially approved by the FDA in 1979 and is indicated for use in the treatment of patients with pheochromocytoma for (1) the preoperative preparation of patients for surgery, (2) management of patients when surgery is contraindicated, and (3) chronic treatment of patients with malignant pheochromocytoma. The recommended initial dosage of Demser® for adults and children 12 years of age and older is 250 mg orally four times daily. This dosage may be increased by 250 mg to 500 mg every day to a maximum of 4.0 g/day in 4 divided doses. Although Demser® is commercially available, those ordinarily skilled in the art have not developed methods for treating autism or its core symptoms by administering a racemic mixture of α-methyl-DL-tyrosine, i.e., DL-AMPT.

Given the widespread concern over (a) dramatic increases in prevalence of autism, (b) devastating impact of the disorder on children and their families, and (c) substantial social and economic burden that autism place on communities, educational, medical and mental health systems within our society, autism represents a public health emergency. Accordingly, there exists a vital need for therapeutically effective methods for treating autism, in particular, the core symptoms of this disorder.

SUMMARY OF THE INVENTION

In one aspect, the invention provides a method for treating an autism in a subject in need thereof, the method comprising administering to said subject a composition comprising a therapeutically effective amount of α-methyl-DL-tyrosine and a pharmaceutically acceptable carrier. In an exemplary embodiment, the composition comprises α-methyl-DL-tyrosine in an amount ranging from about 50 mg (w/w) to about 500 mg (w/w).

In another aspect, the invention provides a method for providing a plasma concentration of a therapeutic drug for a long term for treating an autism in a subject in need thereof, the method comprising administering to said subject said therapeutic drug at a concentration ranging from about 50 mg (w/w) to about 500 mg (w/w) three times a day, wherein said therapeutic drug is α-methyl-DL-tyrosine, wherein said plasma concentration ranges from about 500 ng/ml to 5000 ng/ml, and wherein said term is at least 1 week.

In another aspect, the invention provides a method for treating an autism associated clinical trait in a subject in need thereof, the method comprising administering to said subject a composition comprising a therapeutically effective amount of α-methyl-DL-tyrosine, thereby treating said autism associated clinical trait in said subject. In an exemplary embodiment, the clinical trait is a deficit in social communication, a deficit in social interaction, a deficit in social motivation, lethargy and social withdrawal, inappropriate speech, hyperactivity, stereotypic behavior, irritability and agitation, restrictive behavior, repetitive behavior, ritualistic behavior, sameness behavior, compulsive behavior, self-injurious behavior or a combination thereof.

Other features and advantages of the present invention will become apparent from the following detailed description examples and figures. It should be understood, however, that the detailed description and the specific examples while indicating preferred embodiments of the invention are given by way of illustration only, since various changes and modifications within the spirit and scope of the invention will become apparent to those skilled in the art from this detailed description.

DETAILED DESCRIPTION OF THE INVENTION

Figure 1:
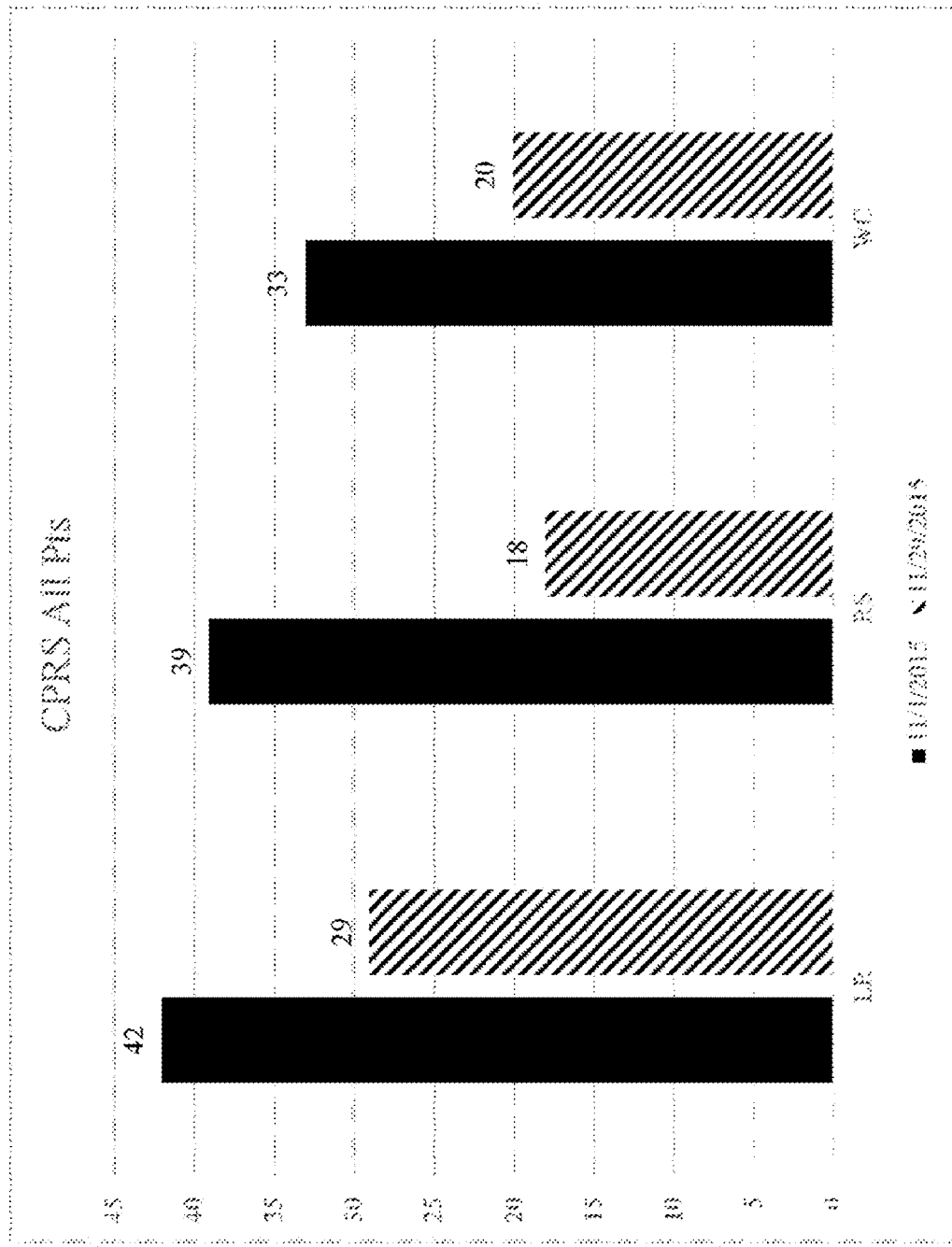
FIG. 1 depicts Conners Parent Rating Scale Data results.

The present subject matter may be understood more readily by reference to the following detailed description which forms a part of this disclosure. It is to be understood that this invention is not limited to the specific products, methods, conditions or parameters described and/or shown herein, and that the terminology used herein is for the purpose of describing particular embodiments by way of example only and is not intended to be limiting of the claimed invention.

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular.

As employed above and throughout the disclosure, the following terms and abbreviations, unless otherwise indicated, shall be understood to have the following meanings.

In the present disclosure the singular forms "a," "an," and "the" include the plural reference, and reference to a particular numerical value includes at least that particular value, unless the context clearly indicates otherwise. Thus, for example, a reference to "a compound" is a reference to one or more of such compounds and equivalents thereof known to those skilled in the art, and so forth. The term "plurality", as used herein, means more than one. When a range of values is expressed, another embodiment includes from the one particular and/or to the other particular value. Similarly, when values are expressed as approximations, by use of the antecedent "about," it is understood that the particular value forms another embodiment. All ranges are inclusive and combinable.

As used herein, the terms "component," "composition," "composition of compounds," "compound," "drug," "pharmacologically active agent," "active agent," "therapeutic," "therapy," "treatment," or "medicament" are used interchangeably herein to refer to a compound or compounds or composition of matter which, when administered to a subject (human or animal) induces a desired pharmacological and/or physiologic effect by local and/or systemic action.

As used herein, the ensuing terms are defined, as follows:
ABA Applied Behavioral Analysis
ABC-C Aberrant Behavior Checklist-Community
ADHD Attention Deficit Hyperactivity Disorder
ADIR Autistic Diagnosis Interview Review
ADME Absorption, Distribution, Metabolism and Elimination
ADOS-2 Autism Diagnosis Observation Schedule, Second Edition AE Adverse Events
AIDS Acquired immunodeficiency syndrome
ASD Autism spectrum disorder
AST Aspartate Aminotransferase
ALT Alanine Aminotransferase
AUC Area under the concentration time curve
$AUC_{0-8}$ Area under the concentration time curve from 0 to 8 hours
$AUC_{0-12}$ Area under the concentration time curve from 0 to 12 hours
$AUC_{0-\infty}$ Area under the concentration time curve from 0 to infinity
$AUC_{0-tz}$ Area under the concentration time curve from 0 to the last quantifiable concentration
CFR Code of Federal Regulations
CGI-I Clinical Global Impression-Overall Improvement
CGI-S Clinical Global Impression-Severity of Illness
Cmax Maximum Concentration
CNS Central Nervous System
DL-AMPT Racemic (D and L isomer) α-methyl-para-tyrosine
DOPA Dihydroxy-phenylalanine
DSM-5 Diagnostic and Statistics Manual of Mental Disorders V
EI Early Intervention
EOP2 End of Phase 2
FDA Food and Drug Administration
FDASIA Food and Drug Administration Safety and Innovation Act
FOBs Functional Observation Battery Assessments
GMP Good Manufacturing Practice
HBV Hepatitis B Virus
HCVA Hemorrhagic Cerebrovascular Accident
HED Human Equivalent Doses
HIV Human Immunodeficiency Virus
IEP Individualized Educational Program
L-AMPT L isomer of α-methyl-para-tyrosine
LC-MS/MS Liquid Chromatographic Mass Spectrometric
LOCF Last Observation Carried Forward
LQTS Long QT Syndrome
MTD Maximum Tolerated Dose
NDA New Drug Application
NOAEL No Observed Adverse Effect Level
PD Pharmacodynamic
PK Pharmacokinetic
PND Post Natal Day
PSP Pediatric Study Plan
RBS-R Repetitive Behavior Score-Revised
SBA Summary Basis of Approval
SRS-2 Social Responsiveness Scale, Second Edition
$t_{1/2}$ Half Life
TdP Torsade's de Pointes
TID Three times daily
TK Toxicokinetic
TQT Thorough QT
ULN Upper Limit of Normal
USAN United States Adopted Name
VABS II Vineland Adaptive Behavior Scales, Second Edition With respect to autism, for example, the negative effect or symptoms can include any of those that are the subject of the diagnostic criteria specified for autism spectrum disorder in the American Psychiatric Association's Diagnostic and Statistical Manual, Fifth Edition (DSM-5, DSM-V), the contents of which are incorporated by reference herein, e.g., deficits in social-emotional reciprocity (ranging, for example, from abnormal social approach and failure of normal back-and-forth conversation; to reduced sharing of interests, emotions, or affect; to failure to initiate or respond to social interactions) deficits in nonverbal communicative behaviors used for social interaction (ranging, for example, from poorly integrated verbal and nonverbal communication; to abnormalities in eye contact and body language or deficits in understanding and use of gestures; to a total lack of facial expressions and nonverbal communication); deficits in developing, maintaining, and understanding relationships (ranging, for example, from difficulties adjusting behavior to suit various social contexts; to difficulties in sharing imaginative play or in making friends; to absence of interest in peers); stereotyped or repetitive motor movements, use of objects, or speech (e.g., simple motor stereotypes, lining up toys or flipping objects, echolalia, idiosyncratic phrases); insistence on sameness, inflexible adherence to routines, or ritualized patterns of verbal or nonverbal behavior (e.g., extreme distress at small changes, difficulties with transitions, rigid thinking patterns, greeting rituals, need to take same route or eat same food every day); highly restricted, fixated interests that are abnormal in intensity or focus (e.g., strong attachment to or preoccupation with unusual objects, excessively circumscribed or perseverative interests); and hyper- or hyporeactivity to sensory input or unusual interest in sensory aspects of the environment (e.g. apparent indifference to pain/temperature, adverse response to specific sounds or textures, excessive smelling or touching of objects, visual fascination with lights or movement).

Some subpopulations of patients on the autism spectrum, include those patients diagnosed with Asperger's Disorder (i.e., Asperger Syndrome) or Social Communication Disorder, exhibit symptoms of Attention Deficit Hyperactivity Disorder (ADHD) (e.g., inattention, hyperactivity, and impulsivity) and/or tics (motor tics or vocal tics). See, e.g., DSM-5.

Assessment of autism symptoms, or any of the symptoms of the present disclosure, can be performed using methods known in the art. For example, one method of assessing autism symptoms is the Clinical Global Impressions (CGI) scale based upon changes from baseline in various psychometric tests. These tests can include the Aberrant Behavior Checklist-Community (ABC-C), Conners Parent Rating Scale and the Autism Diagnostic Observation Schedule (ADOS). Autism symptoms can also be assessed from the clinician's personal, clinical observations, from videographic information taken at regularly scheduled clinic visits, and from information provided by the subject's caregivers over time. Compositions and methods of the disclosure result in a reduction of at least 1 point in at least one dimension of the Conners Parent Rating Scale assessment score.

As employed above and throughout the disclosure the term "effective amount" refers to an amount effective, at dosages, and for periods of time necessary, to achieve the desired result with respect to the treatment of the relevant disorder, condition, or side effect. It will be appreciated that the effective amount of components of the present invention will vary from patient to patient not only with respect to the particular compound, component or composition selected, the route of administration, and the ability of the components to elicit a desired result in the individual, but also with respect to factors such as the disease state or severity of the condition to be alleviated, hormone levels, age, sex, weight of the individual, the state of being of the patient, and the severity of the pathological condition being treated, concurrent medication or special diets then being followed by the particular patient, and other factors which those skilled in the art will recognize, with the appropriate dosage being at the discretion of the attending physician. Dosage regimes may be adjusted to provide improved therapeutic response. An effective amount is also one in which any toxic or detrimental effects of the components are outweighed by the therapeutically beneficial effects.

The invention also provides a pharmaceutical composition comprising compounds of the invention and one or more pharmaceutically acceptable carriers. "Pharmaceutically acceptable carriers" include any excipient which is nontoxic to the cell or mammal being exposed thereto at the dosages and concentrations employed. The pharmaceutical composition may include one or additional therapeutic agents.

"Pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio.

Examples of a pharmaceutically acceptable carrier include, for example, but not limited to, solvents, dispersion media, buffers, coatings, antibacterial and antifungal agents, wetting agents, preservatives, buggers, chelating agents, antioxidants, isotonic agents and absorption delaying agents.

Examples of a pharmaceutically acceptable carrier also include, for example, but not limited to, water; saline; phosphate buffered saline; dextrose; glycerol; alcohols such as ethanol and isopropanol; phosphate, citrate and other organic acids; ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; EDTA; salt forming counterions such as sodium; and/or nonionic surfactants such as TWEEN, polyethylene glycol (PEG), and PLURONICS; isotonic agents such as sugars, polyalcohols such as mannitol and sorbitol, and sodium chloride; as well as combinations thereof.

Within the present invention, the disclosed compounds may be prepared in the form of pharmaceutically acceptable salts. "Pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. These physiologically acceptable salts are prepared by methods known in the art, e.g., by dissolving the free amine bases with an excess of the acid in aqueous alcohol, or neutralizing a free carboxylic acid with an alkali metal base such as a hydroxide, or with an amine.

Compounds described herein can be prepared in alternate forms. For example, many amino-containing compounds can be used or prepared as an acid addition salt. Often such salts improve isolation and handling properties of the compound. For example, depending on the reagents, reaction conditions and the like, compounds as described herein can be used or prepared, for example, as their hydrochloride or tosylate salts. Isomorphic crystalline forms, all chiral and racemic forms, N-oxide, hydrates, solvates, and acid salt hydrates, are also contemplated to be within the scope of the present invention.

Certain acidic or basic compounds of the present invention may exist as zwitterions. All forms of the compounds, including free acid, free base and zwitterions, are contemplated to be within the scope of the present invention. It is well known in the art that compounds containing both amino and carboxy groups often exist in equilibrium with their zwitterionic forms. Thus, any of the compounds described herein that contain, for example, both amino and carboxy groups, also include reference to their corresponding zwitterions.

The term "stereoisomers" refers to compounds that have identical chemical constitution, but differ as regards the arrangement of the atoms or groups in space. The term "enantiomers" refers to stereoisomers that are mirror images of each other that are non-superimposable.

The term "administering" means either directly administering a compound or composition of the present invention, or administering a prodrug, derivative or analog which will form an equivalent amount of the active compound or substance within the body.

The term "inhibitor" as used herein includes compounds that inhibit the expression or activity of a protein, polypeptide or enzyme and does not necessarily mean complete inhibition of expression and/or activity. Rather, the inhibition includes inhibition of the expression and/or activity of a protein, polypeptide or enzyme to an extent, and for a time, sufficient to produce the desired effect.

While not intending to be bound by any particular mechanism of operation, it is believed that the tyrosine hydroxylase inhibitors according to the present invention function by decreasing the amount of adrenaline secreted into the bloodstream.

The tyrosine hydroxylase inhibitor is well known in the art and fully described in, for example, U.S. Patent Application Publications US 2015/0290279, US 2015/0216827, US 2015/0111937, US 2015/0111878, US 2013/0184214, and US 20130183263; U.S. Pat. Nos. 8,481,498, 9,308,188, and 9,326,962; and PCT Patent Application Publication WO2015061328, which are incorporated by reference herein in their entirety. Any suitable tyrosine hydroxylase inhibitor, known to one of skilled in the art, can be used.

In certain embodiments, the tyrosine hydroxylase inhibitor is a tyrosine derivative. The tyrosine derivative can be capable of existing in different isomeric forms, including stereoisomers and enantiomers. The tyrosine derivative can, for example, exist in both L-form or D-form. The tyrosine derivative can, for example, also exist in a racemic form.

Representative tyrosine derivatives include, for example, one or more of methyl (2R)-2-amino-3-(2-chloro-4 hydroxyphenyl) propanoate, D-tyrosine ethyl ester hydrochloride, methyl (2R)-2-amino-3-(2,6-dichloro-3,4-dimethoxyphenyl) propanoate H-D-tyrosine(tBu)-allyl ester hydrochloride, methyl (2R)-2-amino-3-(3-chloro-4,5-dimethoxyphenyl) propanoate, methyl (2R)-2-amino-3-(2-chloro-3-hydroxy-4-methoxyphenyl) propanoate, methyl (2R)-2-amino-3-(4-[(2-chloro-6-fluorophenyl) methoxy] phenyl) propanoate, methyl (2R)-2-amino-3-(2-chloro-3,4-dimethoxyphenyl) propanoate, methyl (2R)-2-amino-3-(3-chloro-5-fluoro-4-hydroxyphenyl) propanoate, diethyl 2-(acetylamino)-2-(4-[(2-chloro-6-fluorobenzyl) oxy] benzyl malonate, methyl (2R)-2-amino-3-(3-chloro-4-methoxyphenyl) propanoate, methyl (2R)-2-amino-3-(3-chloro-4-hydroxy-5-methoxyphenyl) propanoate, methyl (2R)-2-amino-3-(2,6-dichloro-3-hydroxy-4-methoxyphenyl) propanoate, methyl (2R)-2-amino-3-(3-chloro-4-hydroxyphenyl) propanoate, H-DL-tyrosine methyl ester hydrochloride, H-3,5-diiodo-tyrosine methyl ester hydrochloride, H-D-3,5-diiodo-tyrosine methyl ester hydrochloride, H-D-tyrosine methyl ester hydrochloride, D-tyrosine methyl ester hydrochloride, D-tyrosine-methyl ester hydrochloride, methyl D-tyrosinate hydrochloride, H-D-tyrosine methyl ester hydrochloride, D-tyrosine methyl ester hydrochloride, H-D-tyrosine methyl ester-hydrochloride, (2R)-2-amino-3-(4-hydroxyphenyl) propionic acid, (2R)-2-amino-3-(4-hydroxyphenyl) methyl ester hydrochloride, methyl (2R)-2-amino-3-(4-hydroxyphenyl) propanoate hydrochloride, methyl (2R)-2-azanyl-3-(4-hydroxyphenyl) propanoate hydrochloride, 3-chloro-L-tyrosine, 3-nitro-L-tyrosine, 3-nitro-L-tyrosine ethyl ester hydrochloride, DL-m-tyrosine, DL-o-tyrosine, Boc-tyrosine (3,542)-OSu, Fmoc-tyrosine(3-NO2)-OH, α-methyl-L-tyrosine, α-methyl-D-tyrosine, and α-methyl-DL-tyrosine. In certain embodiments of the invention, the tyrosine derivative is α-methyl-L-tyrosine as shown below:

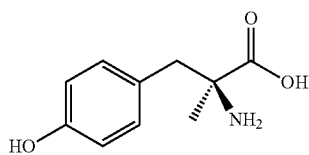

In other embodiments, the tyrosine derivative is α-methyl-D-tyrosine. In other embodiments, the tyrosine derivative is α-methyl-DL-tyrosine in a racemic form as shown below:

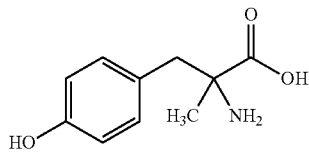

In a particular embodiment, the tyrosine derivative is a structural variant of α-methyl-L-tyrosine or α-methyl-DL-tyrosine. The structural variants of α-methyl-L-tyrosine or α-methyl-DL-tyrosine are well known in the art and fully described in, for example, U.S. Pat. No. 4,160,835, which is incorporated by reference herein in its entirety.

In one embodiment, the tyrosine derivative of the invention is an arylalanine compound having the formula:

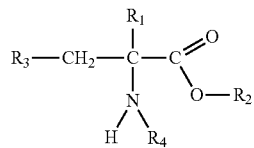

wherein $R_1$ is hydrogen, methyl or ethyl ester group, or alkyl of from 1 to 4 carbon atoms; $R_2$ is hydrogen, lower alkyl, lower alkene, succinimide, or alkyl of from 1 to 4 carbon atoms; $R_3$ is a substituted benzene ring of the following general formula

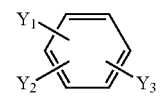

wherein $Y_1$, is located at the para position and is hydrogen, hydroxy, methyl ether, dimethyl ether, trimethyl ether, or an unsubstituted or halogen-substituted benzyl; $Y_2$, and $Y_3$ are the same or different and wherein one or both $Y_2$, and $Y_3$ located at either meta position or ortho position, and wherein $Y_2$, and $Y_3$ are hydrogen, hydroxy, halogen, methyl ether, or nitro; and $R_4$ is hydrogen, acetyl, tert-butyloxycarbonyl or fluorenylmethyloxycarbonyl.

In some embodiments, Y1 and Y2 are the same or different and are selected from hydrogen, cyanoamino, carboxyl, cyano, thiocarbamoyl, aminomethyl, guanidino, hydroxy, methanesulfonamido, nitro, amino, methanesulfonyloxy, carboxymethoxy, formyl, methoxy and a substituted or unsubstituted 5- or 6-membered heterocyclic ring containing carbon and one or more nitrogen, sulfur or oxygen atoms, specific examples of such heterocyclic rings being pyrrol-1-yl, 2-carboxypyrrol-1-yl, imidazol-2-ylamino, indol-1-yl, carbazol-9-yl, 4,5-dihydro-4-hydroxy-4-trifluoromethylthiazol-3-yl, 4-trifluoromethylthiazol-2-yl, imidazol-2-yl and 4,5-dihydroimidazol-2-yl, such that (a) Y1 and Y2 cannot both be hydroxy, (b) Y1 and Y2 cannot both be hydrogen and (c) when one of Y1 and Y2 is hydrogen, the other cannot be hydroxyl.

In one example, $R_3$ is a substituted or unsubstituted benzoheterocyclic ring having the formula:

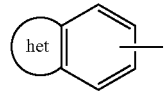

in which the benzoheterocyclic ring is selected from the group consisting of indolin-5-yl, 1-(N-benzoylcarbamimidoyl)-indolin-5-yl, 1-carbamimidoylindolin-5-yl, 1H-2-oxindol-5-yl, indol-5-yl, 2-mercaptobenzimidazol-5(6)-yl, 2-aminobenzimidazol-5(6)-yl, 2-methanesulfonamido-benzimidazol-5(6)-yl, 1H-benzoxazol-2-on-6-yl, 2-aminobenzothiazol-6-yl, 2-amino-4-mercaptobenzothiazol-6-yl, 2,1,3-benzothiadiazol-5-yl, 1,3-dihydro-2,2-dioxo-2,1,3-benzothiadiazol-5-yl, 1,3-dihydro-1,3-dimethyl-2,2-dioxo-2,1,3-benzothiadiazol-5-yl, 4-methyl-2(1H)-oxoquinolin-6-yl, quinoxalin-6-yl, 2-hydroxquinoxalin-6-yl, 2-hydroxyquinoxalin-7-yl, 2,3-dihydroxyquinoxalin-6-yl and 2,3-dihydro-3(4H)-oxo-1,4-benzoxazin-7-yl.

In another example, $R_3$ is a substituted or unsubstituted heterocyclic ring having the formula:

in which the heterocyclic ring is selected from the group consisting of 5-hydroxy-4H-pyran-4-on-2-yl, 2-hydroxypyrid-4-yl, 2-aminopyrid-4-yl, 2-carboxypyrid-4-yl, or tetrazolo[1,5-a]pyrid-7-yl.

In one particular embodiment, the tyrosine hydroxylase inhibitor is aquayamycin. In one example, aquayamycin is a compound of the formula set forth below.

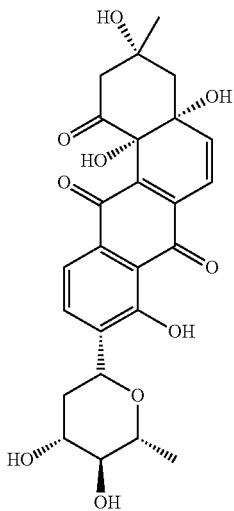

In another particular embodiment, the tyrosine hydroxylase inhibitor is oudenone. In one example, oudenone is a compound of the formula set forth below.

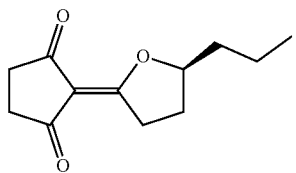

Other suitable tyrosine hydroxylase inhibitor, known to one of skilled in the art, can also be used. Example of other tyrosine hydroxylase inhibitor include, for example, but not limited to, cycloheximide, anisomycin, 3-iodo-L-tyrosine, pyratrione, phenyl carbonyl derivatives having catechol or triphenolic ring systems, for example, phenethylamine and gallic acid derivatives, 4-isopropyltropolone, 2-(4-thiazolyl) benzimidazole, 8-hydroxyquinoline, o-phenantroline, 5-iodo-8-hydroxyquinoline, bilirubin, 2,9-dimethyl-1, 10-phenantroline, α-α'-dipyridil, dibenzo [f,h]quinoxaline, 2,4,6-tripyridil-s-triazine, ethyl 3-amino4H-pyrrolo-isoxazole-5(6H)-carboxylate, α-nitroso-β-naphthol, sodium diethyldithiocarbamate, ethylenediamineteraacetic acid (See R Hochster, Metabolic Inhibitors V4: A Comprehensive Treatise 52 Elsevier (2012)).

In a particular embodiment, the tyrosine hydroxylase inhibitor is L1:79, which refers to α-methyl-DL-tyrosine in a racemic form or D,L α-methyl-para-tyrosine (abbreviated as DL-AMPT).

α-methyl-DL-tyrosine inhibits the activity of tyrosine hydroxylase (TH), which catalyzes the first transformation in catecholamine biosynthesis, i.e., the conversion of tyrosine to dihydroxyphenylalanine (DOPA), which is the rate limiting step in catecholamine synthesis. α-methyl-DL-tyrosine is a tyrosine analog that competes competitively for TH and is excreted mostly unchanged in the urine.

In preliminary testing, it was observed that Demser (i.e., α-methyl-L-tyrosine) had a beneficial effect on the symptoms of leaky gut, but that this effect was short lived. The racemic mixture (i.e., α-methyl-DL-tyrosine) was observed to have a greater physiologic effect and half-life. This may be due to the failure of the D amino acid isomer to be transported by the different L amino acid transport systems that exist within the body, or by completion for renal excretion that allows the L isomer to persist for a longer duration.

In another aspect, the invention provides a pharmaceutical composition comprising a therapeutically effective amount or dose of a tyrosine hydroxylase inhibitor (e.g., α-methyl-DL-tyrosine) and a pharmaceutically acceptable carrier.

Effective doses of the compositions of the present invention, for treatment of autism as described herein vary depending upon many different factors, including means of administration, target site, physiological state of the patient, whether the patient is an adult or a child, other medications administered, and whether treatment is prophylactic or therapeutic. Usually, the patient is a human but non-human mammals including transgenic mammals can also be treated. Treatment dosages may be titrated using routine methods known to those of skill in the art to optimize safety and efficacy.

The pharmaceutical compositions of the invention may include a "therapeutically effective amount." A "therapeutically effective amount" refers to an amount effective, at dosages and for periods of time necessary, to achieve the desired therapeutic result. A therapeutically effective amount of a molecule may vary according to factors such as the disease state, age, sex, and weight of the individual, and the ability of the molecule to elicit a desired response in the individual. A therapeutically effective amount is also one in which any toxic or detrimental effects of the molecule are outweighed by the therapeutically beneficial effects.

As used herein, the terms "treat" and "treatment" refer to therapeutic treatment, including prophylactic or preventative measures, wherein the object is to prevent or slow down (lessen) an undesired physiological change associated with a disease or condition. Beneficial or desired clinical results include, but are not limited to, alleviation of symptoms, diminishment of the extent of a disease or condition, stabilization of a disease or condition (i.e., where the disease or condition does not worsen), delay or slowing of the progression of a disease or condition, amelioration or palliation of the disease or condition, and remission (whether partial or total) of the disease or condition, whether detectable or undetectable. Those in need of treatment include those already with the disease or condition as well as those prone to having the disease or condition or those in which the disease or condition is to be prevented.

Dosage regimens may be adjusted to provide the optimum desired response (e.g., a therapeutic or prophylactic response).

In one example, a single bolus may be administered. In another example, several divided doses may be administered over time. In yet another example, a dose may be proportionally reduced or increased as indicated by the exigencies of the therapeutic situation. Dosage unit form, as used herein, refers to physically discrete units suited as unitary dosages for treating mammalian subjects. Each unit may contain a predetermined quantity of active compound calculated to produce a desired therapeutic effect. In some embodiments, the dosage unit forms of the invention are dictated by and directly dependent on the unique characteristics of the active compound and the particular therapeutic or prophylactic effect to be achieved.

The composition of the invention may be administered only once, or it may be administered multiple times. For multiple dosages, the composition may be, for example, administered three times a day, twice a day, once a day, once every two days, twice a week, weekly, once every two weeks, or monthly.

It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

"Administration" to a subject is not limited to any particular delivery system and may include, without limitation, oral (for example, in capsules, suspensions or tablets), parenteral (including subcutaneous, intravenous, intramedullary, intraarticular, intramuscular, or intraperitoneal injection), topical, or transdermal. Administration to a host may occur in a single dose or in repeat administrations, and in any of a variety of physiologically acceptable salt forms, and/or with an acceptable pharmaceutical carrier and/or additive as part of a pharmaceutical composition (described earlier). Once again, physiologically acceptable salt forms and standard pharmaceutical formulation techniques are well known to persons skilled in the art (see, for example, Remington's Pharmaceutical Sciences, Mack Publishing Co.).

In one aspect, the dosage of tyrosine hydroxylase inhibitor may range from about 1 mg to about 4 g. In a particular embodiment, the dosage of tyrosine hydroxylase inhibitor may range from about 10 mg to about 1500 mg. In some suitable embodiments of the invention, the composition comprises a tyrosine hydroxylase inhibitor (i.e., α-methyl-DL-tyrosine) in an amount ranging from about 50 mg (w/w) to about 1500 mg (w/w); from about 50 mg (w/w) to about 500 mg (w/w); from about 75 mg (w/w) to about 350 mg (w/w); from about 90 mg (w/w) to about 350 mg (w/w); from about 100 mg (w/w) to about 300 mg (w/w); or from about 100 mg (w/w) to about 200 mg (w/w). In one embodiment, the composition comprises a tyrosine hydroxylase inhibitor (i.e., α-methyl-DL-tyrosine) in an amount of about 90, 100, 125, 150, 175, 200, 250, 300, 350, 400, 500, 750, 1000, or 1500 mg (w/w/). As used herein, a "composition" refers to any composition that contains a pharmaceutically effective amount of one or more active ingredients (e.g., a tyrosine hydroxylase inhibitor, another acne treating agent, or a combination thereof).

In some embodiments, a plurality of compositions having different dosages are administered concurrently or sequentially. For instance, in one embodiment, a first composition comprising α-methyl-DL-tyrosine in an amount of about 200 mg (w/w) and a second composition comprising α-methyl-DL-tyrosine in an amount of about 100 mg (w/w) are administered concurrently. In another embodiment, a first composition comprising α-methyl-DL-tyrosine in an amount of about 200 mg (w/w) and a second composition comprising α-methyl-DL-tyrosine in an amount of about 100 mg (w/w) are administered sequentially.

In one aspect, the composition is administered for at least about 1, 2, 3, 4, 5, 6, 7, 8, 9, 10, 11, or 12 weeks. In another aspect, the composition is administered for a duration of 1, 2, 3, 4, 5, 6, 7, 8, 9, 10, 11, or 12 week dosing period. In yet another aspect, the composition is administered for a duration of 1, 2, 3, 4, 5, 6, 7, 8, 9, 10, 11, or 12 month dosing period.

In another aspect, the invention provides a method for obtaining a plasma concentration of a therapeutic tyrosine hydroxylase inhibitor drug (e.g., α-methyl-DL-tyrosine) for a long term for treating an autism in a subject in need thereof, the method comprising administering to said subject said therapeutic drug at a concentration ranging from about 50 mg (w/w) to about 500 mg (w/w) three times a day, wherein said plasma concentration ranges from about 500 ng/ml to 5000 ng/ml, and wherein said term is at least 1 week. In one embodiment, to obtain a desired plasma concentration, the drug is administered for at least 1 day, 2 day, 3 day, 4 day, 5 day, 6 day, 1 week, 2 week, 3 week, or 4 week. In a particular embodiment, to obtain a desired plasma concentration, the drug is administered for a duration ranging from about 1 day to about 4 weeks; from about 2 days to about 4 weeks; or from about 1 week to about 4 weeks. In some embodiments, to obtain a desired plasma concentration, the drug is administered for a duration of therapeutic regimens in excess of 6 months.

The administration of composition of the invention may result in a plasma concentration ranging from about 500 ng/ml to 5000 ng/ml; from about 800 ng/ml to 2500 ng/ml, or from about 1400 ng/ml to 1800 ng/ml.

The pharmaceutical compositions of the invention may be formulated in a variety of ways, including for example, solid, semi-solid, and liquid dosage forms, such as capsules, tablets, pills, powders, liquid solutions (e.g., injectable and infusible solutions), dispersions or suspensions, liposomes and suppositories. In some embodiments, the compositions are in the form of injectable or infusible solutions. The composition is in a form suitable for oral, topical, intravenous, intraarterial, intramuscular, subcutaneous, parenteral, transmucosal, or transdermal administration.

In a particular embodiment, the composition is in the form of a capsule. In another particular embodiment, the composition is in the form of a tablet.

Administration of the pharmaceutical composition can be through various routes, including orally, nasally, subcutaneously, intravenously, intramuscularly, transdermally, vaginally, rectally or in any combination thereof. Transdermal administration can be effected using, for example, oleic acid, 1-methyl-2-pyrrolidone, dodecylnonaoxyethylene.

In one aspect, the invention provides administering to a subject a therapeutically effective amount of a first tyrosine hydroxylase inhibitor, for example, α-methyl-DL-tyrosine in combination with a therapeutically effective amount of a second tyrosine hydroxylase inhibitor, for example, α-methyl-L-tyrosine. In another aspect, the invention provides administering to a subject a therapeutically effective amount of one or more tyrosine hydroxylase inhibitors, for example, α-methyl-DL-tyrosine and/or α-methyl-L-tyrosine in combination with a therapeutically effective amount of another agent useful in the treatment of autism.

In some of these aspects, 7-aminobutyric acid (GABA) can be administered with the tyrosine hydroxylase inhibitor (e.g., α-methyl-DL-tyrosine). The GABA can be administered simultaneously with the tyrosine hydroxylase inhibitor. In other aspects, the GABA can be administered separately from the tyrosine hydroxylase inhibitor, e.g., at another time during the day. In some aspects the GABA is administered at bedtime. Typically, dosages of the GABA are from about 5 mg to about 30 mg, for example, 5, 10, 15, 20, 25, or about 30 mg of GABA, with 15 mg of GABA being particularly preferred.

In other of these aspects, a p450 3A4 promoter is administered in addition to the tyrosine hydroxylase inhibitor (e.g., α-methyl-DL-tyrosine) and the optional GABA. Preferred p450 3A4 promoters include 5,5-diphenylhydantoin, valproic acid, and carbamazepine.

Those subjects on the autism spectrum, including those diagnosed with Asperger's Disorder (Asperger Syndrome) or Social Communication Disorder, who also have symptoms of ADHD and/or tics can be treated using methods of the disclosure. In these aspects, the subject can be administered an effective amount of a tyrosine hydroxylase inhibitor and an effective amount of a beta adrenergic agonist (also referred to as beta agonists). The tyrosine hydroxylase inhibitor can be any of the tyrosine hydroxylase inhibitors described herein, with α-methyl-DL-tyrosine being particularly preferred. Beta adrenergic agonists are known in the art and include, for example, albuterol, levalbuterol, fenoterol, formoterol, isoproterenol, metaproterenol, salmeterol, terbutaline, clenbuterol, isoetarine, pirbuterol, procaterol, ritodrine, epinephrine, and combinations thereof. Albuterol is a particularly preferred beta adrenergic agonist.

In certain of these aspects, the tyrosine hydroxylase inhibitor and the beta adrenergic inhibitor are administered simultaneously. In other aspects, the beta adrenergic inhibitor is administered separately from the α-methyl-DL-tyrosine, e.g., at another time during the day.

According to the disclosure, the described methods for treating a disease or disorder can be used in combination with treatment methods that are also known to be effective in treating the same disease or disorder. For example, autism behaviors and symptoms can be treated with compounds that affect autonomic neurotransmission (e.g. amphetamine, methylphenidate, and the like), psychotopic drugs (e.g., risperidone), neutotransmitter reuptake inhibitors (e.g., fluoxetine), compounds that stimulate glutaminergic transmission (e.g., LY2140023), and/or compounds that affect cholinergic neurotransmission (e.g., galantamine). As such, the disclosure is also directed to methods of treating autism in a patient by administering an effective amount of a tyrosine hydroxylase inhibitor (e.g., α-methyl-DL-tyrosine) and an effective amount of a compound that affects autonomic neurotransmission, a psychotopic drug, a neutotransmitter reuptake inhibitor, a compound that stimulates glutaminergic transmission, and/or a compound that affects cholinergic neurotransmission. In one embodiment, the invention provides methods of treating autism in a patient by administering a therapeutically effective amount of a tyrosine hydroxylase inhibitor (e.g., α-methyl-DL-tyrosine) and a therapeutically effective amount of a central nervous system (CNS) agent.

The diseases or disorders treated by the composition of the invention include, for example, autism or its associated disease or disorder.

The autonomic nervous system has been implicated in symptoms that resemble those seen in autism. Autism spectrum disorder (ASD) has been associated with abnormal findings in autonomic related structures including the insula and the amygdala. Autonomic related changes such as increases in basal heart rate and diminished heart rate due to psychosocial challenges are seen in autism. The autism-autonomic linkage is exemplified by the consequences of respiratory sinus arrhythmia (RSA) that includes difficulties with socialization, language difficulties, and delays in cognitive development.

It has been hypothesized a chronically over activated autonomic system is a correlate of autism based upon the exaggerated levels of anxiety that attend autism, physiologic hyperarousal, and other correlates. Anxiety, perhaps the greatest co-morbidity associated with autism and which may drive other features of the disease, has been associated with central nervous system structures that are linked to autonomic function. Phenotypically autism and anxiety both present with stereotyped repetitive behaviors and limited interests, avoidance behaviors, and speech problems.

The relationship between anxiety and reported autonomic symptoms of elevated heart rate, perspiration, and other sequelae of the "fight or flight" reaction reveal a role for the peripheral nervous system function in autism. However, this may be secondary to central autonomic activation. Central functions may manifest as elevated emotional responsiveness and exaggerated threat perception or diminished inhibition of fear responses, which are associated with the central structures mentioned above in which autonomic responsiveness and emotional responsiveness overlap.

There is a considerable body of evidence that associates autism with cholinergic function in the central nervous system, specifically with various α-subtype nicotinic receptors, notably in the cerebellum. However, as autonomic function is classically considered to be a balance of cholinergic and catecholaminergic systems, perceived increases or decreases in cholinergic function may be manifestations of change in the dynamic balance of these systems with catecholaminergic tone. It is believed that it may be possible to effect therapeutic change in ASD through manipulation of either acetylcholine based manipulations or the counterbalancing of dopamine, norepinephrine, or epinephrine mediated mechanisms by administration of α-methyl-DL-tyrosine.

The present invention also relates to the treatment of the core symptoms of ASD by administration of α-methyl-DL-tyrosine to subjects in need thereof.

While not intending to be bound by any particular mechanism of operation, it is believed that the tyrosine hydroxylase inhibitor (e.g., α-methyl-DL-tyrosine) administered according to the present invention modulates the catecholaminergic pathways implicated in autism, more specifically such pathways involved in the core symptoms of ASD, including the catecholaminergic functions in the CNS and in the gastrointestinal tract. Therefore, the known effects of catecholamines on the endocrine and neuroendocrine systems are regulated by administration of the tyrosine hydroxylase inhibitor (e.g., α-methyl-DL-tyrosine), including but not limited to decreasing the amount of adrenaline secreted into the bloodstream, which may lessen the intensity of irritability and agitation, and other core symptoms of ASD.

In one aspect, the invention provides a method for treating core symptoms of Autism Spectrum Disorder (ASD) in a subject in need thereof, the method comprising administering a therapeutically effective amount of a racemic mixture of α-methyl-DL-tyrosine.

In another aspect, the invention provides a method for treating an autism associated clinical trait in a subject in need thereof, the method comprising administering to said subject a composition comprising a therapeutically effective amount of a tyrosine hydroxylase inhibitor (e.g., α-methyl-DL-tyrosine), thereby treating said autism associated clinical trait in said subject.

Examples of an autism associated clinical trait include, for example, but not limited to, a lack of social communication, a lack of social interaction, a lack of social motivation, lethargy and social withdrawal, inappropriate speech, hyperactivity, stereotypic behavior, irritability and agitation, restrictive behavior, repetitive behavior, ritualistic behavior, sameness behavior, compulsive behavior, self-injurious behavior or a combination thereof.

In one embodiment, the clinical trait is assessed based upon a change from a baseline in one or more psychometric tests. Examples of a psychometric test include, for example, but not limited to, clinical global impression (CGI) rating scale, Vineland adoptive behavior scale (VABS), autism diagnostic observation schedule (ADOS), social responsiveness scale (SRS), aberrant behavior checklist-community (ABC-C), repetitive behavior scale (RBS), Conners parent rating scale (CPRS), or a combination thereof. In a particular embodiment, the clinical trait meets the requirements of Diagnostic and Statistical Manual of Mental Disorders-V (DSM-V) criteria.

The terms "subject," "individual," and "patient" are used interchangeably herein, and refer to an animal, for example a human, to whom treatment, including prophylactic treatment, with the pharmaceutical composition according to the present invention, is provided. The term "subject" as used herein refers to human and non-human animals. The terms "non-human animals" and "non-human mammals" are used interchangeably herein and include all vertebrates, e.g., mammals, such as non-human primates, (particularly higher primates), sheep, dog, rodent, (e.g. mouse or rat), guinea pig, goat, pig, cat, rabbits, cows, horses and non-mammals such as reptiles, amphibians, chickens, and turkeys.

In one embodiment, the subject is a human patient between 3 years of age and 21 years of age; 5 years of age and 21 years of age; or 6 years of age and 17 years of age. In another embodiment, the subject is an adult human patient.

All patents and literature references cited in the present specification are hereby incorporated by reference in their entirety.

Also provided herein are kits comprising one or more molecules or compositions described herein. The following examples are provided to supplement the prior disclosure and to provide a better understanding of the subject matter described herein. These examples should not be considered to limit the described subject matter. It is understood that the examples and embodiments described herein are for illustrative purposes only and that various modifications or changes in light thereof will be apparent to persons skilled in the art and are to be included within, and can be made without departing from, the true scope of the invention.

EXAMPLES

Example 1

Two-hundred patients were initially screened. Thirty subjects meeting the study criteria consented. Nine (9) subjects had high blood glucose levels (hyperglycemia) prior to consenting to the study.

A high blood glucose level (hyperglycemia) is defined as a fasting plasma blood glucose level of 126 mg/dl or greater on two separate occasions. The average patient age was sixty-two years old and the median patient age was sixty years old. Six of the patients were female and three of the patients were male. Five of the patients were fifty to sixty years old and four of the patients were over the age of sixty.

The patients in the study were administered a treatment regimen that included a tyrosine hydroxylase inhibitor (i.e., α-methyl-DL tyrosine), a melanin promoter (i.e., melanotan II), a p450 3A4 promoter (i.e., 5,5-diphenylhydantoin), and a leucine aminopeptidase inhibitor (i.e., N-[(2S,3R)-3-amino-2-hydroxy-4-phenylbutyryl]-L-leucine). These compounds were administered on each of five days per week for a period of six weeks, with one or two days off between weekly cycles. Blood glucose level was monitored for all subjects biweekly. Blood glucose levels were determined by daily blood glucose tests followed-up with laboratory blood glucose tests every two weeks.

After approximately two to four weeks, all nine of the subjects had normal blood glucose levels defined as a fasting plasma blood glucose level of 125 mg/dl or lower on two separate occasions.

Overall, the above-noted treatment was well tolerated by the subjects, with no adverse events related to the treatment, and responses have been documented to the treatment 100%.

Example 2

Patients are screened and the extent to which they meet the DSM-V criteria for autism spectrum disorder is assessed. A subgroup of those satisfying the criteria are administered a treatment regimen that includes a tyrosine hydroxylase inhibitor (i.e., α-methyl-DL tyrosine) at dose of 50-100 mg three times daily. Another subgroup is administered a treatment regimen that further includes a p450 3A4 promoter (i.e., 5,5-diphenylhydantoin) in one daily dose of 30 mg.

Gamma-aminobutyric acid is optionally administered to both subgroups at bedtime at a dose of 15 mg to aid sleeping and to quiet ticks and repetitive behaviors like teeth grinding. Vasopressin is administered as needed to assist brain governance. Following each administration of the treatment regimen, changes in the extent to which the subjects satisfy the DSM-5 criteria is again assessed.

Example 3

A Blinded, Randomized, Placebo Controlled Phase 2 Study for the Use of AMPT in the Treatment of Autism Study Design: Blinded, randomized, 2 arm, 8-week treatment period followed by additional follow-up visits off treatment over the next 18 weeks for a total of 26 weeks' study participation. Treatment arms consist of L1-79 alone or placebo.

Sample Size: L1-79 N=30, placebo N=10

Study Population: Autistic patients over 12 years of age that meet the entry criteria and who are high performing in the opinion of the investigator.

Major Inclusion Criteria: Signed informed consent, normal clinical laboratory values, DSM-5 compliant diagnosis of autism, Qualifying ADOS score, sufficiently high functioning to complete the protocol, no psychotropic drugs for at least 2 weeks, ABC-C score >12.

Major Exclusion Criteria: Fragile-X syndrome, epilepsy, use of complimentary alternative medications, any co-morbidities, other psychiatric disorder, out of range lab values.

Experimental Treatment: L1-79 is a racemic form of the drug Demser®. It will be given daily×8 weeks, and then followed on weeks 10, 13 and 26.

Non-Experimental Treatment: Placebo.

Dosage and Administration: LI-79 or placebo, as randomized, will be administered orally at a dose of 90 mg TID.

Evaluation Schedule: Patients will receive 8 weeks of the schedule above with weekly treatment evaluations for weeks 1-8 then post-treatment follow up visits at weeks 10, 13 & 26.

Safety Measures: Regularly scheduled complete history and physical examination, vital signs, CBC, differential, platelet counts, urine analysis, serum enzymes including: total protein, albumin, glucose, BUN, creatinine, direct and total bilirubin, alkaline phosphatase, phosphorous, calcium, aspartate aminotransferase ("AST"), alanine aminotransferase ("ALT"), sodium, potassium, chloride, bicarbonate, $T_4$, TSH, and adverse events assessments. An independent DMC will oversee the conduct of this trial to assure patient safety.

Study Duration: A maximum of 50 weeks (12 weeks' enrollment, 38 weeks' treatment and follow-up).

Study Endpoints: The primary end point will be the assessment of the attending physician as reflected in the Clinical Global Impressions (CGI) scale based upon changes from baseline in various psychometric tests, including the Aberrant Behavior Checklist-Community (ABC-C), Conners Parent Rating Scale and the Autism Diagnostic Observation Schedule (ADOS), as well as from their personal observations in the clinic, and from videographic information taken at regularly scheduled clinic visits (per this protocol) and provided by caregivers over the course of this study.

Example 4

α-methyl-DL tyrosine (AMPT) was administered to 3 patients. This group of patients was qualified under the DSM-5 definition of autism and treated. See Table 1.

TABLE 1

| Patient number | Age | Sex | Dosage AMPT | Adverse Events |
|---|---|---|---|---|
| 01-001 | 3 | Male | 90 TID | None |
| 01-002 | 15 | Male | 90 TID | None |
| 01-003 | 11 | Male | 90 TID | None |

The Aberrant Behavior Checklist-Community (ABC-C), Autism Diagnostic Observation Schedule (ADOS), Conners Parent Rating Scale (CPRS), and General Clinical Impressions scale were used to assess the disease. Videos were taken at each visit.

Data for two of these patients over the first 3 weeks of this observation are presented in the tables below. Conners Patent Rating Scale Data is depicted in FIG. 1. These clinical improvements appear to begin quickly and are durable. Continued improvement over weeks and months has been observed. No adverse events have been reported other than mild tiredness on the first day of dosing in two patients.

TABLE 2

PT LR

| Test | Dimension | initial | Day 7 | Day 14 | Day 21 | Day 28 |
|---|---|---|---|---|---|---|
| ABC-C | TOTAL | 114 | 71 | 55 | 53 | 53 |
|  | irritability | 21 | 16 | 16 | 16 | 16 |
|  | lethargy | 31 | 12 | 8 | 7 | 7 |
|  | stereotypy | 13 | 5 | 0 | 0 | 0 |
|  | hyperactivity | 34 | 31 | 24 | 23 | 23 |
|  | speech | 5 | 7 | 7 | 7 | 7 |
| DSM-V | TOTAL | 42 | 27 | 21 | 18 | 18 |
|  | social | 9 | 5 | 3 | 2 | 2 |
|  | communication | 10 | 4 | 3 | 2 | 2 |
|  | relationships | 11 | 4 | 3 | 2 | 2 |
|  | behavior | 12 | 12 | 12 | 12 | 12 |

TABLE 3

PT RS

| Test | Dimension | initial | Day 7 | Day 14 | Day 21 | Day 28 |
|---|---|---|---|---|---|---|
| ABC | TOTAL | 53 | 28 | 20 | 20 | 20 |
|  | irritability | 3 | 3 | 1 | 1 | 1 |
|  | lethargy | 6 | 3 | 1 | 1 | 1 |
|  | stereotypy | 16 | 11 | 9 | 9 | 9 |
|  | hyperactivity | 20 | 8 | 6 | 6 | 6 |
|  | speech | 8 | 3 | 3 | 3 | 3 |
| DSM V | TOTAL | 21 | 15 | 8 | 6.5 | 5.5 |
|  | social | 5 | 3 | 1.5 | 1 | 1 |
|  | communication | 5 | 4 | 1.5 | 1.5 | 1.5 |
|  | relationships | 1 | 0 | 0 | 0 | 0 |
|  | behavior | 10 | 8 | 5 | 4 | 3 |

TABLE 4

PT WC

| Test | Dimension | initial | Day 7 | Day 14 | Day 21 | Day28 |
|---|---|---|---|---|---|---|
| ABC-C | TOTAL | 70 | 30 | 18 | 17 | 17 |
|  | irritability | 16 | 4 | 2 | 2 | 2 |
|  | lethargy | 21 | 9 | 3 | 2 | 2 |
|  | stereotypy | 12 | 7 | 6 | 6 | 6 |
|  | hyperactivity | 20 | 10 | 7 | 7 | 7 |
|  | speech | 1 | 0 | 0 | 0 | 0 |
| DSM-V | TOTAL | 26 | 17 | 14 | 12 | 11 |
|  | social | 6 | 6 | 4 | 2 | 2 |
|  | communication | 3 | 0 | 0 | 0 | 0 |
|  | relationships | 6 | 2 | 2 | 2 | 2 |
|  | behavior | 11 | 9 | 8 | 8 | 7 |

Example 5

Evaluation of L1-79 Administration in Patients with Autism

L1-79 was used anecdotally in two patients followed by a more structured evaluation in 8 additional patients with autism. All patients were administered a starting dose of L1-79 of 90 mg TID for a minimum of 3 months. During the evaluation doses as high as 400 mg TID were used. A summary of data available on these 10 patients was provided in the Summary of Clinical Efficacy, Use of L1-79 to treat autism, submitted to IND 128673, sequence number 0005. While the sample size was small and involved open-label administration of L1-79, the results were encouraging with consistent improvements in the ABC-C domains and an average reduction in the ADOS-2 of 30%, and one child manifesting an ADOS-2 decrease of 60% which resulted in the loss of his autism diagnosis. In addition, longer treatment resulted in a greater magnitude of therapeutic benefits on the core symptoms of autism. Moreover, when the study drug, L1-79, was discontinued not all of the benefits regressed. These data suggest that L1-79 has the potential to improve the core symptoms of autism.

Example 6

A Randomized, Double-Blind Placebo-Controlled 4-week Study in Male Patients Diagnosed with Autism The purpose of this clinical study (referred to herein as "Study HT 02-121"; i.e., Example 6) was to determine whether L1-79 was a well-tolerated and clinically useful agent for the treatment of ASD, and to assess the PK and pharmacodynamics (PD) of four weeks of TID dosing with L1-79. While the preliminary study of Example 5 involved open-label treatment with L1-79 for at least three months, the present study was only 4-weeks based upon limitations in the available toxicology data. Based on the shorter duration, the response to L1-79 was expected to be less in Study HT 02-121 compared to the preliminary study of longer duration.

This clinical study was a randomized double-blind, placebo-controlled two-cohort, 4-week dose-escalation study that incorporated two open-label treatment groups to assess the safety and efficacy of L1-79 100 mg and 200 mg TID in male patients between the ages of 12-21 years of age diagnosed with autism. The first cohort of 20 patients was comprised of three groups of patients: The first group of five patients received open-label L1-79 100 mg TID and underwent PK and EKG assessments. The remaining two groups in this cohort consisted of 15 patients randomized on a 2:1 basis to receive L1-79 100 mg TID or placebo. The PK and safety data from the open-label L1-79 100 mg TID group was submitted to FDA for review and acceptance before the second cohort was enrolled. The second cohort was procedurally identical to the first. The second cohort of 20 patients was comprised of the same three groups of patients but a dose of 200 mg TID was used instead of 100 mg TID. The key inclusion criteria were as follows: (1) males between 13 and 21 years of age, (2) DSM-5 compliant diagnosis of autism spectrum disorder, confirmed by the Autistic Diagnosis Interview Review (ADIR), and by an ADOS-2 score consistent with a diagnosis of autism, (3) must have been stable on no more than one concomitant medication and no planned changes in psychosocial interventions during the study.

The key exclusion criteria were as follows: (1) sexually active males, (2) a history of Fragile-X syndrome, Rett syndrome or any other co-morbidity including but not limited to cancer, genetic diseases, or any disease or syndrome that required drug therapy, (3) DSM-5 diagnosis of schizophrenia, schizoaffective disorder, alcohol use disorder or attention deficit hyperactivity disorder (ADHD), (4) had any active medical problem(s), including epilepsy and asthma, (5) uncontrolled intercurrent illness including, but not limited to, ongoing or active infection, symptomatic cardio-vascular disease, hepatic disease, renal disease, skeleto-muscular disease, human immunodeficiency virus (HIV), hemorrhagic cerebrovascular accident (HCVA), hepatitis B virus (HBV), or psychiatric illness/social situations that would limit compliance with study requirements, (6) any disease that required chronic treatment, (7) any disease that required treatment with an immunosuppressive drug, and/or (8) current or lifetime diagnosis of severe psychiatric disorder.

Open-Label Patients

The first five patients in each cohort were assigned to receive active medication in an open-label fashion. The patients were treated identically to the randomized patients with the following exceptions: (1) blood samples were drawn at baseline and 1 hour after dosing, and at Week 1, 2, 3 and 4 treatment visits 1 hour after dosing to determine the PK of L1-79, (2) EKGs were assessed at baseline and within 3-days prior to the Week 1, 2, 3 and 4 treatment visits as well as the 1-week and 4-week post-dosing follow-up visits, (3) vital signs, physical exams, and ASD assessments were performed at 1-week postdosing visit, (4) blood and urine samples were drawn at baseline and at Week 1, 2, 3 and 4 treatment visits 1 hour after dosing as well as the 1-week and 4-week post-dosing follow-up visits for safety analyses.

Randomized Patients

The randomized patients were treated identically to the open-label patients with the following three exceptions: (1) no blood samples for PK were drawn, (2) no ECG was performed, and (3) these patients did not have a 1-week follow-up visit, only a 4-week follow-up visit. A time and events schedule for the study is provided below in Table 5.

TABLE 5

Time and Events Schedule

| Form # | Form Name | Screening | Wk 0 Baseline | Wk 1 | Wk 2 | Wk 3 | Wk 4 | 1 Wk Post Dosing | 4 Wk FUP |
|---|---|---|---|---|---|---|---|---|---|
| | Study Day | | 0 ± 2 | 7 ± 2 | 14 ± 2 | 21 ± 2 | 28 ± 2 | 35 ± 2 | 56 ± 2 |
| 1 | Date of Visit | x | x | x | x | x | x | x | x |
| 2 | Informed Consent & Study Compliance | x | | | | | | | |
| 3 | Demography | x | | | | | | | |
| 4 | Additional Patient Information | x | | | | | | | |
| 5 | Inclusion Criteria | x | | | | | | | |
| 6 | Exclusion Criteria | x | | | | | | | |
| 7 | Eligibility Criteria | x | | | | | | | |
| 8 | Medical History | x | | | | | | | |
| 9 | Family History | x | | | | | | | |
| 10 | Lab - Hematology (All Patients) | x | | | | | x | | x |
| 11 | Lab - Serum Chemistry (All Patents) | x | | | | | x | | x |
| 12 | Urine Analysis (All Patients) | x | | | | | x | | x |
| 13 | Lab - Hematology (Assigned Patients Only) | | x* | x | x | x | x | x** | x |
| 14 | Lab - Serum Chemistry (Assigned Patients Only) | | x* | x | x | x | x | x** | x |
| 15 | Urine Analysis (Assigned Patients Only) | | x* | x | x | x | x | x** | x |

TABLE 5-continued

Time and Events Schedule

| Form # | Form Name | Screening | Wk 0 Baseline | Wk 1 | Wk 2 | Wk 3 | Wk 4 | 1 Wk Post Dosing | 4 Wk FUP |
|---|---|---|---|---|---|---|---|---|---|
| 16 | PK/PD | | x* | x | x | x | x | | |
| 17 | Blood Draw | x | | | | | x | x** | x |
| 18 | Vital Signs - Screening | x | | | | | | | |
| 19 | Vital Signs | | x | x | x | x | x | x** | x |
| 20 | Physical Examination | x | | | | | | x** | x |
| 21 | Randomization | | x | | | | | | |
| 22 | ADOS | x | | | | | x | | |
| 23 | EKG (Assigned Patients Only) | | x | x | x | x | x | x** | x |
| 24 | ADI-R (Telephonic) | x | | | | | | | |
| 25 | SAS | | x | | | | | x** | x |
| 26 | VABS II | | x | | | | x | x** | x |
| 27 | ABC-C |All Scales| | | x | x | x | x | x | x** | x |
| 28 | SRS | | x | x | x | x | x | x** | x |
| 29 | RBS-R | | x | x | x | x | x | x** | x |
| 30 | CGI-S | | x | x | x | x | x | x** | x |
| 31 | CGI-I | | | x | x | x | x | x** | x |
| 32 | CGI-Overall Score | | x | x | x | x | x | x** | x |
| 33 | Study Drug Dispensing | | x | | x | | | | |
| 34 | Study Drug Administration | | | x | x | x | x | | |
| 35 | Drug Accountability | | | | x | | x | | |
| 36 | Adverse Event | | x | x | x | x | x | x** | x |
| 37 | Prior and Concomitant Medication | x | x | x | x | x | x | x** | x |

*At baseline visit for Assigned Group Patients PK samples are to be taken before, and 1 hour after, the $1^{st}$ dose.
**Assigned Group Patients Only Safety Endpoints Safety was the primary endpoint of the study. The following safety endpoints were assessed: ECGs, physical exams, laboratory evaluations (hematology, chemistry and urinalysis), vital signs, including orthostatic blood pressure, adverse events (AEs) and concomitant medications.

Efficacy Endpoints

The primary efficacy endpoint was the determination of the clinical improvement by the investigator as documented by the Clinical Global Impression (CGI) rating scales. Additional efficacy endpoints included: (1) changes from baseline in the Socialization and Communication Domains of the Vineland Adaptive Behavior Scales, Second Edition (VABS II) parent/caregiver rating form, (2) changes from baseline in the ADOS-2 Total Score and subscores, (3) changes in the Social Responsiveness Scale, Second Edition (SRS-2) Total Score and subscales, (4) changes in the ABC-C domains, (5) changes in the Repetitive Behavior Scale-Revised (RBS-R) Total Score and subscales. Given the exploratory design of this study only descriptive statistics were planned.

Results

Study Population

Figure 2:
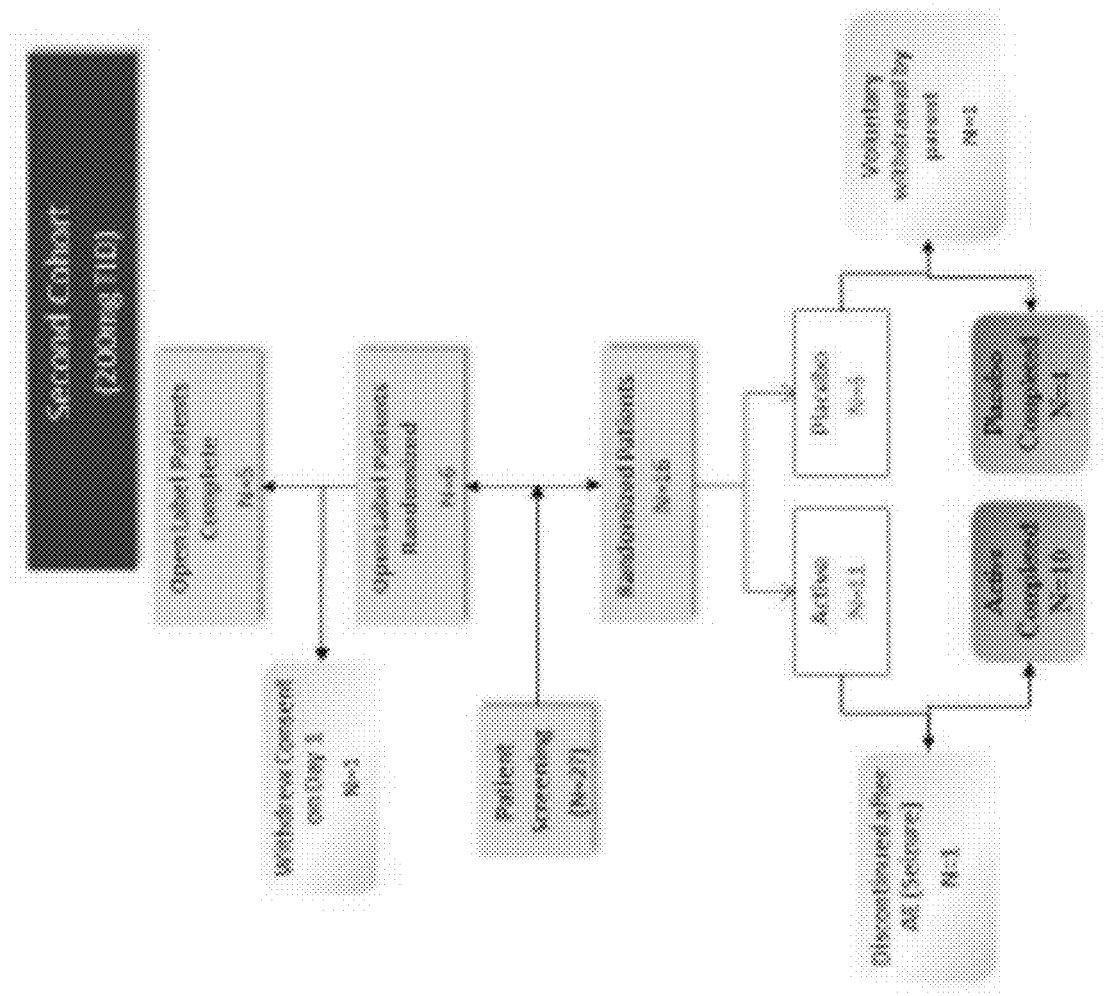
FIG. 2 illustrates patient enrollment and disposition.
Figure 2:
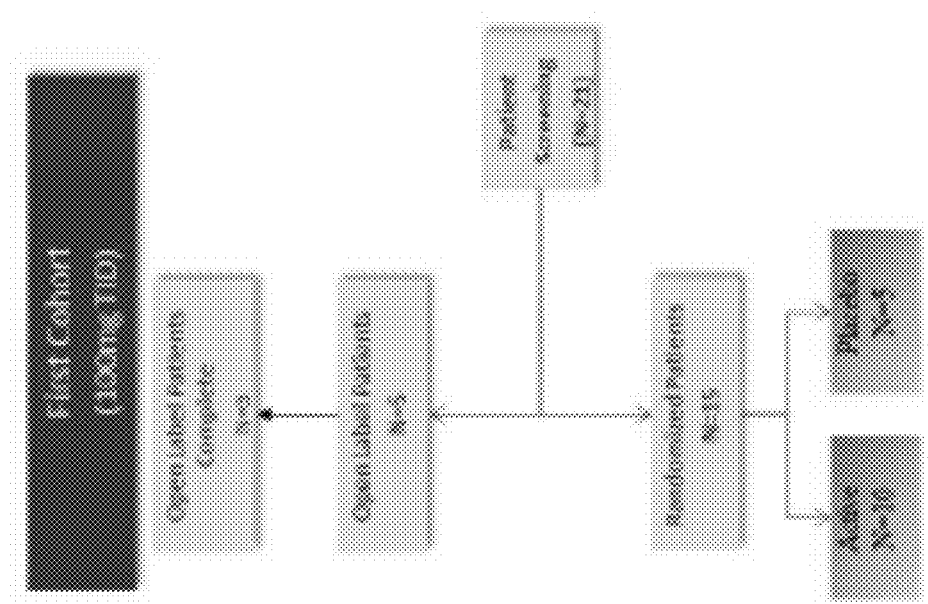

Patient enrollment and disposition are summarized in FIG. 2. A total of 42 patients were randomized and received at least one dose of study drug. One patient was randomized to open-label L1-79 200 mg TID but the parent requested voluntary withdrawal from the study at Week 0/Baseline after receiving a single dose of study medication in clinic. Thirty-nine patients completed the study. One patient treated with double-blind L1-79 200 mg TID withdrew from the study due to an AE (see Table 8) and one patient treated with placebo voluntarily withdrew from the study. Demographic characteristics are summarized in Table 6.

TABLE 6

Demographic Characteristics

| | L1-79 100 mg TID | | L1-79 200 mg TID | | Placebo |
|---|---|---|---|---|---|
| | Open label N = 5 | Double-blind N = $10^2$ | Open label N = $5^1$ | Double blind N = 11 | N = $10^2$ |
| Age (years) | | | | | |
| Mean (SD) | 16.2 (2.9) | 16.4 (2.2) | 16.4 (1.1) | 16.4 (2.7) | 15.8 (2.7) |
| Range (min, max) | 13, 19 | 13, 20 | 15, 18 | 12, 20 | 12, 19 |
| Sex, n (%) | | | | | |
| Male | 5 (100) | 10 (100) | 5 (100) | 11 (100) | 10 (100) |

TABLE 6-continued

| Demographic Characteristics | | | | | |
|---|---|---|---|---|---|
| | L1-79 100 mg TID | | L1-79 200 mg TID | | |
| | Open label N = 5 | Double-blind N = 10[2] | Open label N = 5[1] | Double blind N = 11 | Placebo N = 10[2] |
| Race, n (%) | | | | | |
| Caucasian | 4 (80) | 10 (100) | 4 (80) | 9 (82) | 7 (70) |
| African American | 0 | 0 | 1 (20) | 0 | 2 (20) |
| Other | 1 (20) | 0 | 0 | 2 (18) | 1 (10) |

[1] One patient was randomized to open-label L1-79 200 mg TID and only received a single dose of study medication. Data from this patient are not included in the table.
[2] There was apparent confusion in the assigned-vs.-received drug kit numbers for two consecutively enrolled patients at site 01 who were randomized on the same day (subjects 01-008-01-009). Since there is sufficient uncertainty about what treatment the two patients actually received, data was analyzed conservatively by omitting these two patients from the efficacy analyses. Data from these two patients were included in the study population and safety analyses (however, neither subject had reported AEs.).

Safety

Concomitant Medications and Physical Exams

The majority of patients were not on CNS medications during the study. The following CNS medications were used during the study: clonidine (n=2), Strattera® (n=1), Depakote® (n=3), lorazepam (n=1), Prozac® (n=1), and Abilify® (n=1). There were no clinical significant physical exam findings reported during the study.

Adverse Events

The incidence of AEs by primary system organ class and preferred term is presented in Table 7, and a listing of the AEs reported during the study is presented in Table 8. All AEs were mild to moderate in intensity and self-limited.

TABLE 7

| Incidence of Adverse Events by Primary System Organ Class and Preferred Term | | | | | |
|---|---|---|---|---|---|
| | L1-79 100 mg TID | | L1-79 200 mg TID | | |
| Primary SOC Preferred Term | Open label N = 5 n (%) [e] (%) | Double-blind N = 10 n (%) [e] (%) | Open label N = 6 n (%) [e] (%) | Double blind N = 11 n (%) [e] (%) | Placebo N = 10 n (%) [e] (%) |
| All primary SOC | 2(40.0)[6](100) | 1(10.0)[1](100) | 2(40.0)[4](100) | 6(54.5)[10](100) | 3(30.0)[6](100) |
| GI disorders | 0[0] | 0[0] | 0[0] | 3(27.3)[3](30.0) | 0[0] |
| Diarrhoea | 0[0] | 0[0] | 0[0] | 3(27.3)[3](30.0) | 0[0] |
| General disorders & administration site conditions | 0[0] | 0[0] | 2(40.0)[2](50) | 0[0] | 0[0] |
| Fatigue | 0[0] | 0[0] | 1(20.0)[1](25.0) | 0[0] | 0[0] |
| Pyrexia | 0[0] | 0[0] | 1(20.0)[1](25.0) | 0[0] | 0[0] |
| Immune system disorders | 0[0] | 0[0] | 1(20.0)[1](25.0) | 0[0] | 0[0] |
| Seasonal allergy | 0[0] | 0[0] | 1(20.0)[1](25.0) | 0[0] | 0[0] |
| Infections and Infestations | 0[0] | 0[0] | 0[0] | 2(18.2)[2](20.0) | 1(10.0)[1](16.7) |
| Ear infection | 0[0] | 0[0] | 0[0] | 1(9.1)[1](10.0) | 0[0] |
| Nasopharyngifs | 0[0] | 0[0] | 0[0] | 0[0] | 1(10.0)[1](16.7) |
| Otitis externa | 0[0] | 0[0] | 0[0] | 1(9.1)[1](10.0) | 0[0] |
| Investigations | 0[0] | 0[0] | 0[0] | 3(27.3)[3](30.0) | 0[0] |
| Amylase ↑ | 0[0] | 0[0] | 0[0] | 0[0] | 1(10.0)[1](16.7) |
| Blood TSH ↑ | 0[0] | 0[0] | 0[0] | 1(9.1)[1](10.0) | 0[0] |
| Crystal urine present | 0[0] | 0[0] | 0[0] | 2(18.2)[2](20.0) | 0[0] |
| Nervous system disorders | 0[0] | 1(10.0)[1](100) | 0[0] | 1(9.1)[1](10.0) | 0[0] |
| Generalised tonic-cloric seizure | 0[0] | 0[0] | 0[0] | 1(9.1)[1](10.0) | 0[0] |
| Syncope | 0[0] | 1(10.0)[1](100) | 0[0] | 0[0] | 0[0] |
| Psychiatric disorders | 2(40.0)[6](100) | 0[0] | 0[0] | 1(9.1)[1](10.0) | 1(10.0)[2](33.3) |
| Agitation | 0[0] | 0[0] | 0[0] | 0[0] | 1(10.0)[1](16.7) |
| Anxiety | 1(20.0)[1](16.7) | 0[0] | 0[0] | 1(9.1)[1](10.0) | 0[0] |
| Confusional state | 1(20.0)[1](16.7) | 0[0] | 0[0] | 0[0] | 0[0] |
| Intentional self-injury | 2(40.0)[2](33.3) | 0[0] | 0[0] | 0[0] | 1(10.0)[1](16.7) |
| Irritability | 2(40.0)[2](33.3) | 0[0] | 0[0] | 0[0] | 0[0] |
| Renal and urinary disorders | 0[0] | 0[0] | 0[0] | 0[0] | 1(10.0)[2](33.3) |

TABLE 7-continued

Incidence of Adverse Events by Primary System Organ Class and Preferred Term

| | L1-79 100 mg TID | | L1-79 200 mg TID | | Placebo |
| | Open label | Double-blind | Open label | Double blind | |
| Primary SOC | N = 5 | N = 10 | N = 6 | N = 11 | N = 10 |
| Preferred Term | n (%) [e] (%) | n (%) [e] (%) | n (%) [e] (%) | n (%) [e] (%) | n (%) [e] (%) |
|---|---|---|---|---|---|
| Urinary incontinence | 0[0] | 0[0] | 0[0] | 0[0] | 1(10.0)[2](33.3) |
| Respiratory, thoracic & mediastinal disorders | 0[0] | 0[0] | 1(20.0)[1](25.0) | 0[0] | 0[0] |
| Cough | 0[0] | 0[0] | 1(20.0)[1](25.0) | 0[0] | 0[0] |

TABLE 8

Listing of Adverse Events

| Patient ID | Treatment | AE Verbatim Term (Preferred Term) | Severity | Treatment Emergent | Relationship | Outcome | Discontinued |
|---|---|---|---|---|---|---|---|
| 02-009 | DB 100 mg TID | syncope (syncope) | mild | Y | not related | resolved | N |
| 01-014 | DB 200 mg TID | crystal urine present (urine cystine crystal present) | mild | N[1] | not related | resolved | N |
| 01-016 | DB 200 mg TID | diarrhoea (diarrhea) | moderate | Y | not related | resolved | N |
| 01-018 | DB 200 mg TID | crystal urine present (urine cystine crystal present) | mild | N[1] | not related | resolved | N |
| 02-018 | DB 200 mg TID | anxiety (anxious mood) | mild | Y | possibly related | resolved | N |
| 02-018 | DB 200 mg TID | otitis externa (otitis externa) | mild | Y | not related | resolved | N |
| 02-018 | DB 200 mg TID | diarrhoea (diarrhea) | moderate | Y | possibly related | resolved | N |
| 02-018 | DB 200 mg TID | blood thyroid stimulating hormone increased (elevated TSH) | moderate | N[1] | possibly related | resolved | N |
| 02-023 | DB 200 mg TID | generalized tonic-clonic seizer (grand mal seizure) | moderate | Y | possibly related | resolved | Y |
| 02-024 | DB 200 mg TID | ear infection (earl infection) | mild | N[2] | not related | resolving | N |
| 02-024 | DB 200 mg TID | diarrhoea (diarrhea) | mild | Y | not related | resolved | N |
| 01-017 | DB Placebo TID | amylase increased (elevated amylase) | mild | N[2] | not related | resolved | N |
| 02-017 | DB Placebo TID | urinary incontinence (bladder incontinence) | mild | Y | possibly related | resolved | N |
| 02-017 | DB Placebo TID | urinary incontinence (bladder incontinence) | mild | Y | possibly related | resolved | N |
| 02-017 | DB Placebo TID | nasopharyngitis (common cold) | mild | Y | not related | resolved | N |
| 02-019 | DB Placebo TID | intentional self-injury (self injurious behavior) | mild | Y | possibly related | unknown | N |
| 02-019 | DB Placebo TID | agitation (agitation) | mild | Y | possibly related | unknown | N |
| 02-001 | OL 100 mg TID | irritability (irritability) | mild | Y | possibly related | resolved | N |
| 02-001 | OL 100 mg TID | intentional self-injury (self injurious behavior) | mild | Y | possibly related | resolved | N |
| 02-001 | OL 100 mg TID | confusional state (mental confusion) | mild | Y | possibly related | resolved | N |
| 02-001 | OL 100 mg TID | anxiety (anxious) | mild | Y | possibly related | resolved | N |
| 02-002 | OL 100 mg TID | irritability (irritability) | mild | Y | probably related | unknown | N |
| 02-002 | OL 100 mg TID | intentional self-injury (violent episodes of self injurious behavior) | mild | Y | probably related | resolving | N |
| 01-011 | OL 200 mg TID | cough (cough) | moderate | Y | not related | resolved | N |
| 01-011 | OL 200 mg TID | pyrexia (fever) | moderate | Y | not related | resolved | N |
| 01-016 | OL 200 mg TID | seasonal allergy (seasonal allergy) | moderate | Y | not related | not resolved | N |
| 01-016 | OL 200 mg TID | fatigue (tiredness) | mild | Y | possibly related | resolved | N |

DB = double-blind;
OL = open-label
[1]AE reported at 4-week follow-up visit
[2]AE reported pre-treatment Of the patients who experienced an AE (34.1%, 14 of 41 patients), the majority experienced AEs of mild (24.4%, 10 of 41 patients) to moderate (14.6%, 6 of 41 patients) intensity. Only three AEs were reported by more than one patient. Intentional self-injury was reported as a treatment emergent AE by two patients in the open-label 100 mg group and one patient in the double-blind placebo group. Irritability was reported as a treatment emergent AE by two patients in the open-label 100 mg group. For one of the patients reporting intentional self-injury and irritability (02-002), these symptoms emerged within a few days of withdrawal from active treatment (i.e., after completion of Week 4). For the other patient (02-001), symptoms began while on active drug treatment. Urine cystine crystal present was reported as a non-treatment emergent AE at the 4-week follow-up visit by two patients in the double-blind 200 mg group.

There were no serious adverse events (SAEs) or deaths reporting during the study. A total of 2 patients were withdrawn from the study due to adverse events: 1 patient in the double-blind 200 mg group experienced a treatment emergent AE of grand mal seizure and 1 patient in the double-blind placebo group experienced treatment emergent AEs of intentional self-injury and agitation.

Vital Signs

Figure 3:
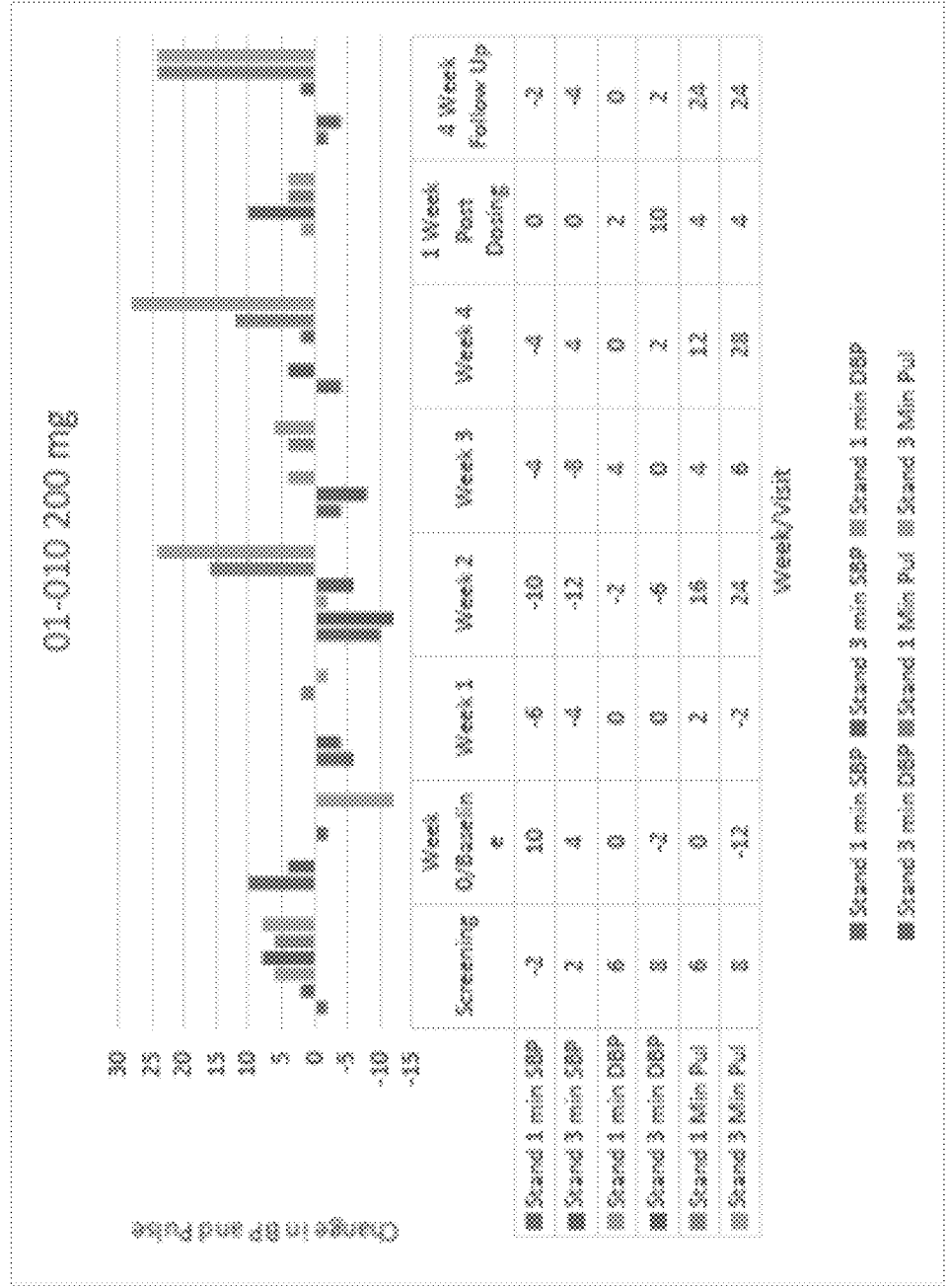
FIG. 3 shows an example of largest change from baseline in vital signs noted in a patient in Study HT 02-121 (Example 6) and demonstrates that these changes were transient, falling far short of ortho static criteria.

Orthostatic vital signs were taken at each visit as described in Study HT 02-121. There were no changes observed that met criteria for orthostatic hypotension (i.e., drop in systolic blood pressure of 20 mm Hg, drop in diastolic blood pressure of 10 mm hg, or increases in heart rate of 30 beats per minute). A small number of subjects demonstrated asymptomatic drop in systolic and/or diastolic blood pressures, along with increase in heart rate at Week 1 or Week 2 of treatment, but these resolved by Week 4 and were mild in nature (e.g., a drop of 10 mm Hg in systolic blood pressure, 5 mm Hg in diastolic pressure and increase of 15-24 beats per minute in heart rate). FIG. 3 provides an example of the largest change from baseline that was noted, and demonstrates that these changes were transient, falling far short of orthostatic criteria.

ECGS and Laboratory Evaluations

No clinically significant changes from baseline EKGs were noted in any of the patients. Urinalysis revealed no findings related to clinical symptoms. Of note was the observation that half (50%) of the patients on L1-79 developed crystalluria compared to 30% of placebo treated patients. Of those that developed crystalluria during the study, approximately half (50%) had concentrated urine (specific gravity >1.025). Most of the crystalluria consisted of calcium oxalate crystals. There were no symptoms associated with the crystalluria.

One patient developed asymptomatic transient mild elevation of amylase at Week 4 (146 U/L, upper limit of normal [ULN] is 125 U/L), which resolved by the 4-week follow up visit.

There were no significant elevations in AST or ALT or any other chemistry parameters noted in the safety population.

Assessment of hematology parameters revealed no significant deviations in the safety population.

Pharmacokinetics

Figure 4:
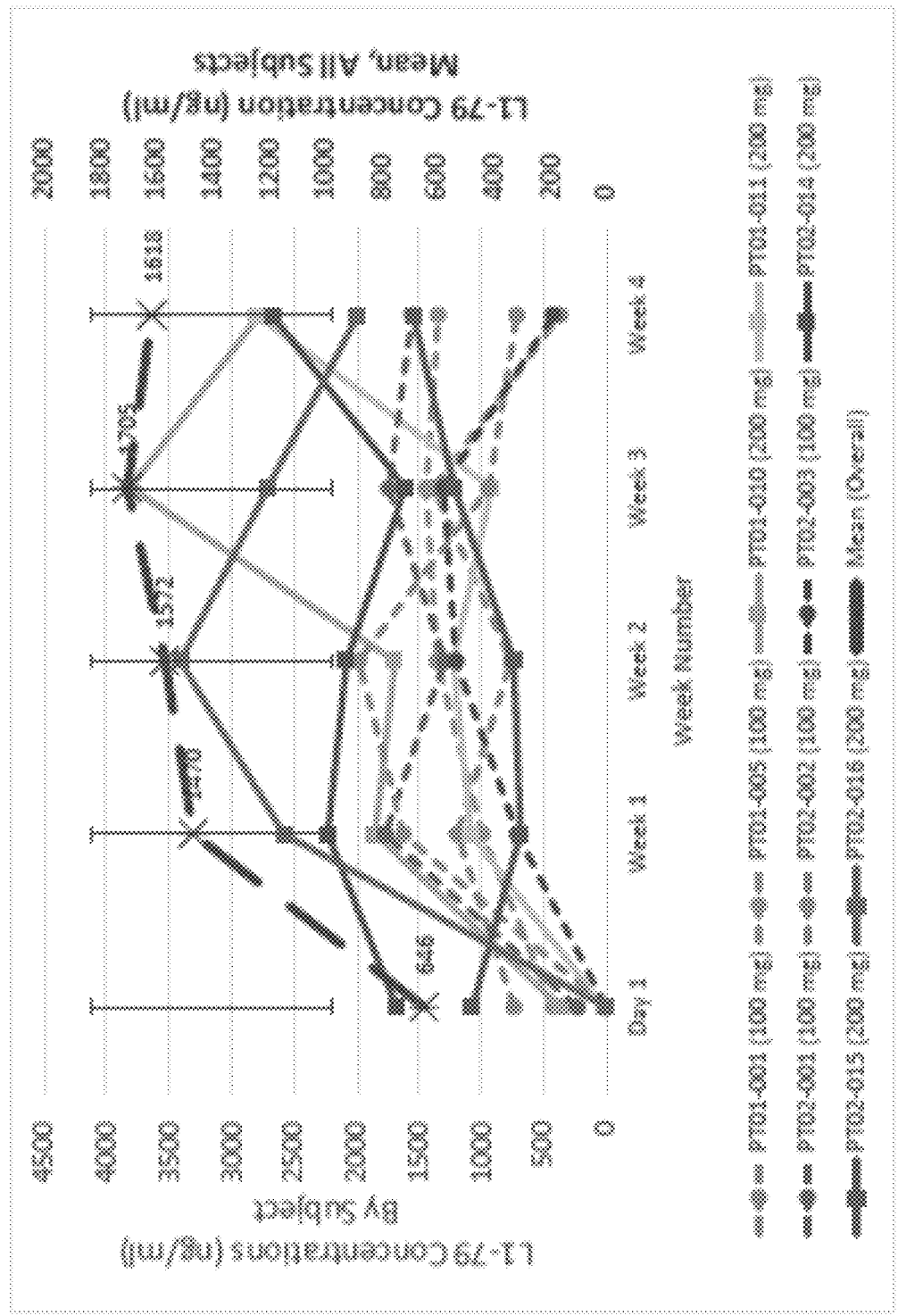
FIG. 4 shows random L1-79 plasma concentrations (except Day 1*) by week, overall mean and by patient from open-label 100 mg and 200 mg TID in Study HT 02-121. *1 On Day 1, L-79 plasma concentrations were evaluated at 1-hour post-dose.
Figure 5:
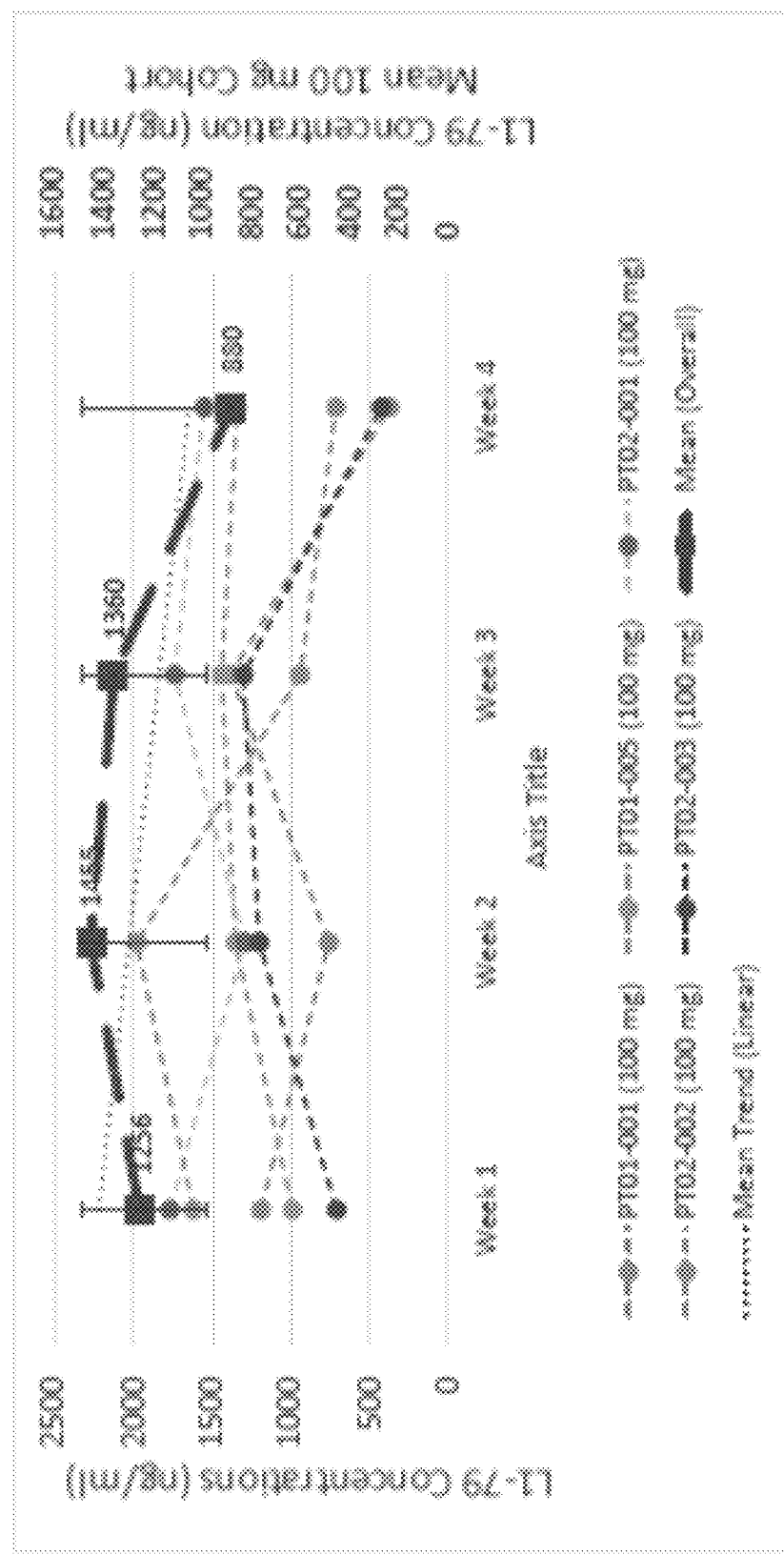
FIG. 5 shows random L1-79 plasma concentrations by week (excluding Day 1), overall mean and by patient from open-label 100 mg TID group in Study HT 02-121.
Figure 6:
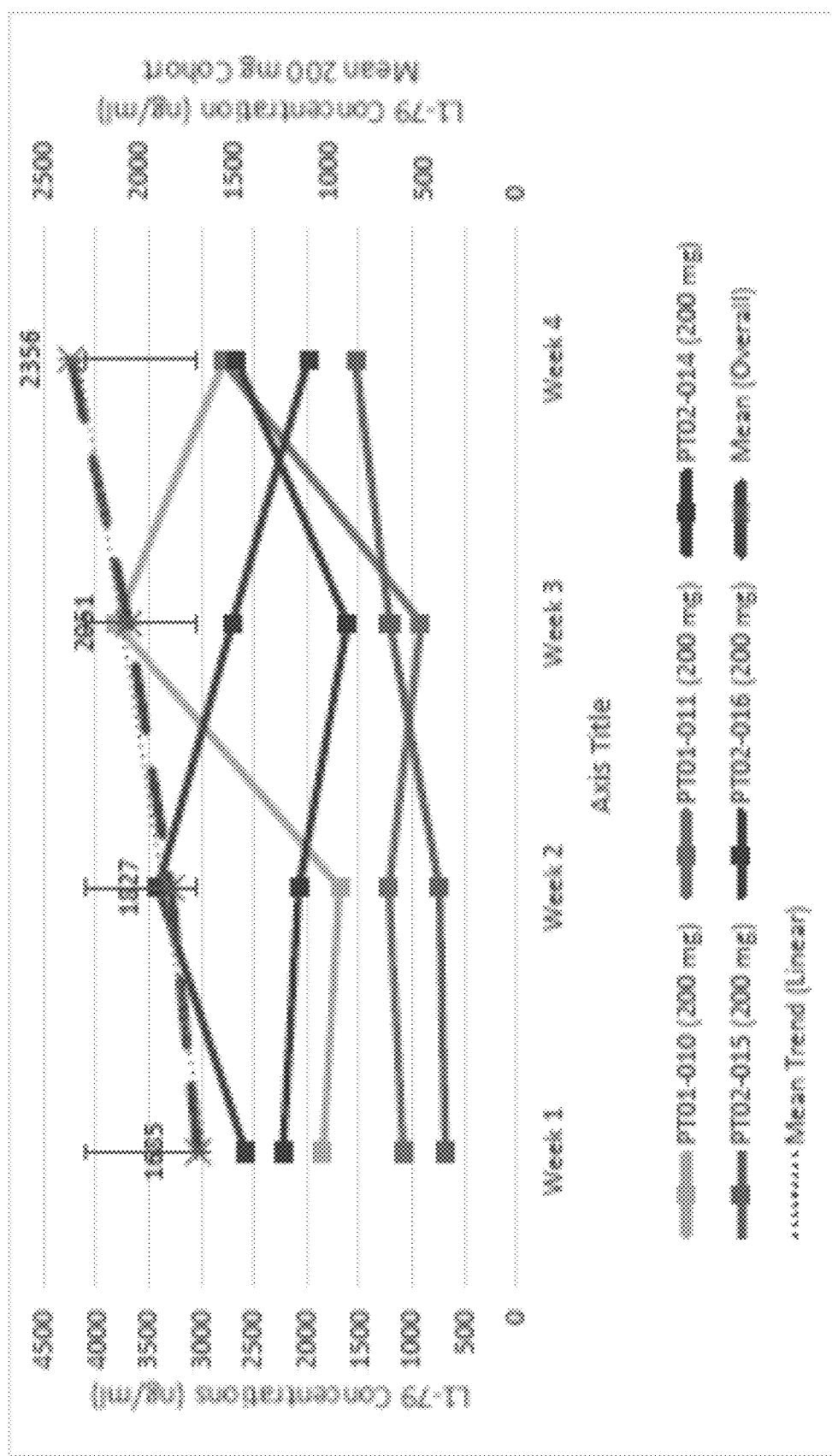
FIG. 6 shows random L1-79 plasma concentrations by week (excluding Day 1), overall Mean and by patient from open-label 200 mg TID group in Study HT 02-121.

Pharmacokinetics were assessed in the open-label 100 mg and 200 mg TID patients. On Day 1, L-79 concentrations were assessed one-hour post dose. Subsequently, a random L1-79 plasma concentration was assessed at Week 1, Week 2, Week 3 and Week 4. At 1-hour post-dose on Day 1 plasma concentrations with 100 mg and 200 mg TID ranged from 0 (<2.5) to 736 ng/mL and 23 to 1680 ng/mL, respectively. A summary of individual patient and combined overall mean L1-79 random plasma concentrations are shown in FIG. 4. As shown in FIG. 5 and FIG. 6, overall, random plasma L1-79 concentrations were relatively stable over Week 1 to Week 4.

Efficacy

At the time this study was initiated, there was a lack of long-term, juvenile and reproductive toxicology data. Applicants embarked on a short study of 28 days in duration, with a limitation in the number, gender, and age of the patients allowed into the study. As a result, this study was not designed or powered to demonstrate statistical significance on any of the efficacy endpoints. Thus, as expected none of the outcomes measures achieved statistical significance. What was anticipated, and what was observed, were positive trends in a variety of instruments consistent with an improvement in the core symptoms of autism. In fact, there were multiple efficacy measures demonstrating similar indicators of improvement in the treatment of target core social domains affected by ASD. In addition, efficacy data are only displayed for patients that received blinded treatment.

Outcome Measures

There were some differences in how questionnaires were administered during Cohort 1 and Cohort 2 of the study. In the preliminary study, all forms were completed at the study site in the presence of the investigator. In Cohort 1 of the present study, the VABS—II, SRS-2, ABC-C and RBS-R were filled out at home by the patient/patient's families prior to treatment visits and returned at treatment visits in order to expedite the execution of the study. The assessment procedures for VABS II, SRS-2, ABC-C and RBS-R during Cohort 1 were not done at the treatment visits and as a result, families had difficulties filling out the forms properly. In order improve the quality and completeness of the questionnaires during Cohort 2, all questionnaires (with the exception of the ADOS-2 [administered by external certified ADOS-2 test administrator for both cohorts] and CGI [completed by investigator in both cohorts]) were completed by the principal investigator with the assistance of the patient/patient's families at the pre-specified treatment visits. As the Cohort 2 data was more robust, the discussion of results focus on the comparison of L1-79 200 mg to placebo, with the exception of the ADOS-2 and CGI, where both L1-79 100 mg and 200 mg are compared to placebo.

After the conclusion of the study, it was discovered that the basal anchors for the VABS-II were not always appropriately established. In addition, only two subdomains (communication and socialization) were completed for the patients, making it impossible to obtain domain or total scores. However, the results for the VABS II communication and socialization domains are presented below.

A tabular summary of the efficacy measures is presented below (Table 9). For those measures demonstrating positive trends in favor of L1-79 three sets of figures are presented for each efficacy measure. The figures consist of the following: a) a line graph showing the comparative change between the 3 treatment groups from screening/baseline to 4 weeks (followed by a 4-week post treatment timepoint in some cases), b) an individual patient response plot, and c) a responder analysis plot. For those efficacy measures not showing a positive trend in favor of L1-79, only a line graph showing the comparative change between the 3 treatment groups from screening/baseline to week 4 (followed by a 4-week post treatment timepoint in some cases) is presented.

Responder Definition:

In addition to analyzing the data by observing the magnitude of change in each efficacy endpoint for patients exposed to active drug compared to placebo, it is important to define a 'responder' population. In general, responder analyses are intended to focus on the number of patients demonstrating any benefit, rather than the overall change in the studied population. Typically, responders are defined as patients whose target symptoms demonstrate a pre-specified improvement in the efficacy endpoint. This definition is consistent with accepted standards for judging mid and long term outcomes for experimental treatments studied in nearly every disorder, including autism. However, it does not take into account the need for a refined definition in studies of short duration for disorders, like autism, that have oscillations in symptom severity. In ASD, children often go through periods of mild to moderate improvement or worsening in their behavioral, social and emotional symptom regulation related to a variety of identifiable and as yet unidentified factors (Boso, 2010; Jyonouchi, 2011). Thus, in a study of short duration, a 'baseline' measure may in fact be at the apex, midpoint or nadir of one of these oscillations. If they are at an apex or mid-point when the target symptoms under study are measured at baseline, then a short duration study may only have the opportunity to demonstrate initial efficacy by preventing the target symptom from returning back to its oscillatory nadir. To account for this probable occurrence among some study patients, the responder definition includes patients demonstrating either short term stability or improvement in the target symptoms. Thus, for each efficacy endpoint demonstrating a positive trend, responder analyses were conducted as defined herein.

A tabular summary of the change from screening/baseline for efficacy measures is provided in Table 9.

TABLE 9

Summary Comparisons of Mean Changes from Screening/Baseline Between L1-79 and Placebo for Efficacy Measures at Week 4 or LOCF.

|  | Double-blind L1-79 100 mg TID N = 9 | Double-blind L1-79 200 mg TID N = 11 | Placebo N = 9 |
|---|---|---|---|
| CGI-S (N) | 9 | 11 | 9 |
| Mean Change from Baseline (SD) | −0.3 (0.5) | −0.8 (0.9) | −0.3 (0.5) |
| Range (min, max) | −1, 0 | −2, 0 | −1, 0 |
| Quartiles ($25^{th}$, median, $75^{th}$) | −1, −0, 0 | −2, −1, 0 | −1, 0, 0 |
| Treatment effect versus placebo (95% CI) | −0.0 (−0.5, 0.5) | −0.5 (−1.2, 0.2) | N/A |
| P-value for treatment effect | 1.00 | 0.16 | N/A |
| CGI-I (N) | 9 | 11 | 8 |
| Mean Change from Baseline (SD) | −0.6 (0.7) | −0.5 (0.8) | −0.1 (0.8) |
| Range (min, max) | −1, 1 | −2, 0 | −1, 1 |
| Quartiles (25th, median, 75th) | −1, −1, 0 | −1, 0, 0 | −1, 0, 1 |
| Treatment effect versus placebo (95% CI) | −0.4 (−1.2, 0.4) | −0.3 (−1.1, 0.5) | N/A |
| P-value for treatment effect | 0.27 | 0.40 | N/A |
| VABS II Standardized Socialization Score (N) | 5 | 7 | 4 |
| Mean Change from Baseline (SD) | −4.2 (12.1) | 7.6 (11.9) | 0.8 (1.5) |
| Range (min, max) | −14, 9 | 0, 29 | 0, 3 |
| Quartiles ($25^{th}$, median, $75^{th}$) | −13, −12, 9 | 0, 1, 20 | 0, 0, 2 |
| Treatment effect versus placebo (95% CI) | −5.0 (−19.9, 10.0) | 6.8 (−4.2, 17.8) | N/A |
| P-value for treatment effect | 0.41 | 0.18 | N/A |
| VABS II Standardized Communication Score (N) | 8 | 7 | 4 |
| Mean Change from Baseline (SD) | 10.1 (16.6) | 2.7 (4.3) | 6.5 (9.3) |
| Range (min, max) | −3, 46 | 0, 12 | 0, 20 |
| Quartiles ($25^{th}$, median, $75^{th}$) | −1, 5, 16 | 0, 1, 3 | 1, 3, 13 |
| Treatment effect versus placebo (95% CI) | 3.6 (−16.5, 23.8) | −3.8 (−12.9, 5.3) | N/A |
| P-value for treatment effect | 0.70 | 0.37 | N/A |
| ADOS-2 Total Score (N) | 9 | 10 | 8 |
| Mean Change from Screening (SD) | −0.6 (1.7) | −1.0 (2.2) | 0.0 (2.1) |
| Range (min, max) | −4, 2 | −6, 2 | −3, 4 |
| Quartiles ($25^{th}$, median, $75^{th}$) | −1, 0, 0 | −1, −1, 0 | −1, −1, 1 |
| Treatment effect versus placebo (95% CI) | −0.6 (−2.5, 1.4) | −1.0 (−3.2, 1.2) | N/A |
| P-value for treatment effect | 0.56 | 0.34 | N/A |
| ADOS-2 Restricted and Repetitive Behavior (N) | 9 | 10 | 7 |
| Mean Change from Screening (SD) | 0.3 (1.6) | −1.0 (2.1) | −0.1 (2.5) |
| Range (min, max) | −1, 4 | −6, 1 | −3, 4 |
| Quartiles ($25^{th}$, median, $75^{th}$) | −1, 0, 1 | −2, −1, 0 | −2, −1, 2 |
| Treatment effect versus placebo (95% CI) | 0.5 (−1.7, 2.7) | −0.9 (−3.2, 1.5) | N/A |
| P-value for treatment effect | 0.65 | 0.45 | N/A |
| ADOS-2 Social Affect (N) | 9 | 10 | 7 |
| Mean Change from Screening (SD) | −0.9 (2.0) | 0.0 (2.1) | 0.1 (1.1) |
| Range (min, max) | −5, 1 | −4, 3 | −1, 2 |
| Quartiles ($25^{th}$, median, $75^{th}$) | −2, 0, 1 | −1, 1, 1 | −1, 0, 1 |
| Treatment effect versus placebo (95% CI) | −1.0 (−2.9, 0.8) | −0.1 (−2.0, 1.7) | N/A |
| P-value for treatment effect | 0.24 | 0.87 | N/A |
| SRS-2 Total T-score (N) | 8 | 11 | 9 |
| Mean Change from Baseline (SD) | −0.4 (6.2) | −7.7 (10.9) | −5.2 (9.6) |
| Range (min, max) | −11, 10 | −30, 3 | −22, 5 |
| Quartiles ($25^{th}$, median, $75^{th}$) | −3, −1, 3 | −19, −3, 0 | −12, −2, 1 |
| Treatment effect versus placebo (95% CI) | 4.8 (−3.7, 13.4) | −2.5 (−12.3, 7.3) | N/A |
| P-value for treatment effect | 0.24 | 0.60 | N/A |
| SRS-2 DSM-5 Social, Communication and Interaction T-score (N) | 9 | 11 | 9 |
| Mean Change from Baseline (SD) | 0.6 (5.4) | −7.6 (10.3) | −4.2 (10.4) |
| Range (min, max) | −9, 8 | −28, 3 | −24, 8 |
| Quartiles ($25^{th}$, median, $75^{th}$) | −3, 2, 5 | −18, −3, 0 | −12, −1, 1 |
| Treatment effect versus placebo (95% CI) | 4.8 (−3.5, 13.1) | −3.4 (−13.2, 6.4) | N/A |
| P-value for treatment effect | 0.24 | 0.47 | N/A |
| SRS-2 DSM-5 Restricted and Repetitive Behavior T-score (N) | 9 | 11 | 8 |
| Mean Change from Baseline (SD) | −0.4 (9.3) | −7.6 (13.2) | −7.6 (10.8) |
| Range (min, max) | −17, 14 | −34, 6 | −30, 3 |
| Quartiles ($25^{th}$, median, $75^{th}$) | −3, 0, 5 | −22, −3, 3 | −12, −7, 1 |
| Treatment effect versus placebo (95% CI) | 7.2 (−3.2, 17.6) | −0.0 (−12.1, 12.1) | N/A |
| P-value for treatment effect | 0.087 | 1.00 | N/A |
| SRS-2 Social Communication T-score (N) | 9 | 11 | 9 |
| Mean Change from Baseline (SD) | 1.1 (7.1) | −8.3 (11.0) | −4.9 (10.6) |

TABLE 9-continued

Summary Comparisons of Mean Changes from Screening/Baseline Between L1-79 and Placebo for Efficacy Measures at Week 4 or LOCF.

|  | Double-blind L1-79 100 mg TID N = 9 | Double-blind L1-79 200 mg TID N = 11 | Placebo N = 9 |
|---|---|---|---|
| Range (min, max) | −9, 13 | −30, 1 | −22, 6 |
| Quartiles (25th, median, 75th) | −5, 0, 6 | −16, −4, −1 | −13, 0, 3 |
| Treatment effect versus placebo (95% CI) | 6.0 (−3.0, 15) | −3.4 (−13.6, 6.9) | N/A |
| P-value for treatment effect | 0.18 | 0.50 | N/A |
| SRS-2 Social-Motivation T-score (N) | 9 | 11 | 9 |
| Mean Change from Baseline (SD) | −1.4 (9.2) | −10.6 (12.6) | −1.8 (9.9) |
| Range (min, max) | −15, 12 | −30, 6 | −16, 15 |
| Quartiles (25th, median, 75th) | −7, −4, 8 | −21, −6, 0 | −8, −2, 4 |
| Treatment effect versus placebo (95% CI) | 0.3 (−9.2, 9.9) | −8.9 (−19.7, 2.0) | N/A |
| P-value for treatment effect | 0.94 | 0.10 | N/A |
| ABC-C Lethargy and Social Withdrawal (N) | 9 | 11 | 9 |
| Mean Change from Baseline (SD) | −1.6 (6.7) | −4.5 (6.7) | −5.4 (6.4) |
| Range (min, max) | −15, 7 | −19, 5 | −14, 3 |
| Quartiles (25th, median, 75th) | −2, −1, 1 | −9, −2, 0 | −11, −3, −1 |
| Treatment effect versus placebo (95% CI) | 3.9 (−2.6, 10.4) | 1.0 (−5.2, 7.2) | N/A |
| P-value for treatment effect | 0.23 | 0.74 | N/A |
| ABC-C Inappropriate Speech (N) | 9 | 11 | 9 |
| Mean Change from Baseline (SD) | 0.0 (1.7) | −2.0 (2.4) | −1.6 (2.7) |
| Range (min, max) | −2, 2 | −7, 0 | −8, 1 |
| Quartiles (25th, median, 75th) | −2, 0, 1 | −4, −1, 0 | −2, 0, 0 |
| Treatment effect versus placebo (95% CI) | 1.6 (−0.7, 3.8) | −0.4 (−2.9, 2.0) | N/A |
| P-value for treatment effect | 0.16 | 0.71 | N/A |
| ABC-C Hyperactivity and Noncompliance | 9 | 11 | 8 |
| Mean Change from Baseline (SD) | 0.4 (3.9) | −4.0 (9.1) | −4.5 (6.0) |
| Range (min, max) | −8, 5 | −28, 7 | −13, 6 |
| Quartiles (25th, median, 75th) | 0, 0, 3 | −7, −1, 0 | −9, −5, −1 |
| Treatment effect versus placebo (95% CI) | 4.9 (−0.2, 10.1) | 0.5 (−7.3, 8.3) | N/A |
| P-value for treatment effect | 0.060 | 0.89 | N/A |
| ABC-C Irritability and Agitation | 9 | 11 | 8 |
| Mean Change from Baseline (SD) | −0.9 (2.0) | −2.2 (6.9) | −3.4 (7.1) |
| Range (min, max) | −5, 2 | −16, 9 | −11, 12 |
| Quartiles (25th, median, 75th) | −2, −1, 0 | −7, −2, 0 | −8, −5, −1 |
| Treatment effect versus placebo (95% CI) | 2.5 (−3.5, 8.5) | 1.2 (−5.7, 8.0) | N/A |
| P-value for treatment effect | 0.37 | 0.72 | N/A |
| ABC-C Stereotypic Behavior | 9 | 11 | 8 |
| Mean Change from Baseline (SD) | 1.9 (3.3) | −1.7 (2.9) | −0.6 (5.4) |
| Range (min, max) | −1, 8 | −7, 1 | −5, 12 |
| Quartiles (25th, median, 75th) | 0, 0, 4 | −3, −1, 0 | −4, −2, −1 |
| Treatment effect versus placebo (95% CI) | 2.5 (−2.0, 7.1) | −1.1 (−5.1, 2.9) | N/A |
| P-value for treatment effect | 0.26 | 0.57 | N/A |
| RBS-R Total Score (N) | 9 | 11 | 8 |
| Mean Change from Baseline (SD) | −3.2 (7.8) | −16.1 (24.1) | −11.0 (11.0) |
| Range (min, max) | −14, 12 | −78, 1 | −24, 6 |
| Quartiles (25th, median, 75th) | −6, −4, −1 | −28, −2, 0 | −21, −12, −2 |
| Treatment effect versus placebo (95% CI) | 7.8 (−2.0, 17.5) | −5.1 (−22.7, 12.5) | N/A |
| P-value for treatment effect | 0.11 | 0.55 | N/A |
| RBS-R Restricted Behavior (N) | 9 | 11 | 7 |
| Mean Change from Baseline (SD) | 1.3 (2.6) | −2.5 (2.8) | −1.6 (1.6) |
| Range (min, max) | −1, 8 | −8, 0 | −4, 0 |
| Quartiles (25th, median, 75th) | 0, 1, 1 | −5, −1, 0 | −3, −2, 0 |
| Treatment effect versus placebo (95% CI) | 2.9 (0.5, 5.4) | −1.0 (−3.4, 1.5) | N/A |
| P-value for treatment effect | 0.023 | 0.41 | N/A |
| RBS-R Ritualistic Behavior (N) | 9 | 11 | 7 |
| Mean Change from Baseline (SD) | 0.1 (2.8) | −3.1 (4.1) | −3.7 (3.5) |
| Range (min, max) | −4, 4 | −13, 0 | −9, 0 |
| Quartiles (25th, median, 75th) | −1, 0, 2 | −5, −1, 0 | −7, −3, 0 |
| Treatment effect versus placebo (95% CI) | 3.8 (0.5, 7.2) | 0.6 (−3.4, 4.6) | N/A |
| P-value for treatment effect | 0.028 | 0.74 | N/A |
| RBS-R Sameness Behavior (N) | 9 | 11 | 7 |
| Mean Change from Baseline (SD) | −0.7 (2.0) | −4.2 (7.1) | −2.9 (2.2) |
| Range (min, max) | −4, 2 | −22, 1 | −6, 0 |
| Quartiles (25th, median, 75th) | −1, −1, 0 | −9, 0, 0 | −5, −2, −1 |
| Treatment effect versus placebo (95% CI) | 2.2 (−0.1, 4.4) | −1.3 (−6.3, 3.6) | N/A |
| P-value for treatment effect | 0.056 | 0.57 | N/A |
| RBS-R Compulsive Behavior (N) | 9 | 11 | 7 |
| Mean Change from Baseline (SD) | −1.2 (3.6) | −2.7 (4.9) | −1.6 (1.7) |
| Range (min, max) | −8, 3 | −16, 0 | −4, 0 |
| Quartiles (25th, median, 75th) | −2, 0, 1 | −3, 0, 0 | −3, −1, 0 |
| Treatment effect versus placebo (95% CI) | 0.3 (−2.8, 3.5) | −1.2 (−4.6, 2.3) | N/A |
| P-value for treatment effect | 0.82 | 0.49 | N/A |
| RBS-R Stereotypic Behavior (N) | 9 | 11 | 7 |
| Mean Change from Baseline (SD) | −0.6 (1.7) | −1.8 (2.8) | −0.4 (4.2) |
| Range (min, max) | −5, 1 | −7, 0 | −7, 6 |

TABLE 9-continued

Summary Comparisons of Mean Changes from Screening/Baseline Between L1-79 and Placebo for Efficacy Measures at Week 4 or LOCF.

|  | Double-blind L1-79 100 mg TID N = 9 | Double-blind L1-79 200 mg TID N = 11 | Placebo N = 9 |
| --- | --- | --- | --- |
| Quartiles (25th, median, 75th) | 0, 0, 0 | −5, 0, 0 | −3, 0, 3 |
| Treatment effect versus placebo (95% CI) | −0.1 (−4.1, 3.8) | −1.4 (−4.8, 2.1) | N/A |
| P-value for treatment effect | 0.94 | 0.41 | N/A |
| RBS-R Self Injurious Behavior (N) | 9 | 11 | 7 |
| Mean Change from Baseline (SD) | −2.2 (5.3) | −1.7 (3.9) | −2.1 (3.8) |
| Range (min, max) | −16, 1 | −12, 1 | −8, 2 |
| Quartiles (25th, median, 75th) | −2, 0, 0 | −1, 0, 0 | −7, 0, 0 |
| Treatment effect versus placebo (95% CI) | −0.1 (−5.2, 5.0) | 0.4 (−3.5, 4.4) | N/A |
| P-value for treatment effect | 0.97 | 0.83 | N/A |

LOCF = last observation carried forward

Clinical Global Impression (CGI) Rating Scales

Figure 7:
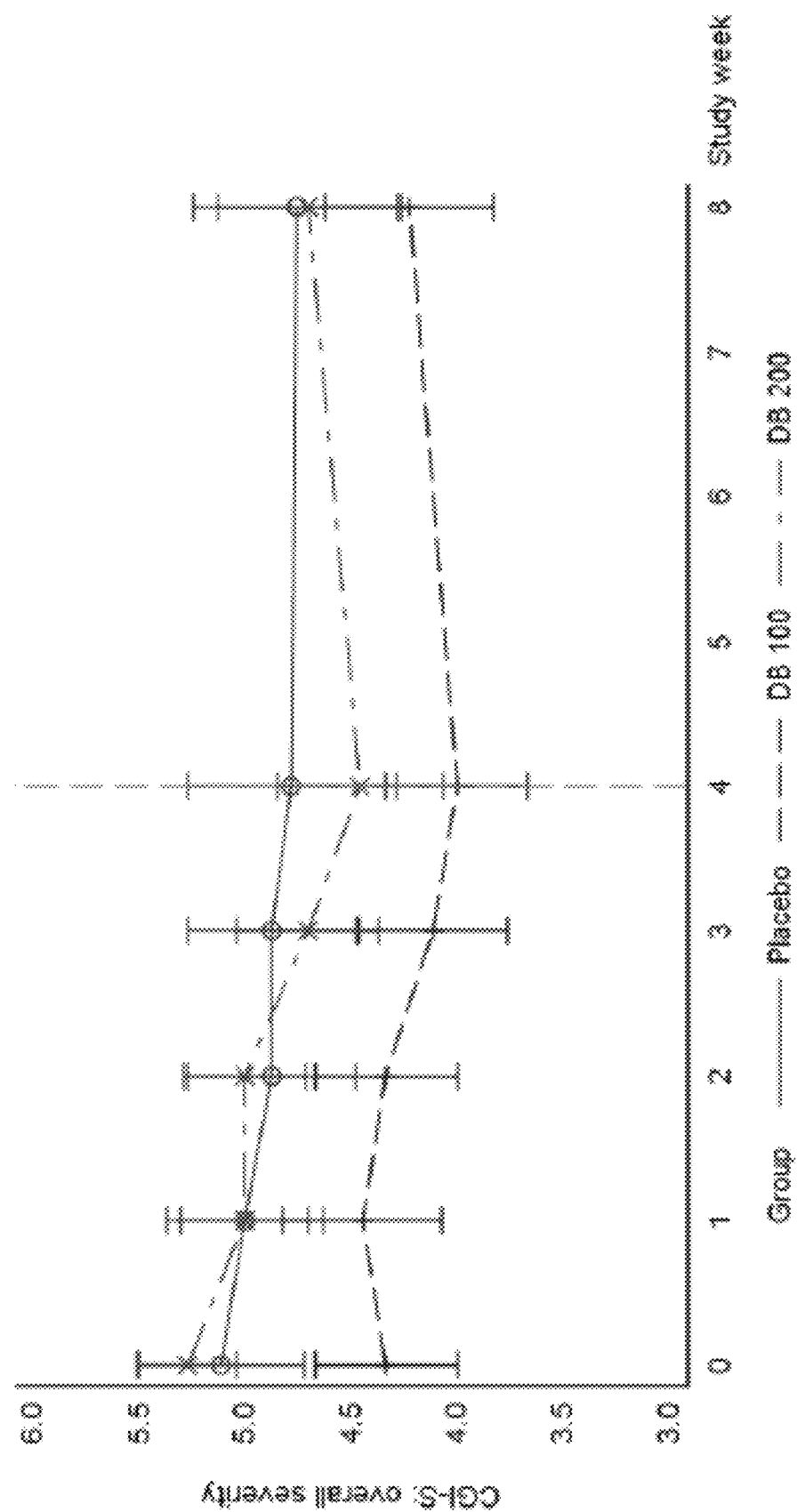
FIG. 7 graphically displays shows the CGI—Overall Severity (CGI-S) for L1-79 compared to placebo over time.
Figure 8:
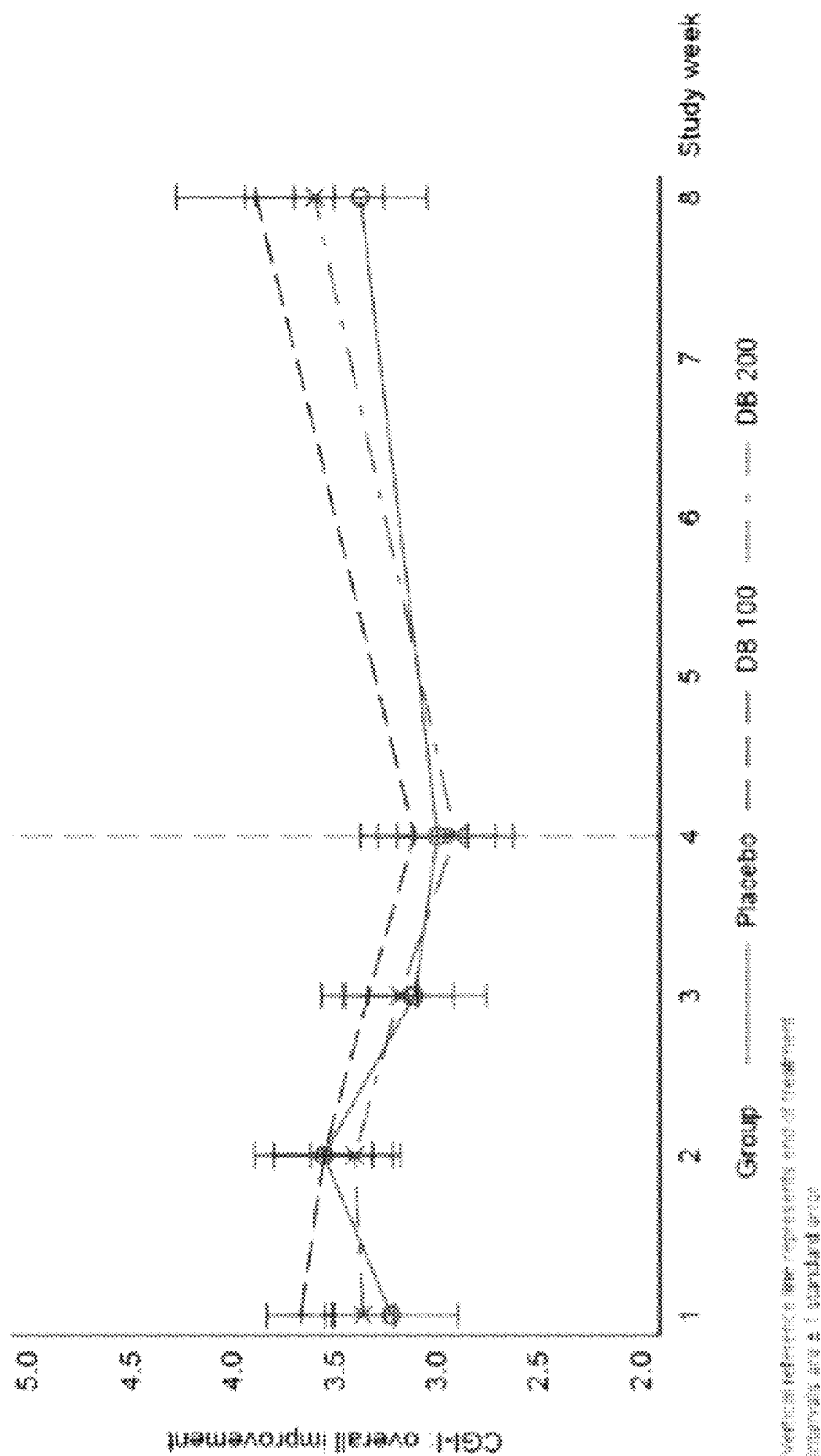
FIG. 8 graphically displays the CGI—Overall Improvement (CGI-I) for L1-79 compared to placebo over time.
Figure 9:
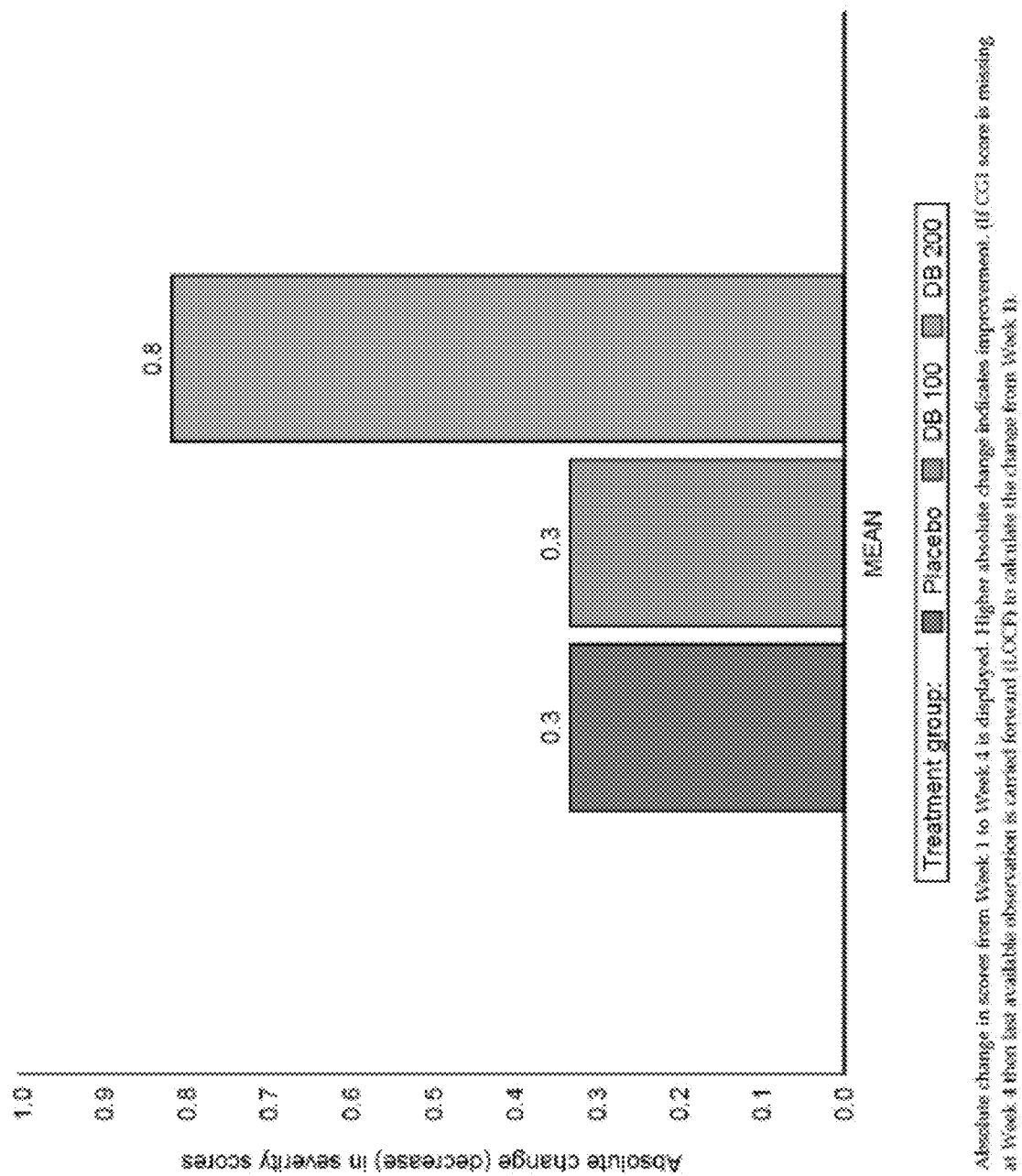
FIG. 9 shows the change from baseline in CGI-S at week 4 (ITT Population, Draft).

The CGI-Overall Severity (CGI-S) and CGI-Overall Improvement (CGI-I) for L1-79 compared to placebo over time are displayed graphically in FIG. 7 and FIG. 8. The mean CGI-S change from baseline at Week 4 or last observation carried forward (LOCF) is displayed in FIG. 9, and demonstrates a mean 0.5 point improvement on the overall CGIS for patients in the 200 mg group, compared to those in the placebo and 100 mg groups.

Figure 10:
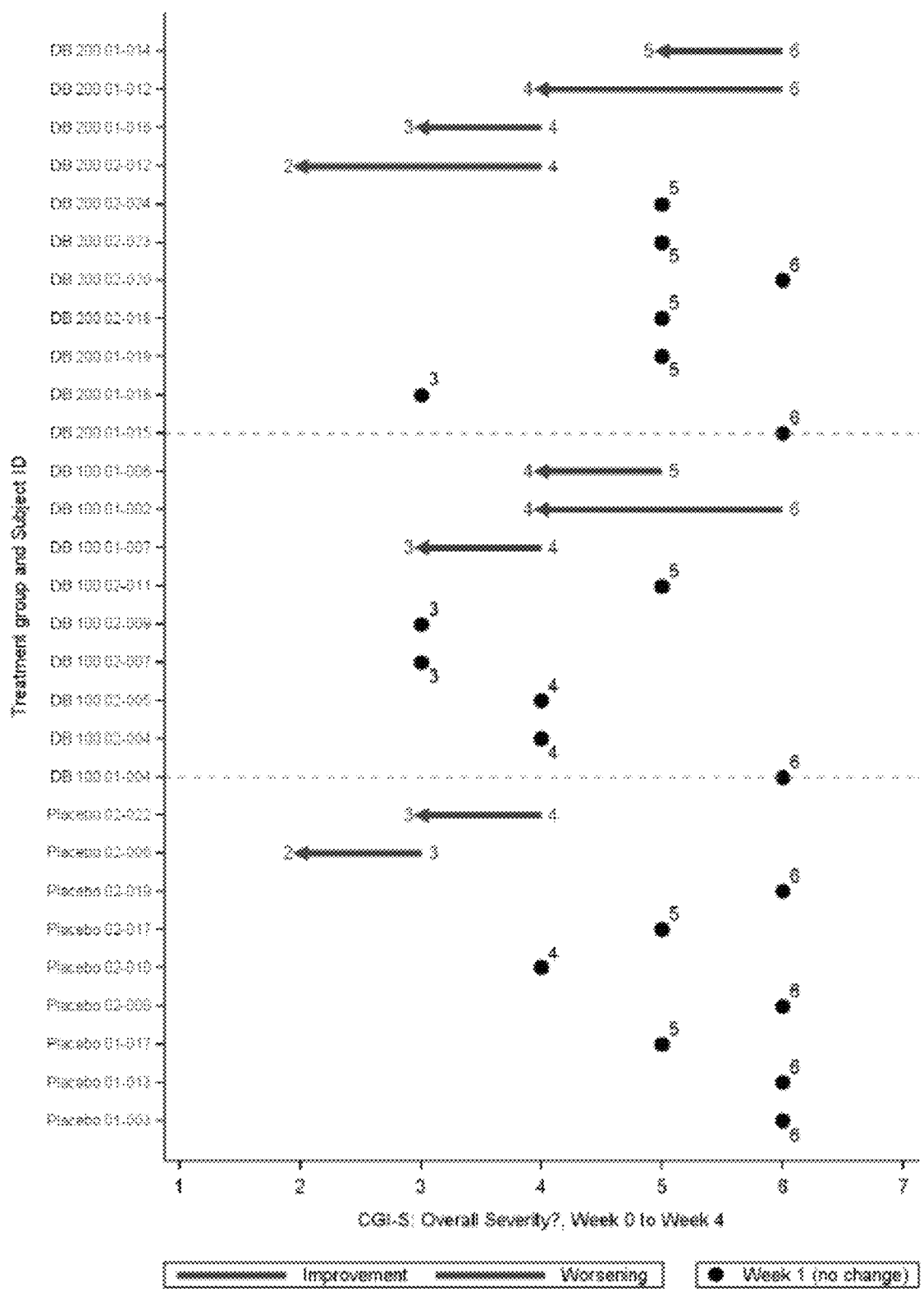
FIG. 10 shows the change in CGI-S from Baseline to Week 4 by Patient (ITT Population, Draft).
Figure 11:
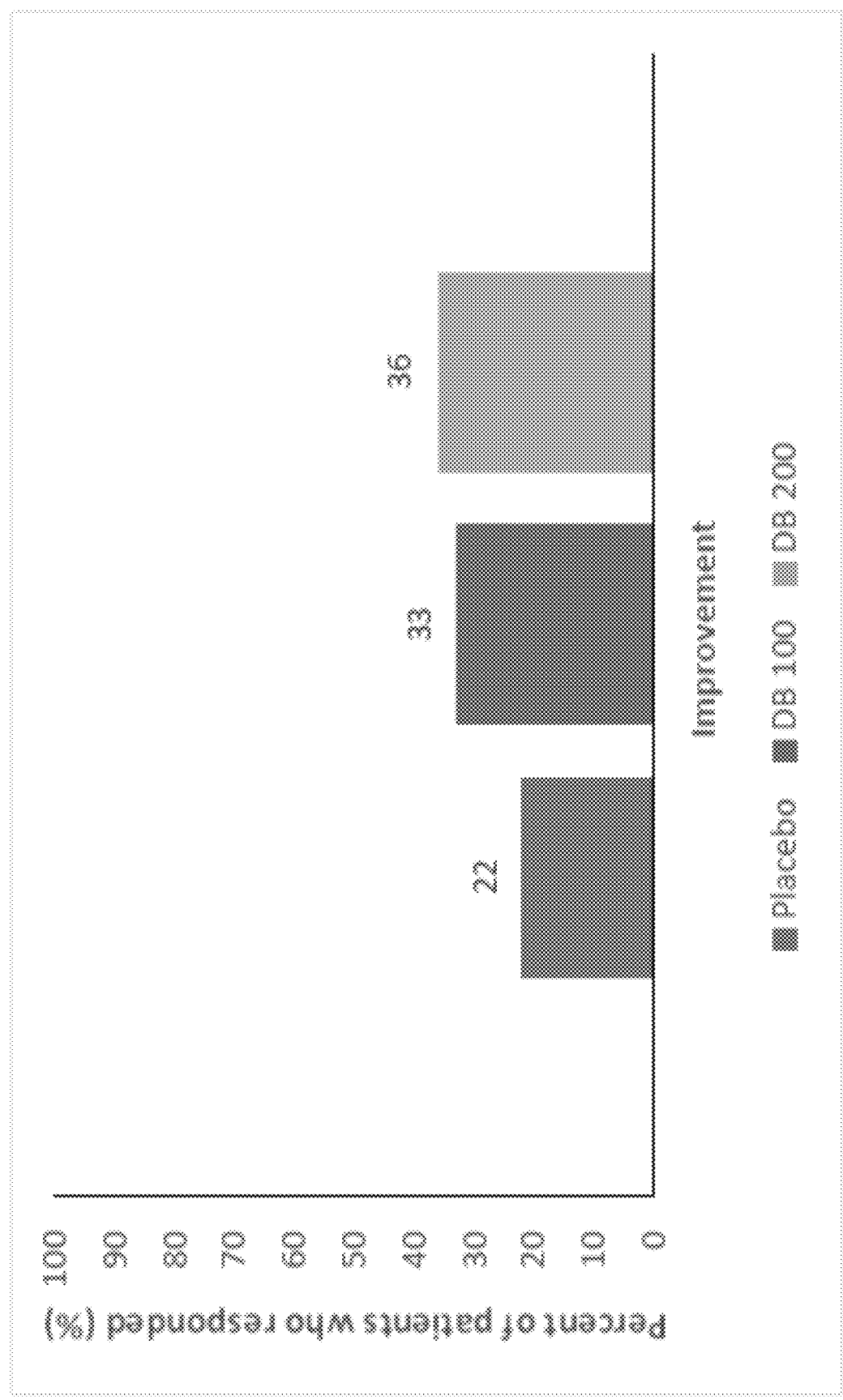
FIG. 11 shows the responder analysis for CGI-S at Week 4/LOCF (ITT Population, Draft).

A summary of the change in CGI-S from Baseline to Week 4 is displayed by patient in FIG. 10. In addition, responder analyses (defined as improvement) are presented for CGIS at Week 4 or LOCF in FIG. 11.

Responder definitions for CGI-S were defined as improvement only (instead of improvement or no change) since, unlike the other measures which were performed weekly, the CGI-S requires the clinician to give an overall assessment of the patients' clinical symptom severity based on all of the outcome measures and their movement over the entirety of the study.

The responder analysis for CGI-S at Week 4 demonstrates a clear dose response trend of improvement for the L1-79 100 mg and 200 mg groups compared to placebo.

Vineland Adaptive Behavior Scales, Second Edition (VABS II)

Figure 12:
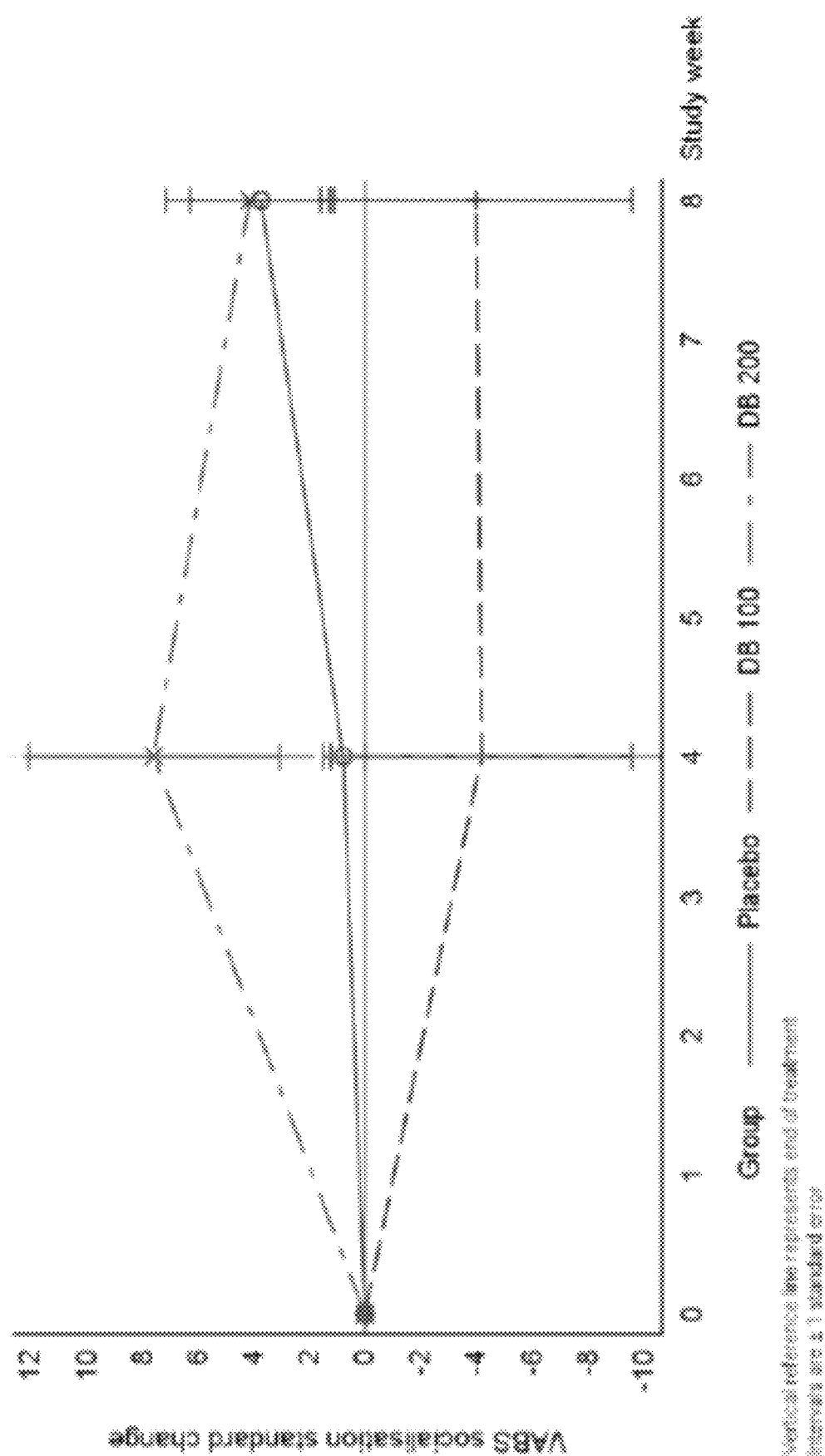
FIG. 12 shows the change from Baseline in VABS II Standardized Socialization Score, Week 0-Week 8 (ITT Population, Draft).
Figure 13:
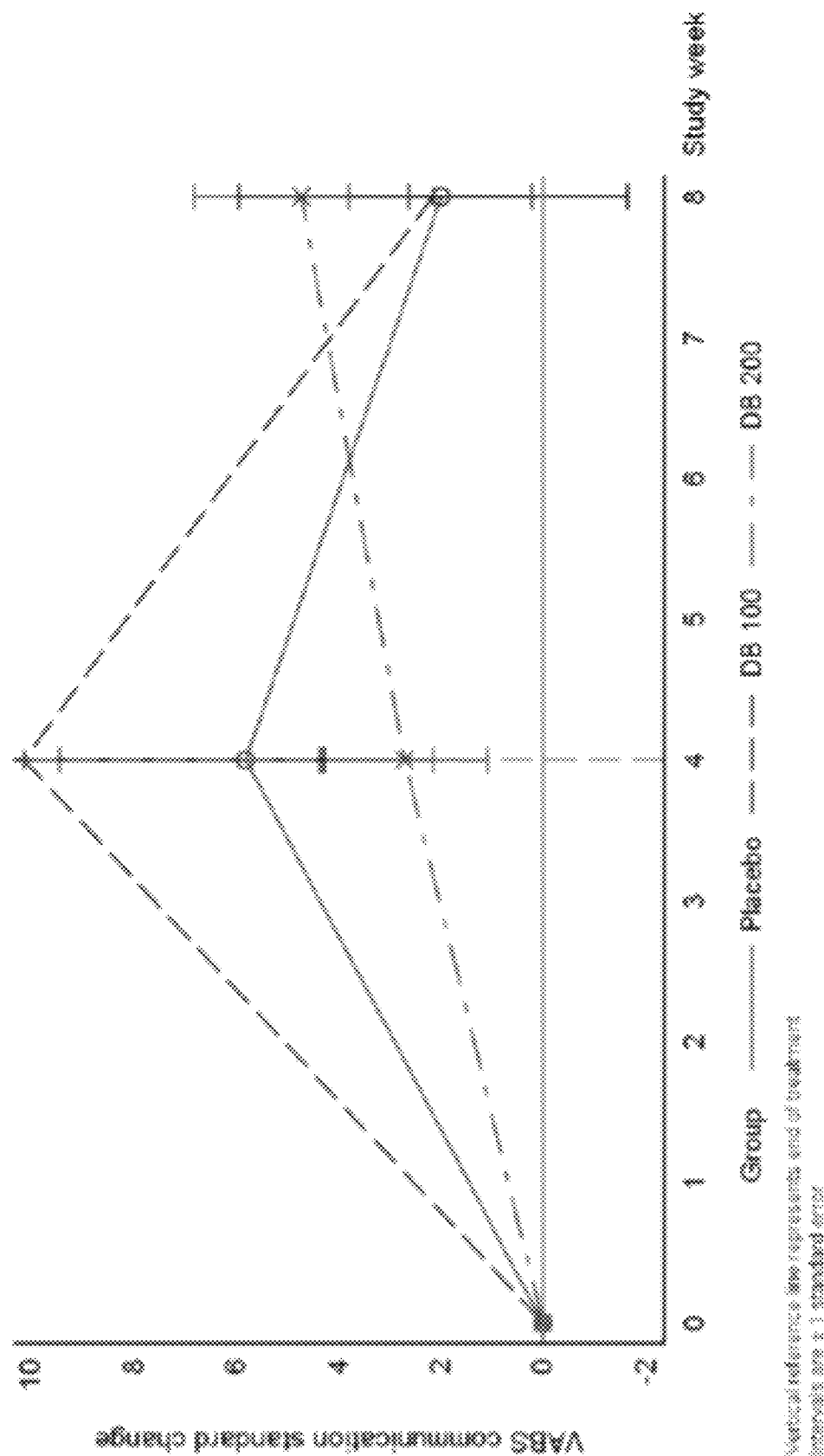
FIG. 13 shows the change from Baseline in VABS II Standardized Communication Score, Week 0-Week 8 (ITT Population, Draft).

The change from Baseline in VABS II Standardized Socialization Score and the VABS II Standardized Communication Score for L1-79 compared to placebo over time are displayed graphically in FIG. 12 and FIG. 13, respectively.

Autism Diagnostic Observation Schedule, Second Edition (ADOS-2)

Figure 14:
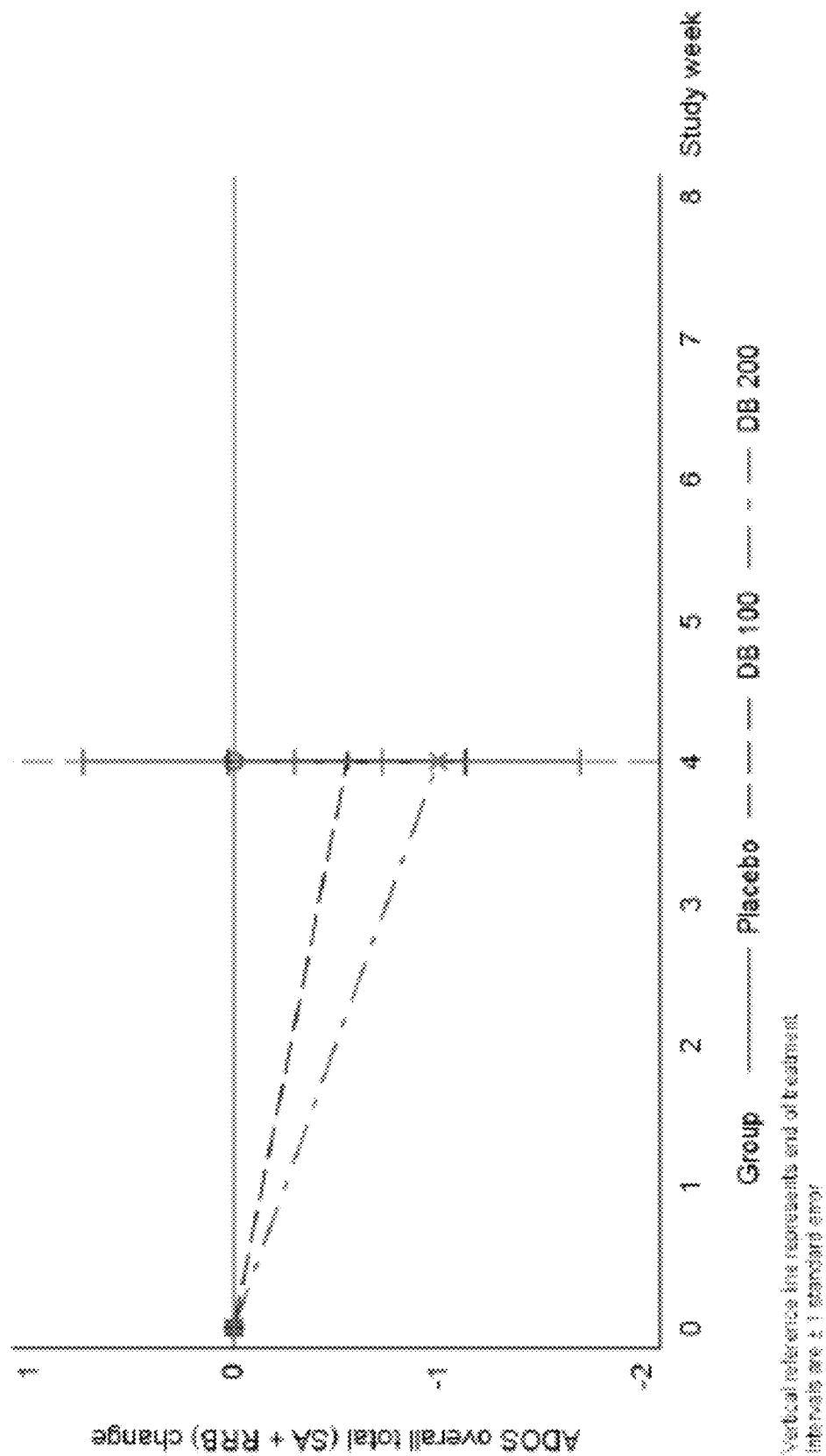
FIG. 14 shows the change from Screening in ADOS-2 Total score, Week 0-Week 4 (ITT Population, Draft).
Figure 15:
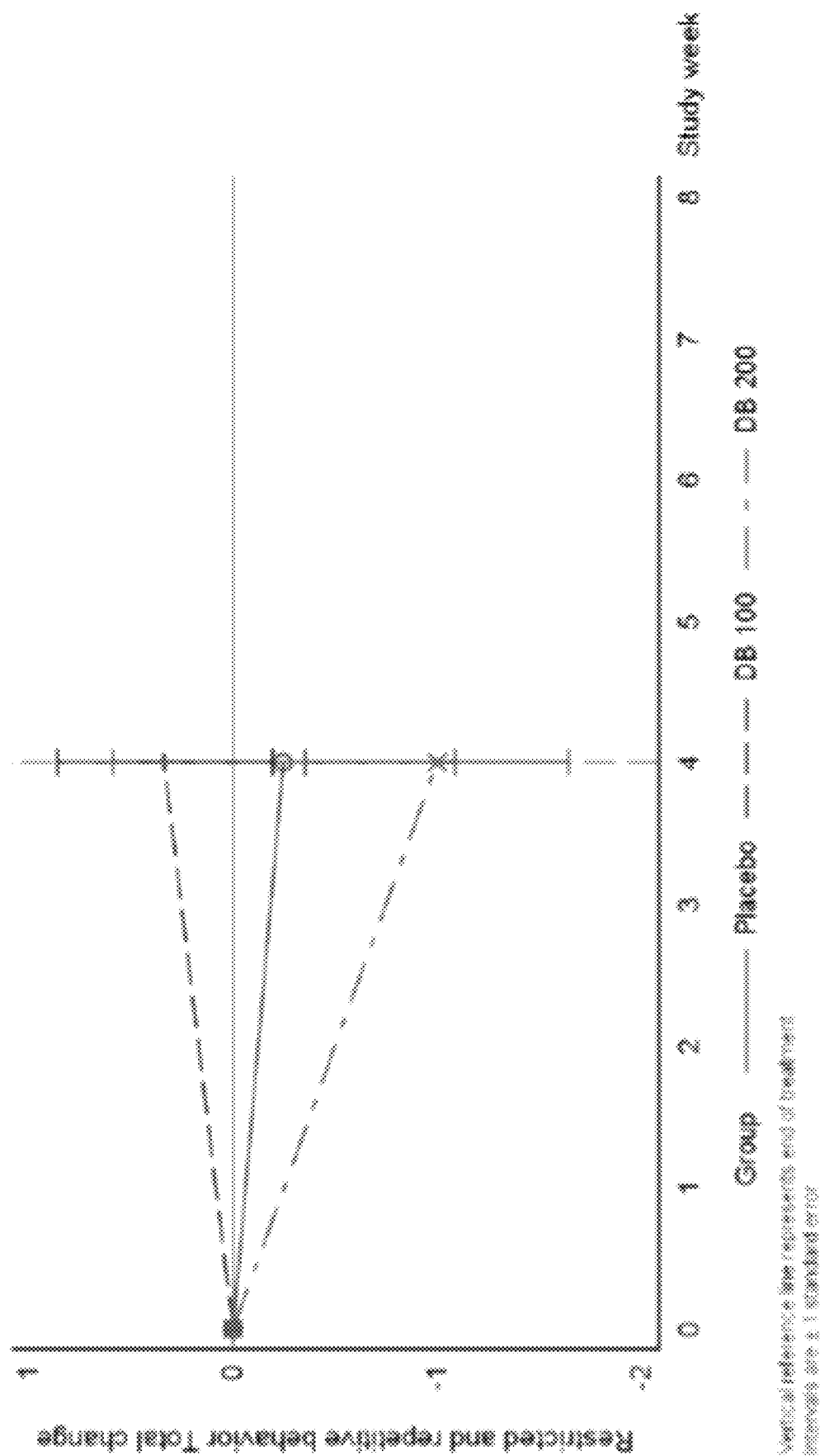
FIG. 15 shows the change from Screening in ADOS-2 Restrictive and Repetitive Behavior Total score, Week 0-Week 4 (ITT Population, Draft).
Figure 16:
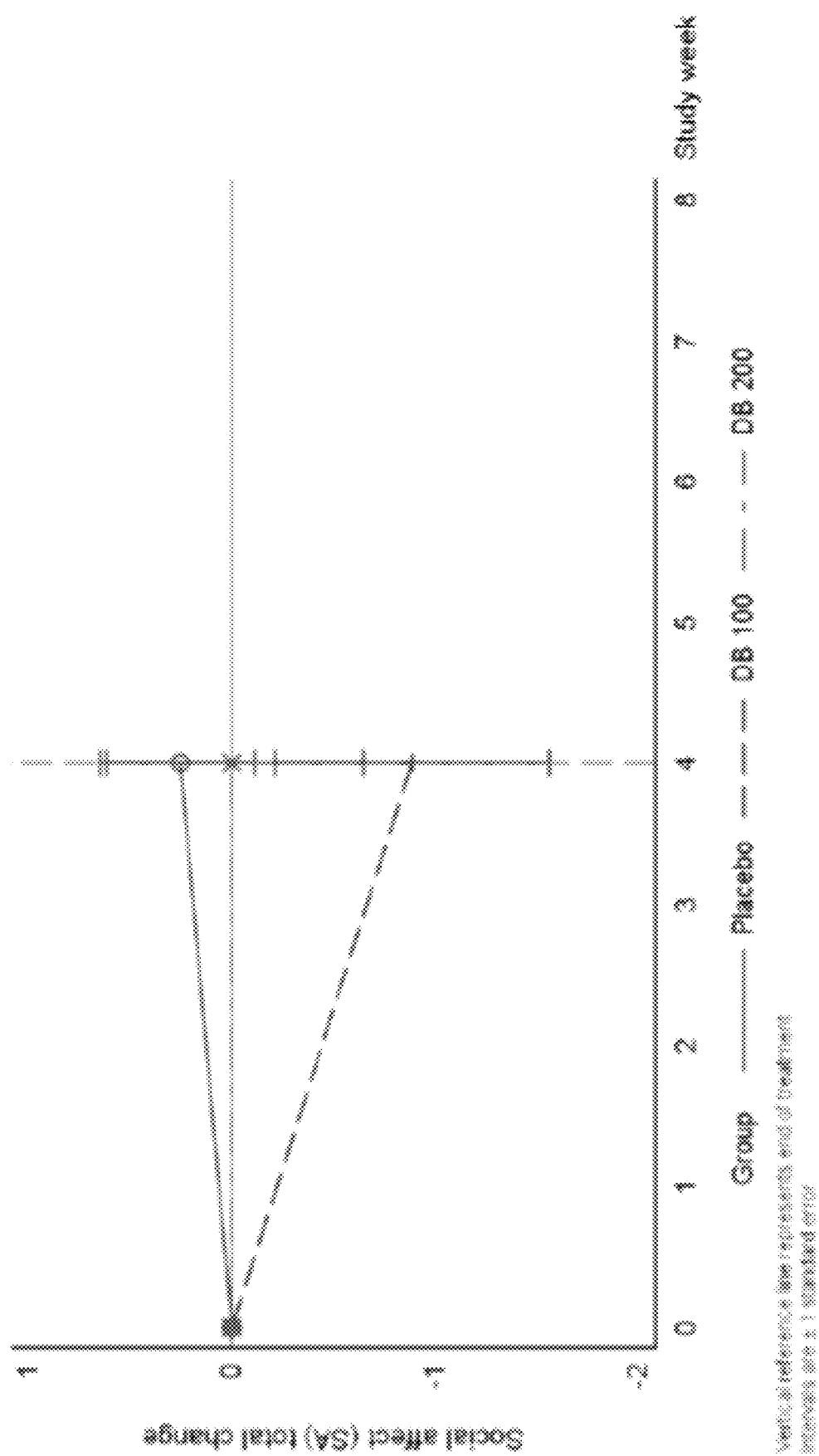
FIG. 16 shows the change from Screening in ADOS-2 Social Affect Total Score, Week 0-Week 4 (ITT Population, Draft).

The change from Screening in ADOS-2 Total Score, Restrictive and Repetitive Behavior Total Score and Social Affect Total Score for L1-79 compared to placebo over time are displayed graphically in FIG. 14, FIG. 15 and FIG. 16. While not typically used as an outcome measure, the change in ADOS-2 over a short period of time is consistent with open-label preliminary study of longer duration previously presented.

Figure 17:
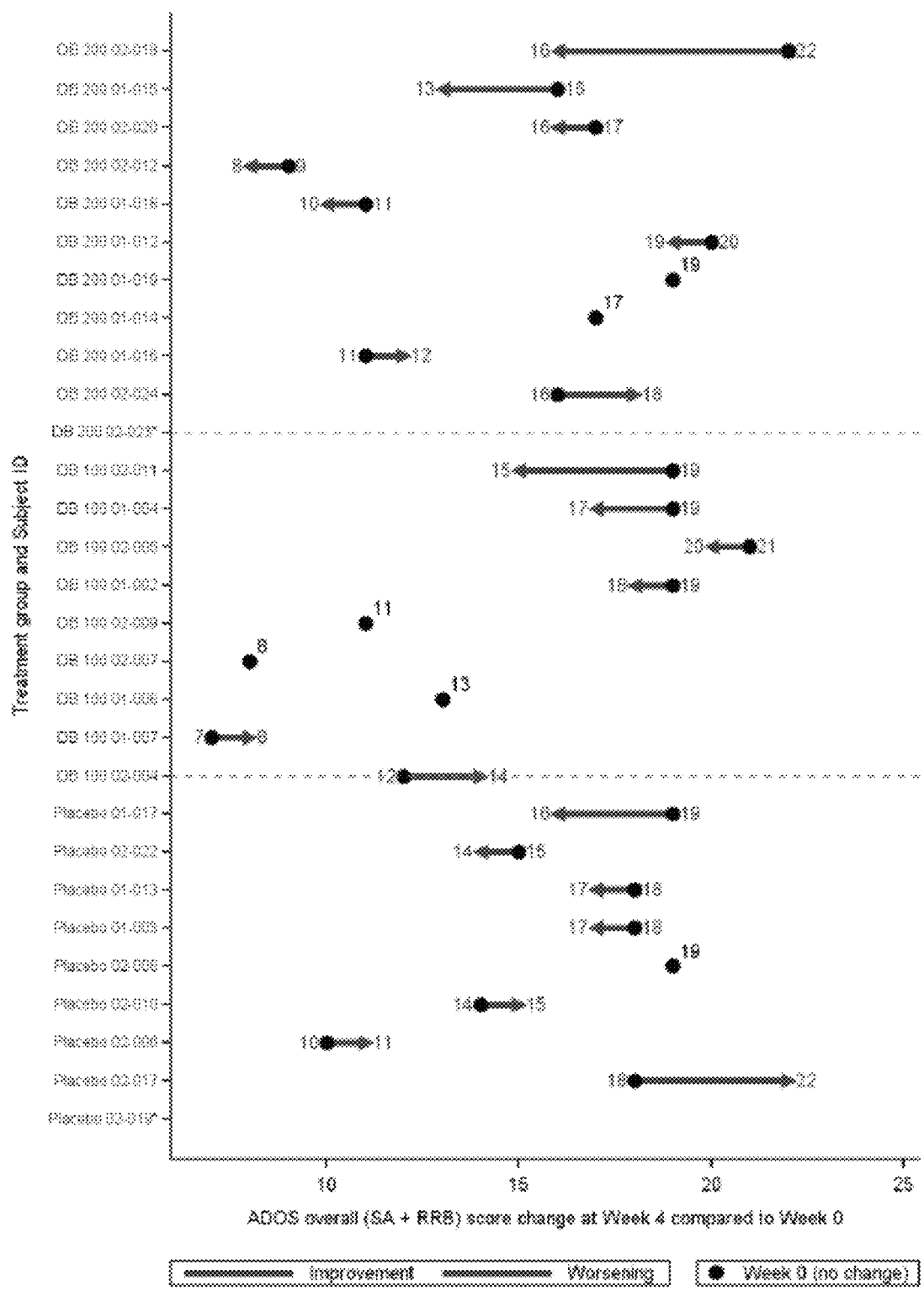
FIG. 17 shows the change in ADOS-2 Total Score from Screening to Week 4 by Patient (ITT Population, Draft).
Figure 18:
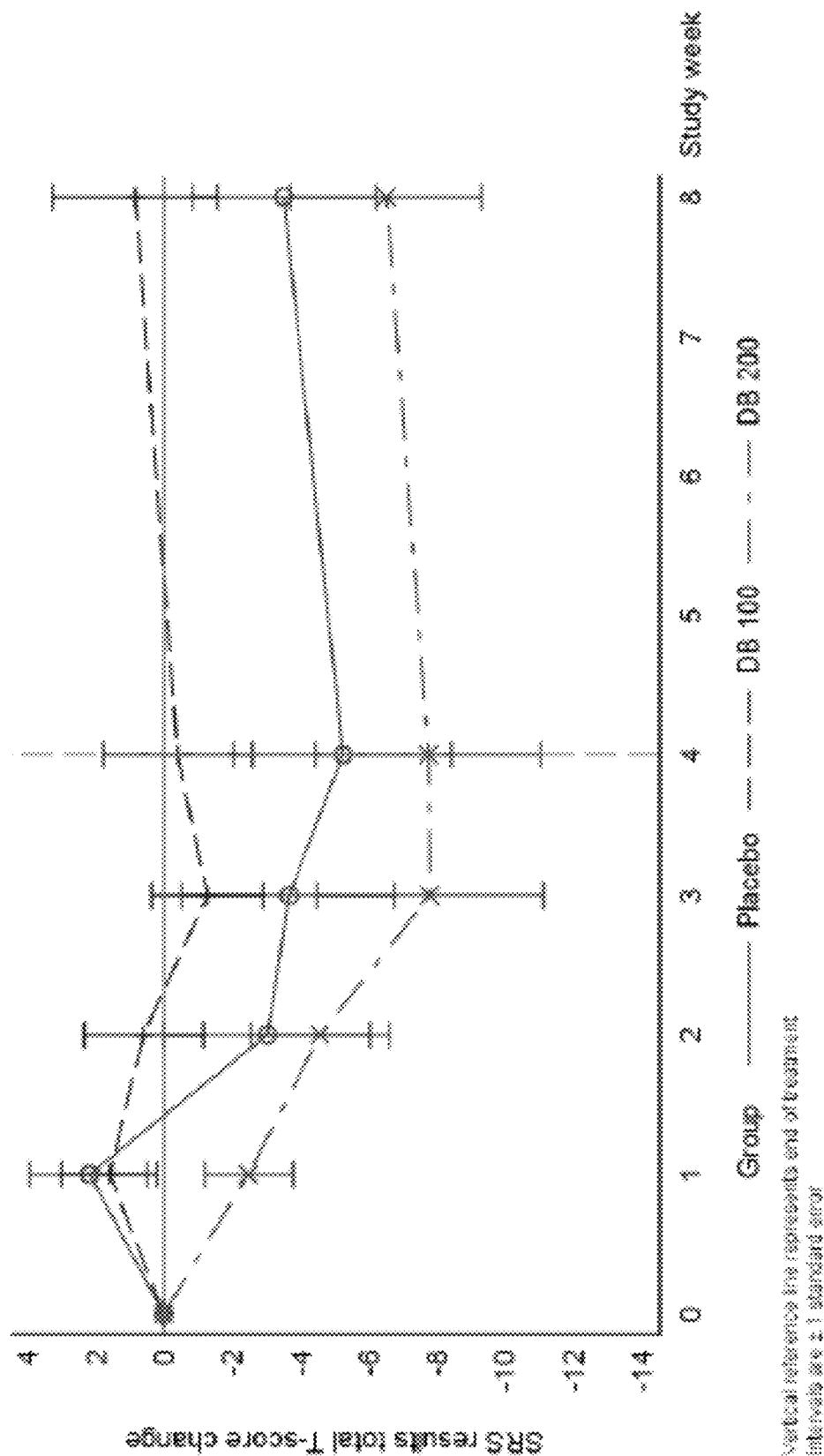
FIG. 18 shows the change from Baseline in SRS-2 Total T-score, Week 0-Week 8 (ITT Population, Draft).
Figure 19:
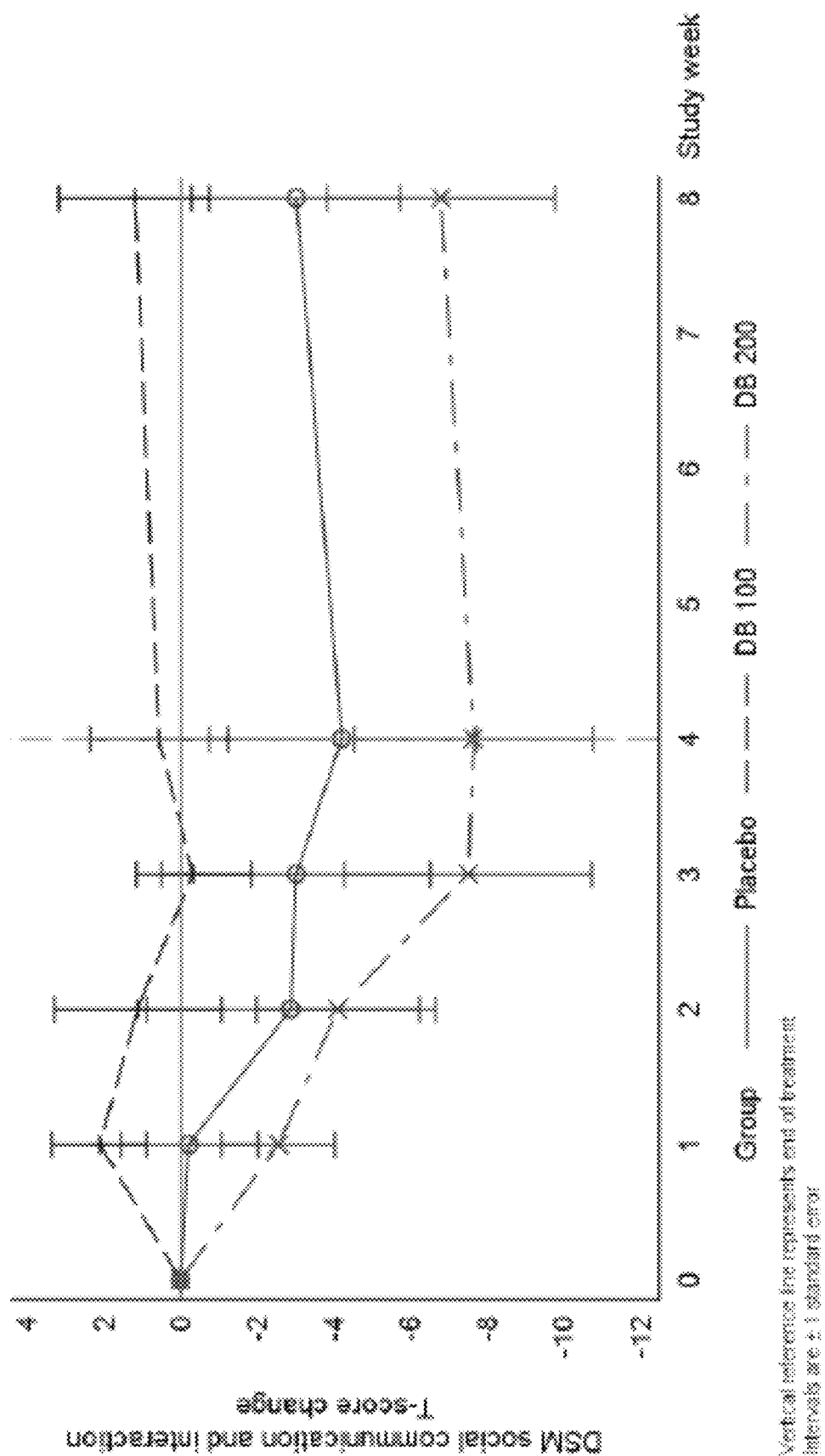
FIG. 19 shows the change from Baseline in SRS-2 DSM-5 Social Communication and Interaction T-score, Week 0-Week 8 (ITT Population, Draft).
Figure 20:
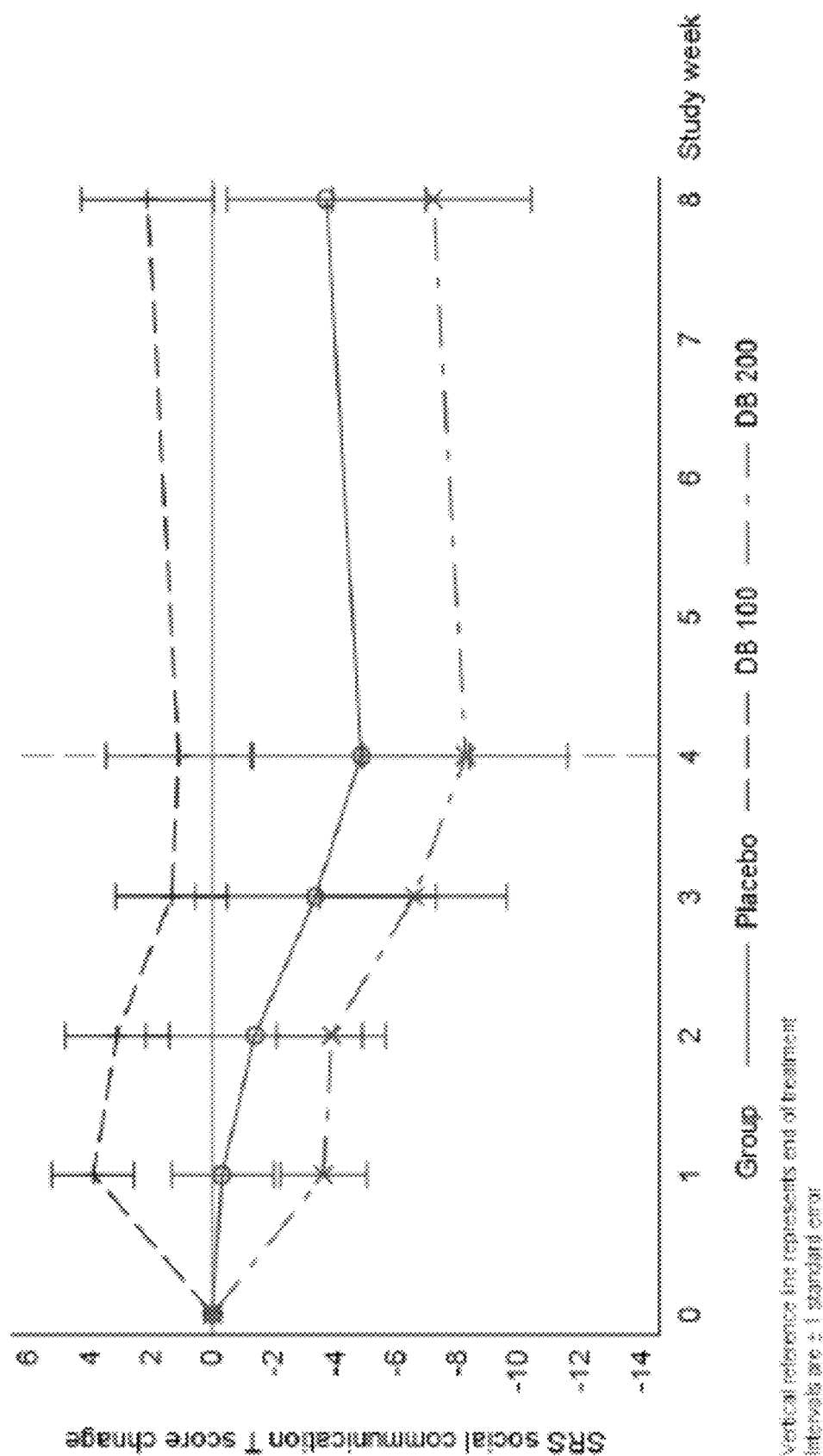
FIG. 20 shows the change from Baseline in SRS-2 Social Communication T-score, Week 0-Week 8 (ITT Population, Draft).
Figure 21:
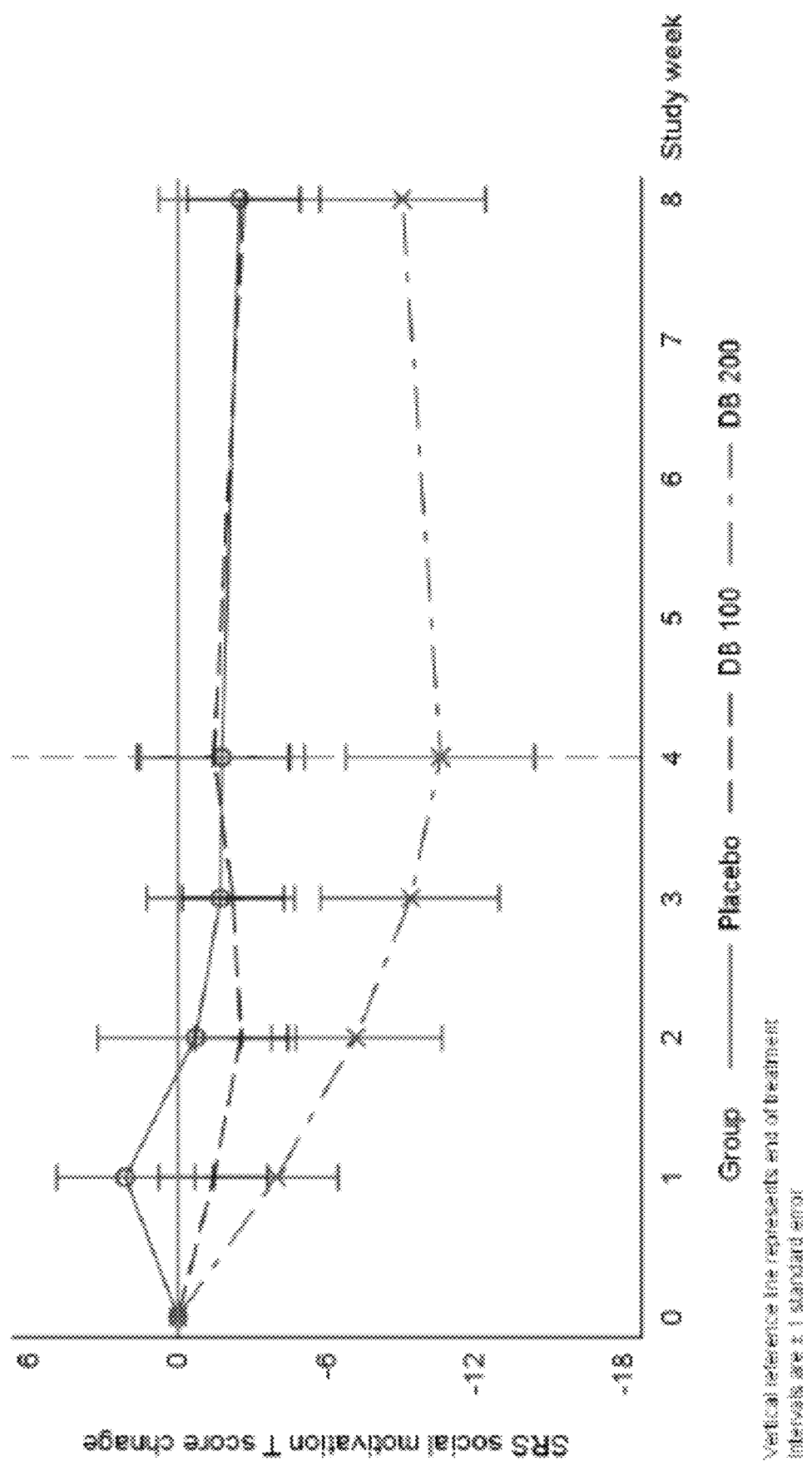
FIG. 21 shows the change from Baseline in SRS-2 Social Motivation T-score, Week 0-Week 8 (ITT Population, Draft).
Figure 22:
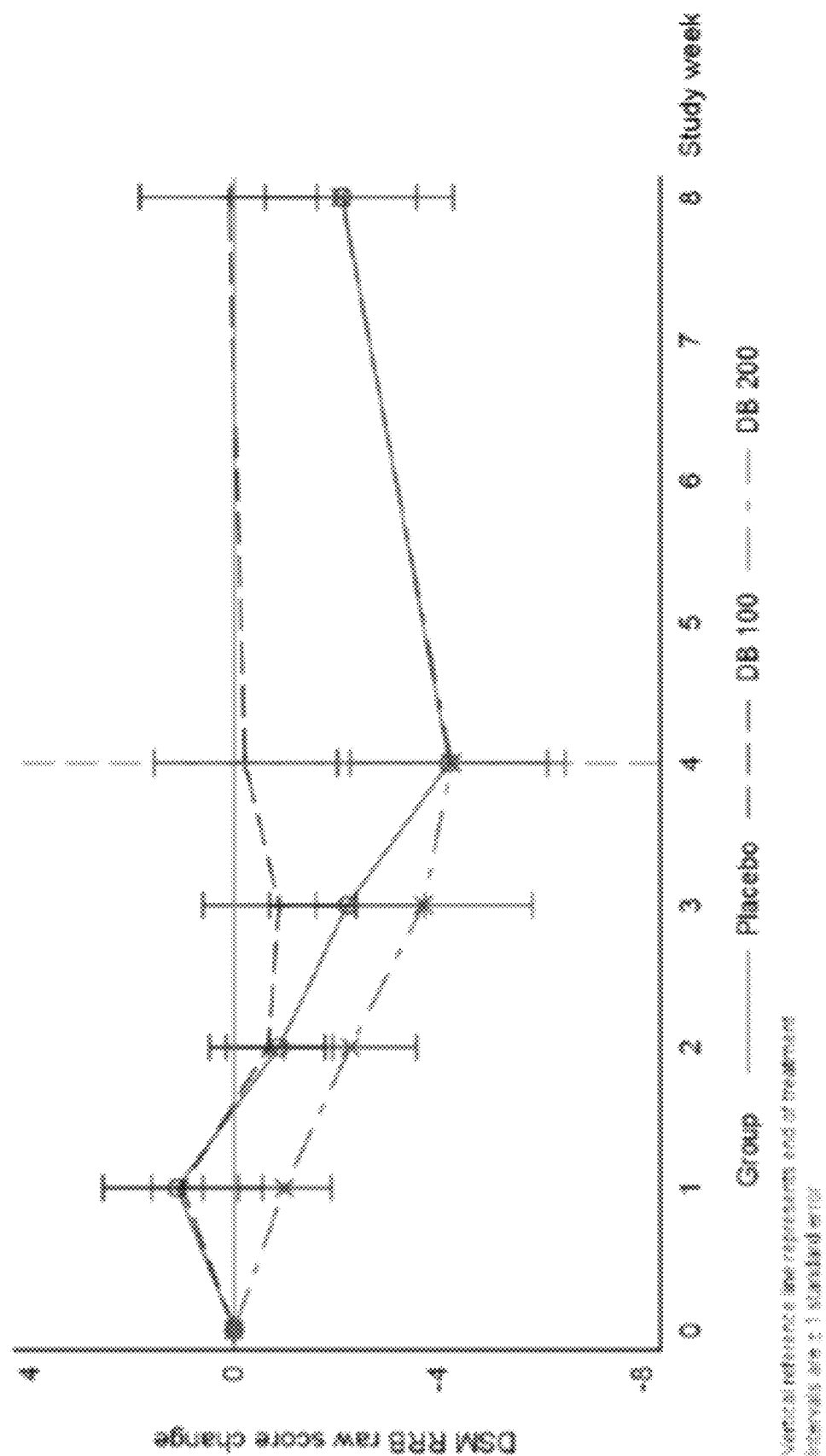
FIG. 22 shows the change from Baseline in SRS-2 DSM-5 Restrictive and Repetitive Behavior, Week 0-Week 8 (ITT Population, Draft).
Figure 23:
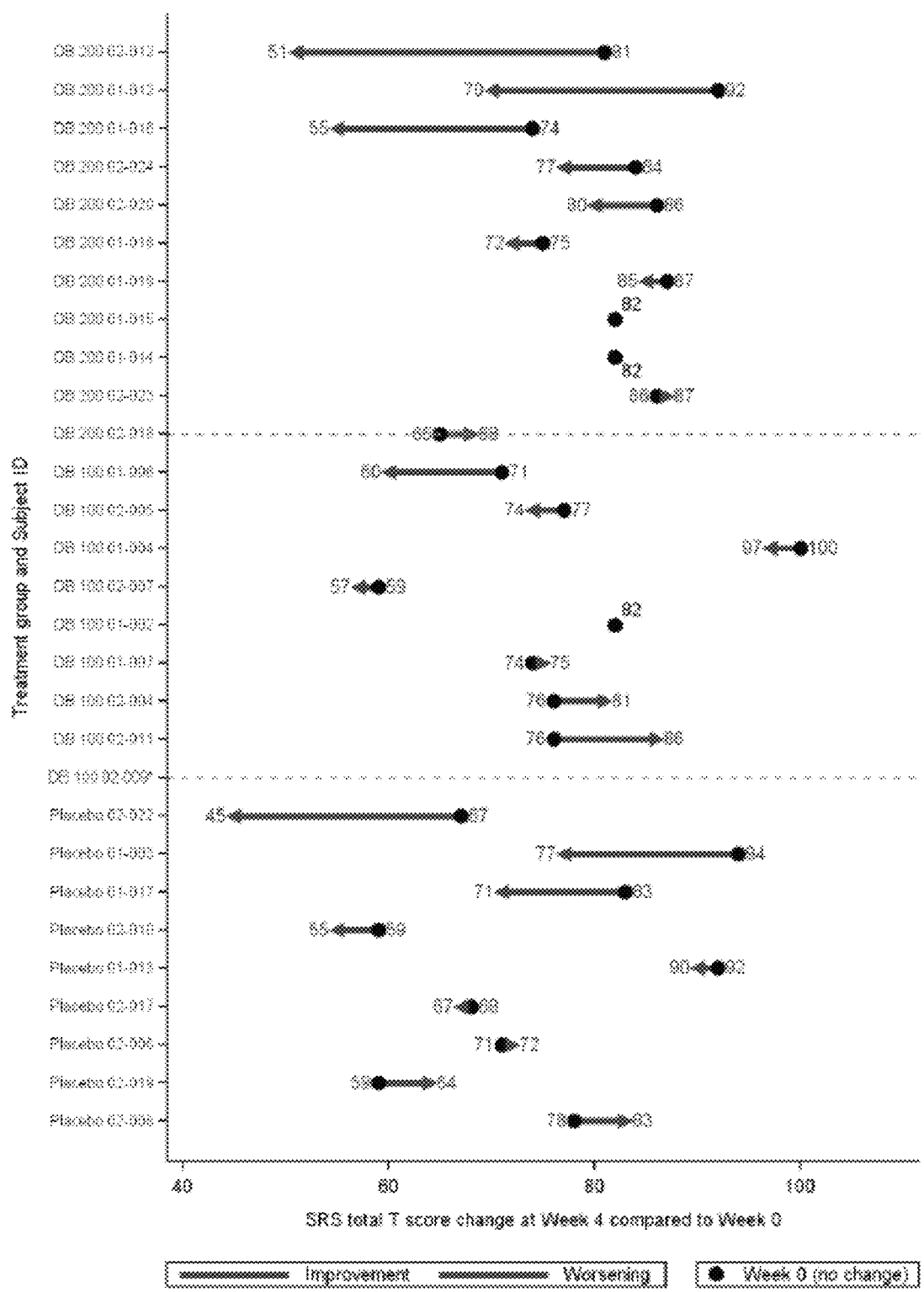
FIG. 23 shows the change in SRS-2 Total T-score from Baseline to Week 4 by Patient (ITT Population, Draft).
Figure 24:
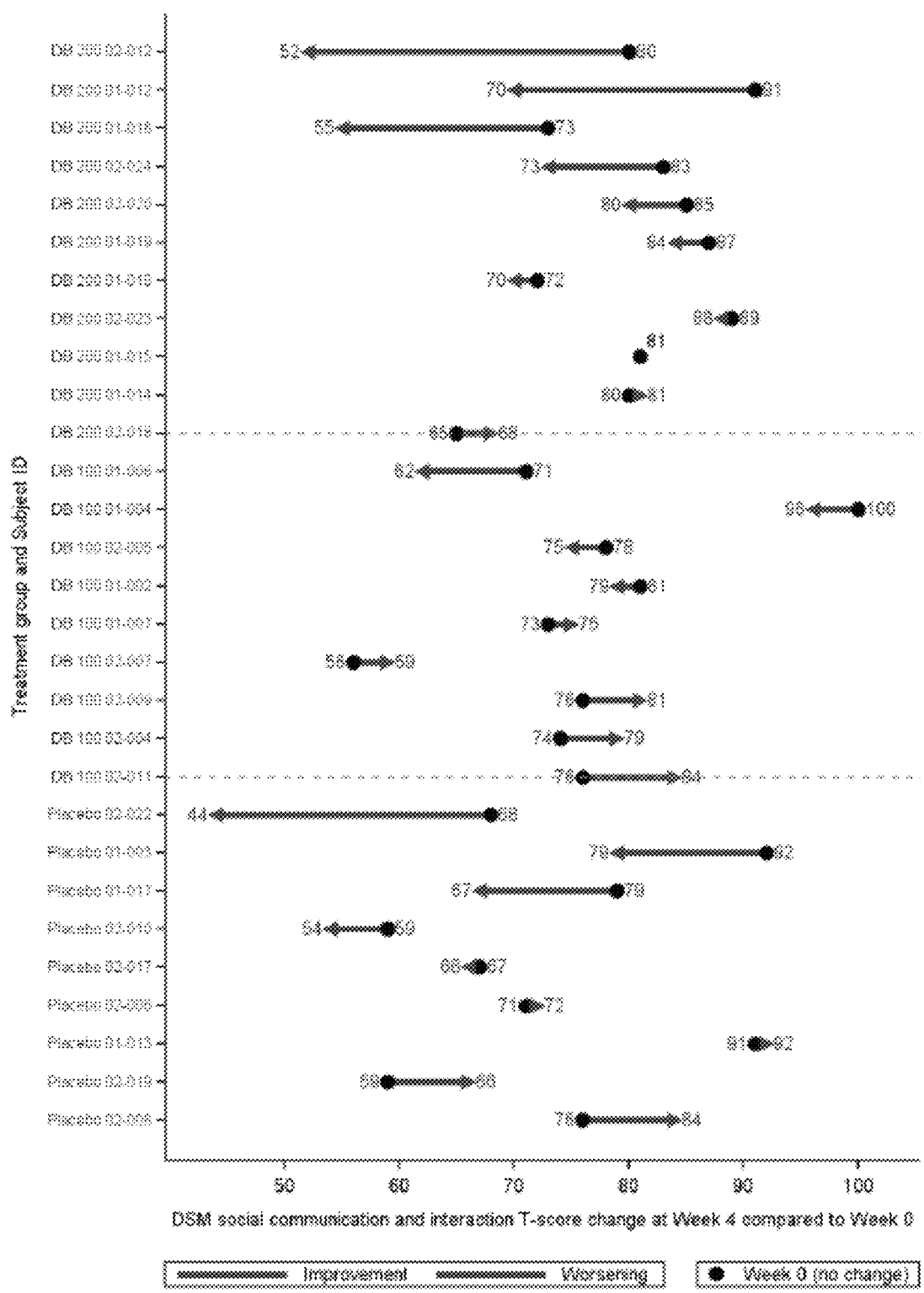
FIG. 24 shows the change in SRS-2 DSM-5 Social Communication and Interaction T-score from Baseline to Week 4 by Patient (ITT Population, Draft).
Figure 25:
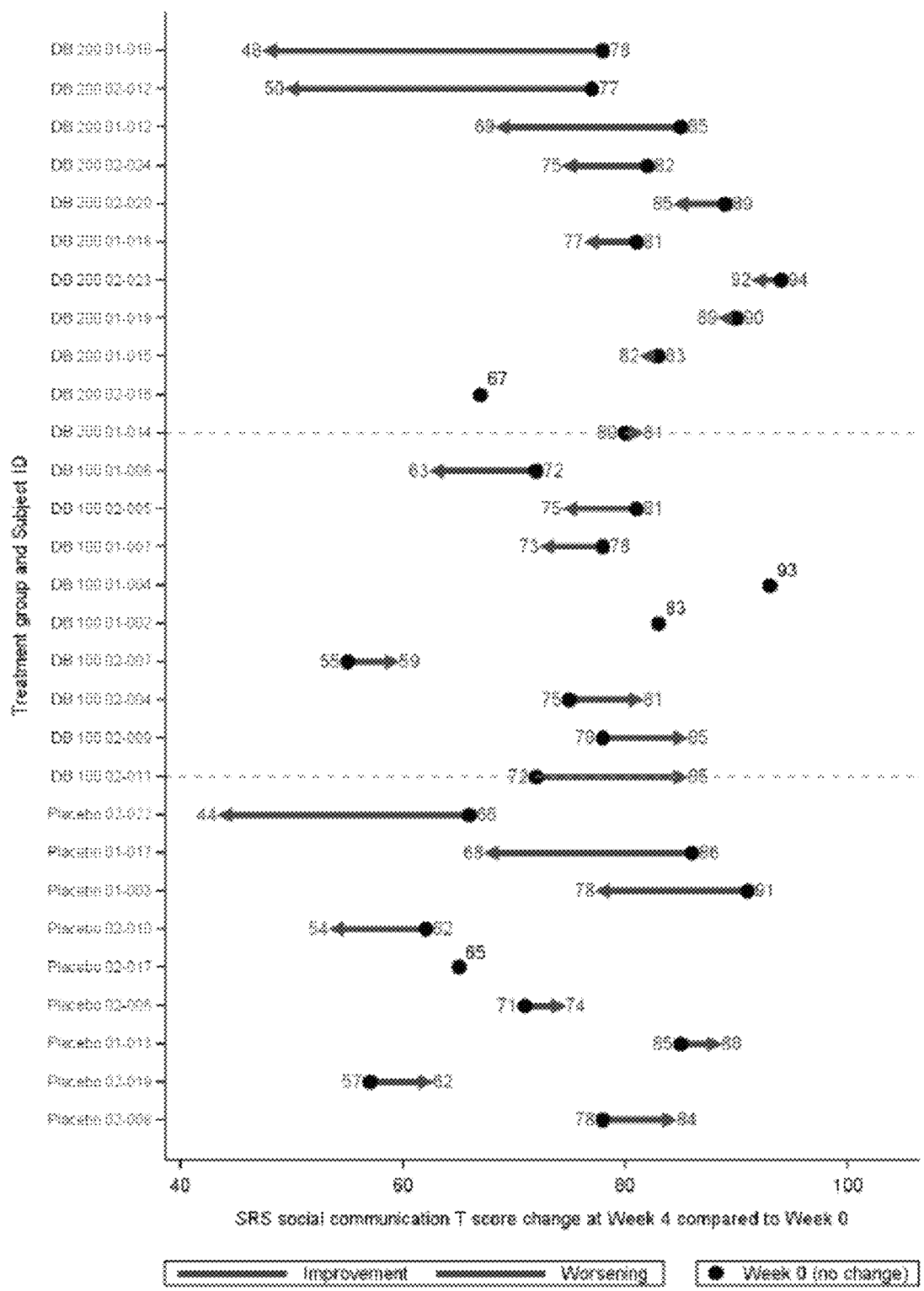
FIG. 25 shows the change in SRS-2 Social Communication T-score from Baseline to Week 4 by Patient (ITT Population, Draft).
Figure 26:
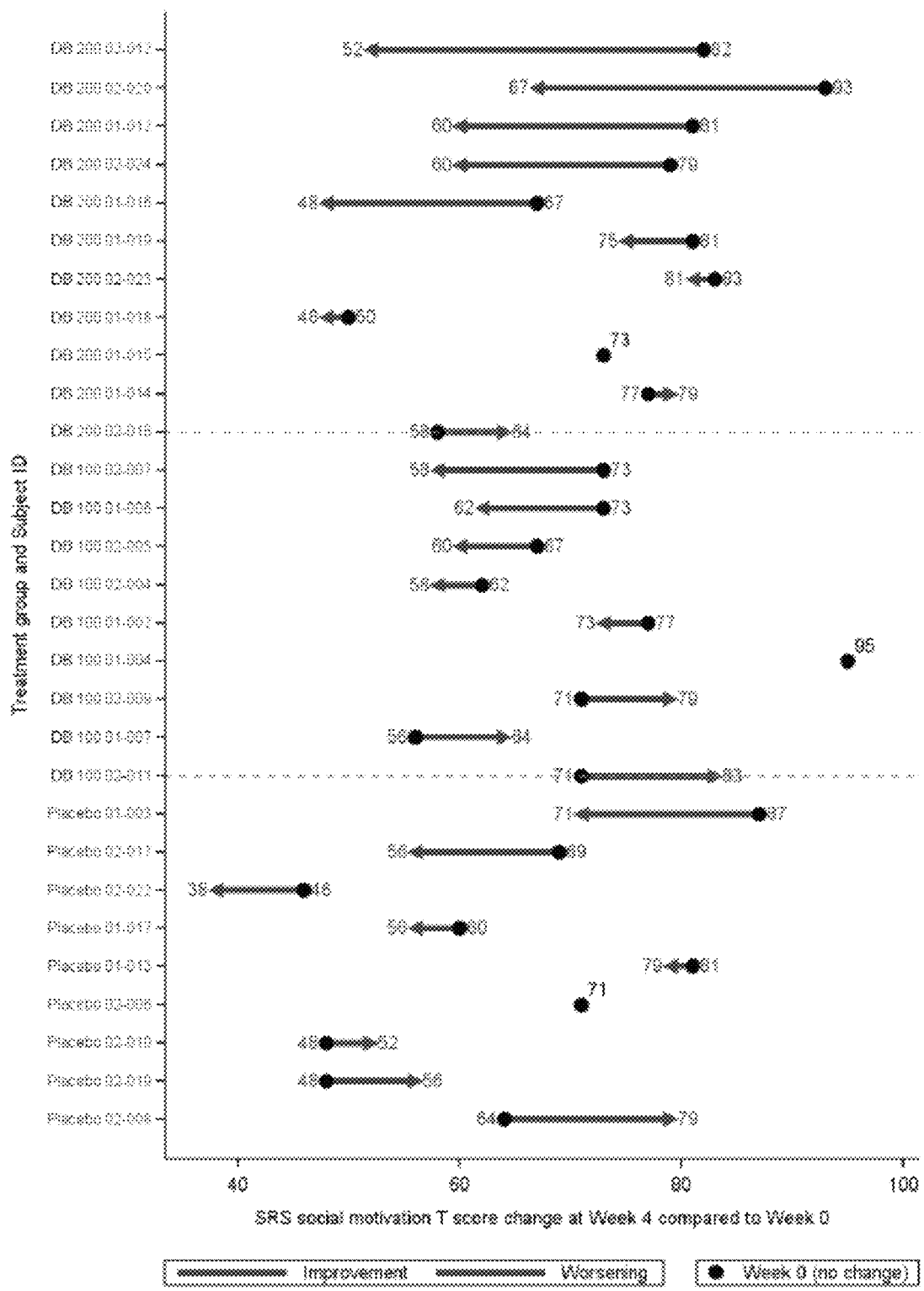
FIG. 26 shows the change in SRS-2 Social Motivation T-score from Baseline to Week 4 by Patient (ITT Population, Draft).
Figure 27:
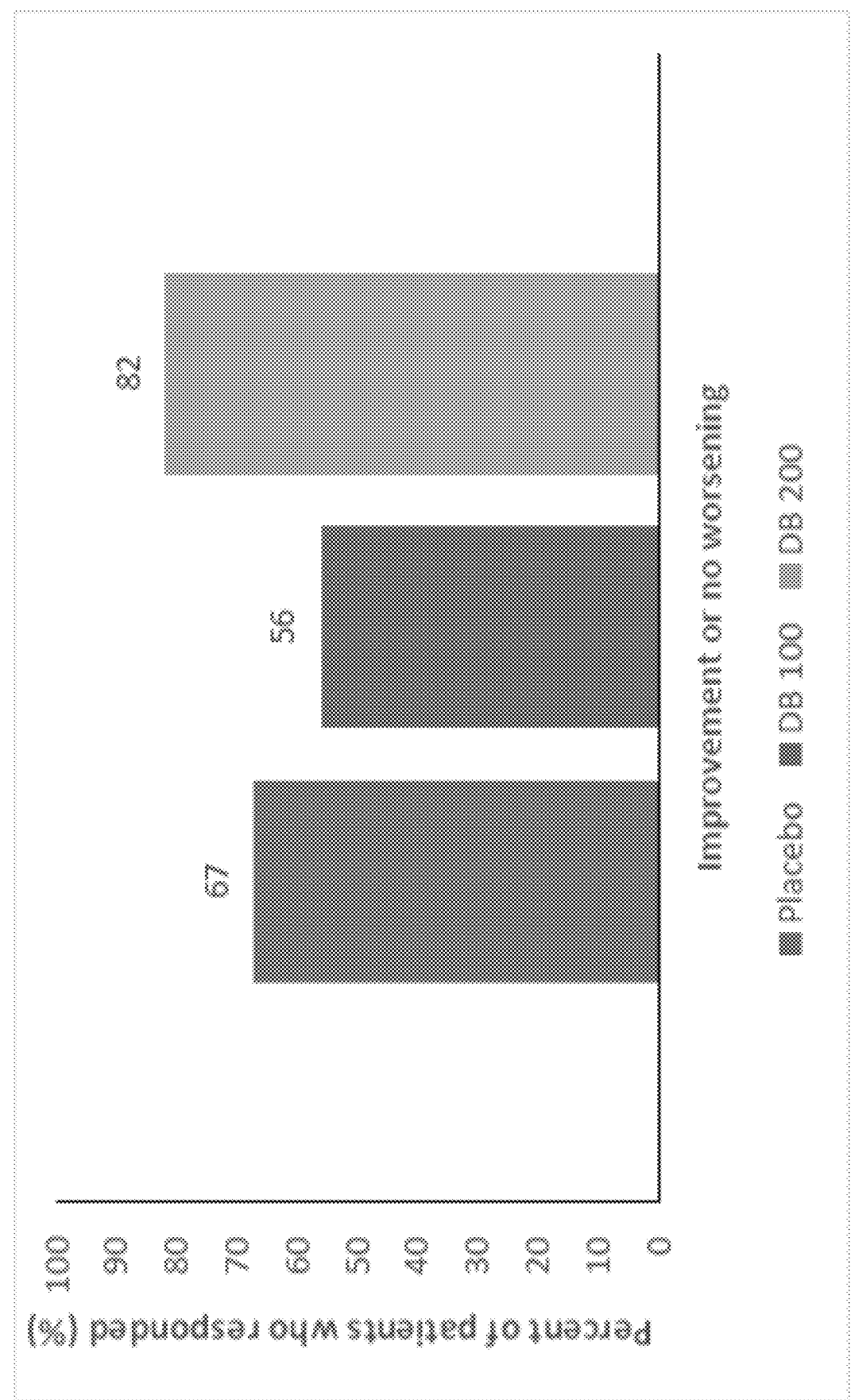
FIG. 27 shows the responder analysis for SRS-2 Total T-score at Week 4/LOCF (ITT Population, Draft).
Figure 28:
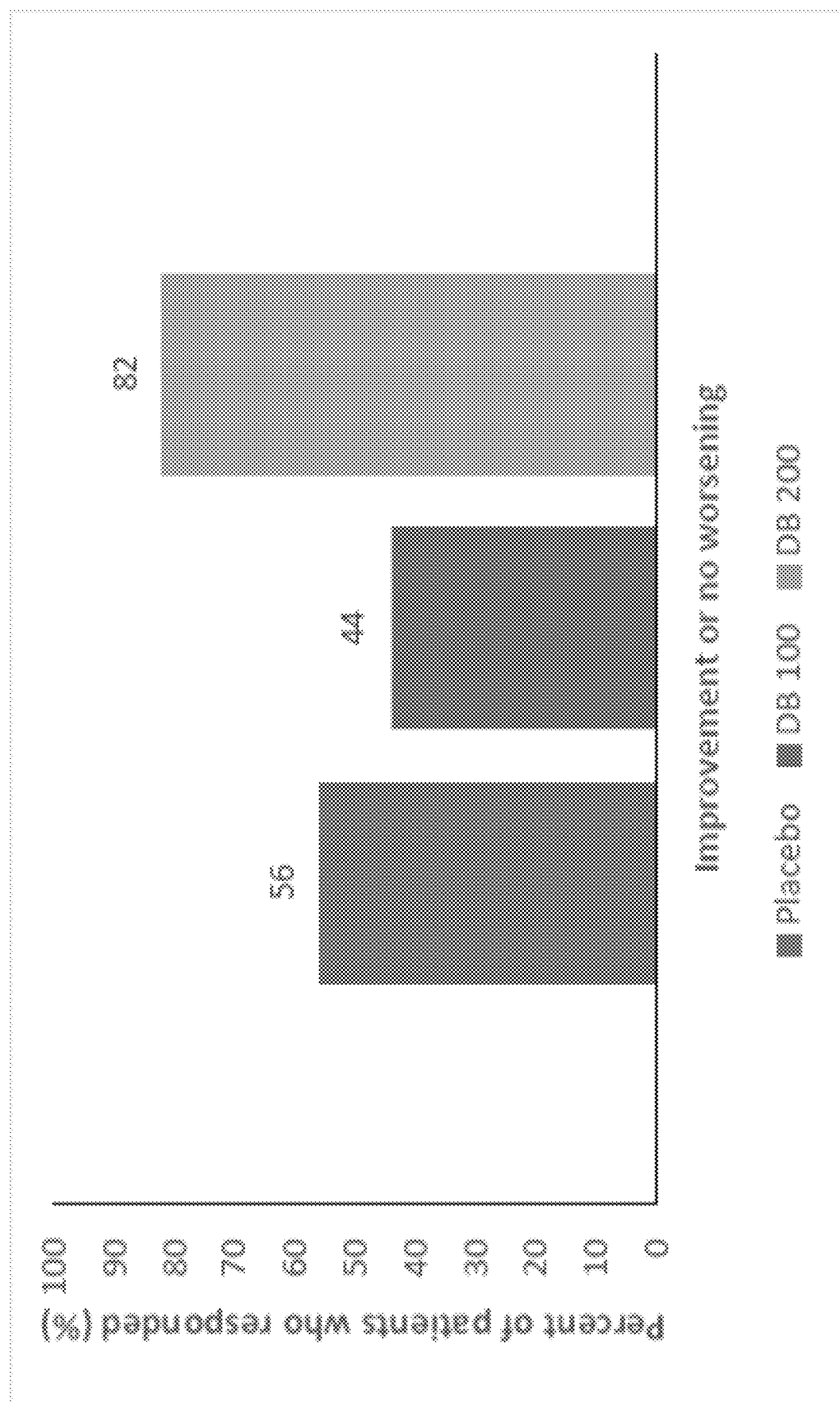
FIG. 28 shows the responder analysis for SRS-2 DSM-5 Social Communication and Interaction T-score at Week 4/LOCF (ITT Population, Draft).
Figure 29:
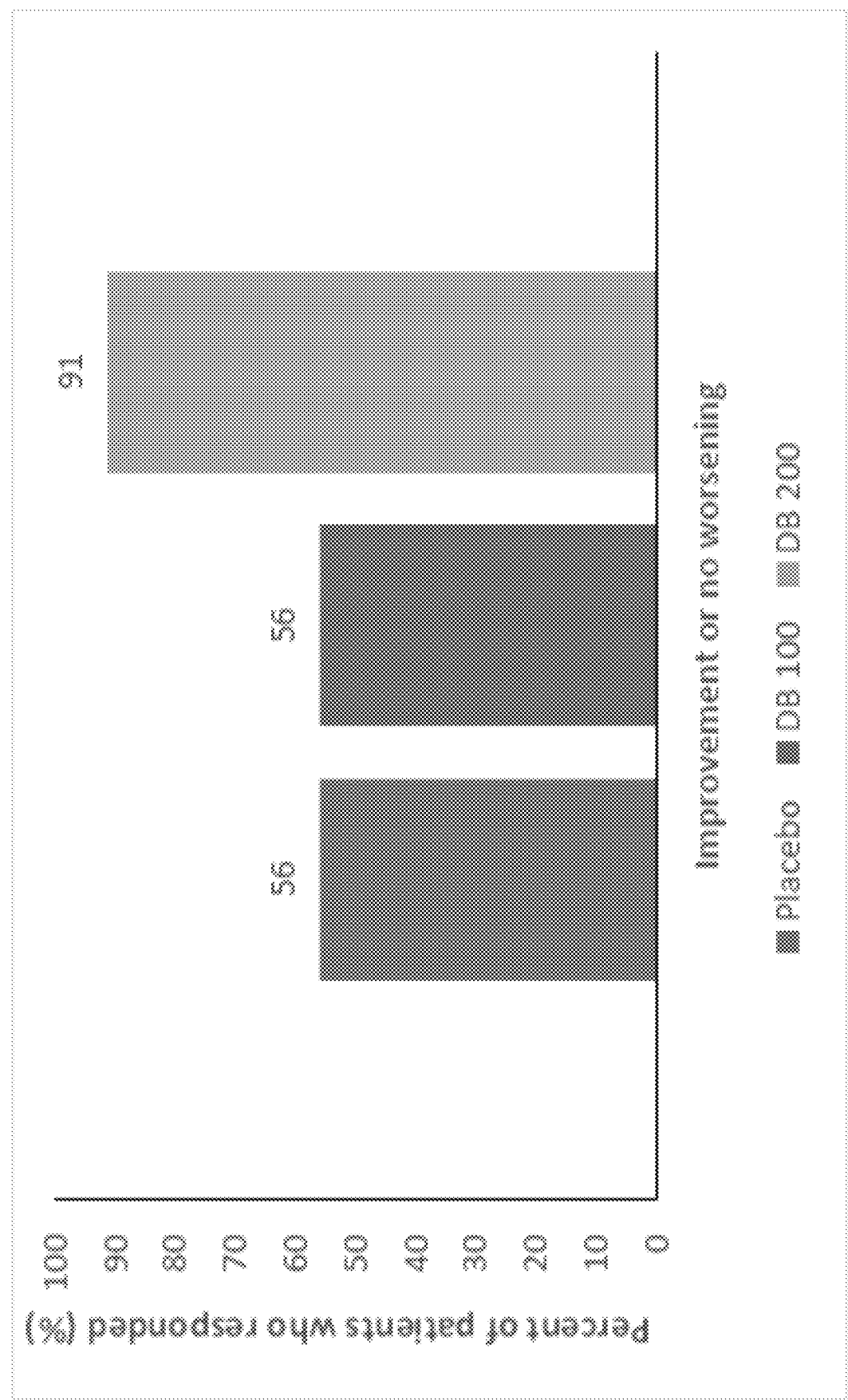
FIG. 29 shows the responder analysis for SRS-2 Social Communication T-score at Week 4/LOCF (ITT Population, Draft).
Figure 30:
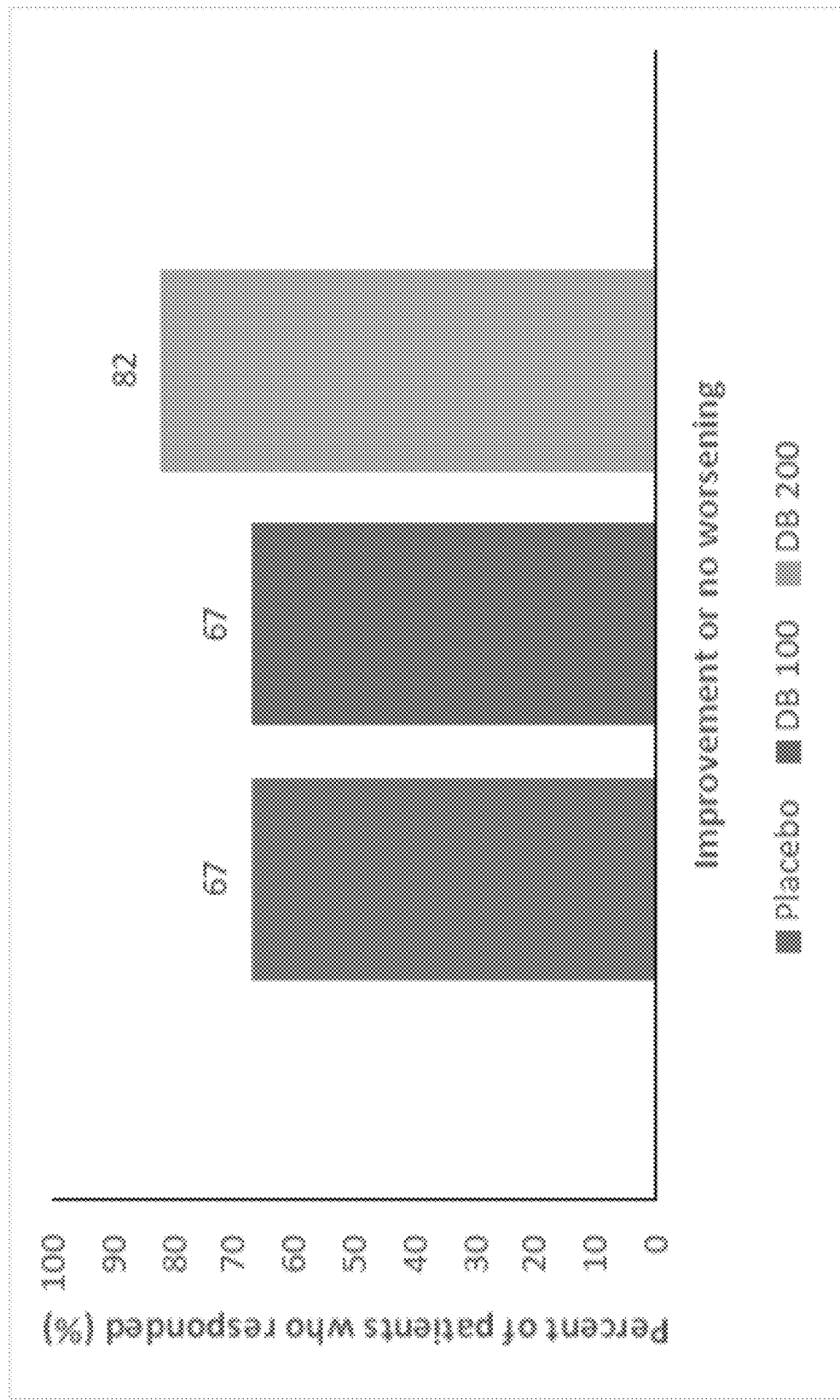
FIG. 30 shows the responder analysis for SRS-2 Social Motivation T-score at Week 4/LOCF (ITT Population, Draft).
Figure 31:
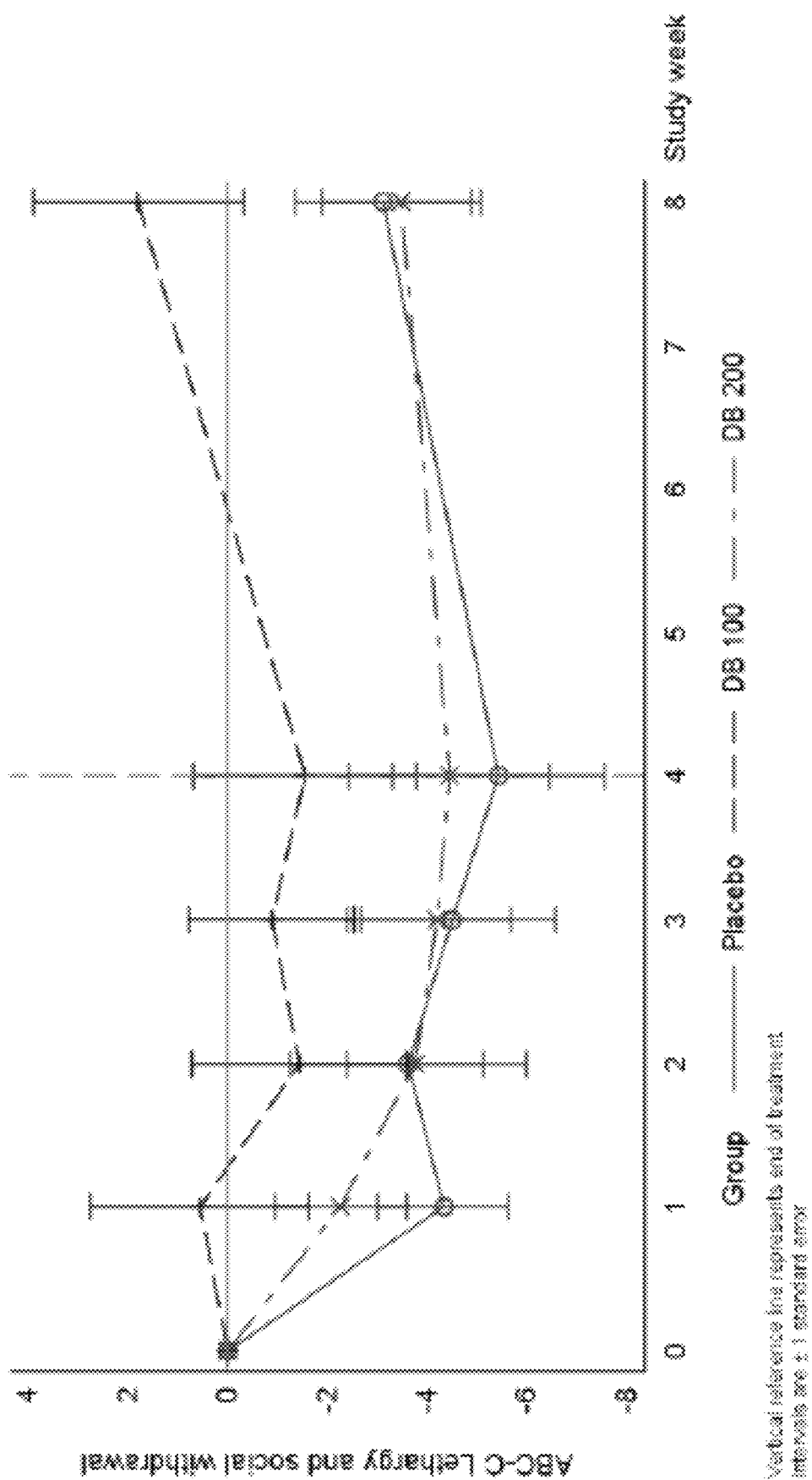
FIG. 31 shows the change from Baseline in ABC-C Lethargy and Social Withdrawal Domain, Week 0-Week 8 (ITT Population, Draft).
Figure 32:
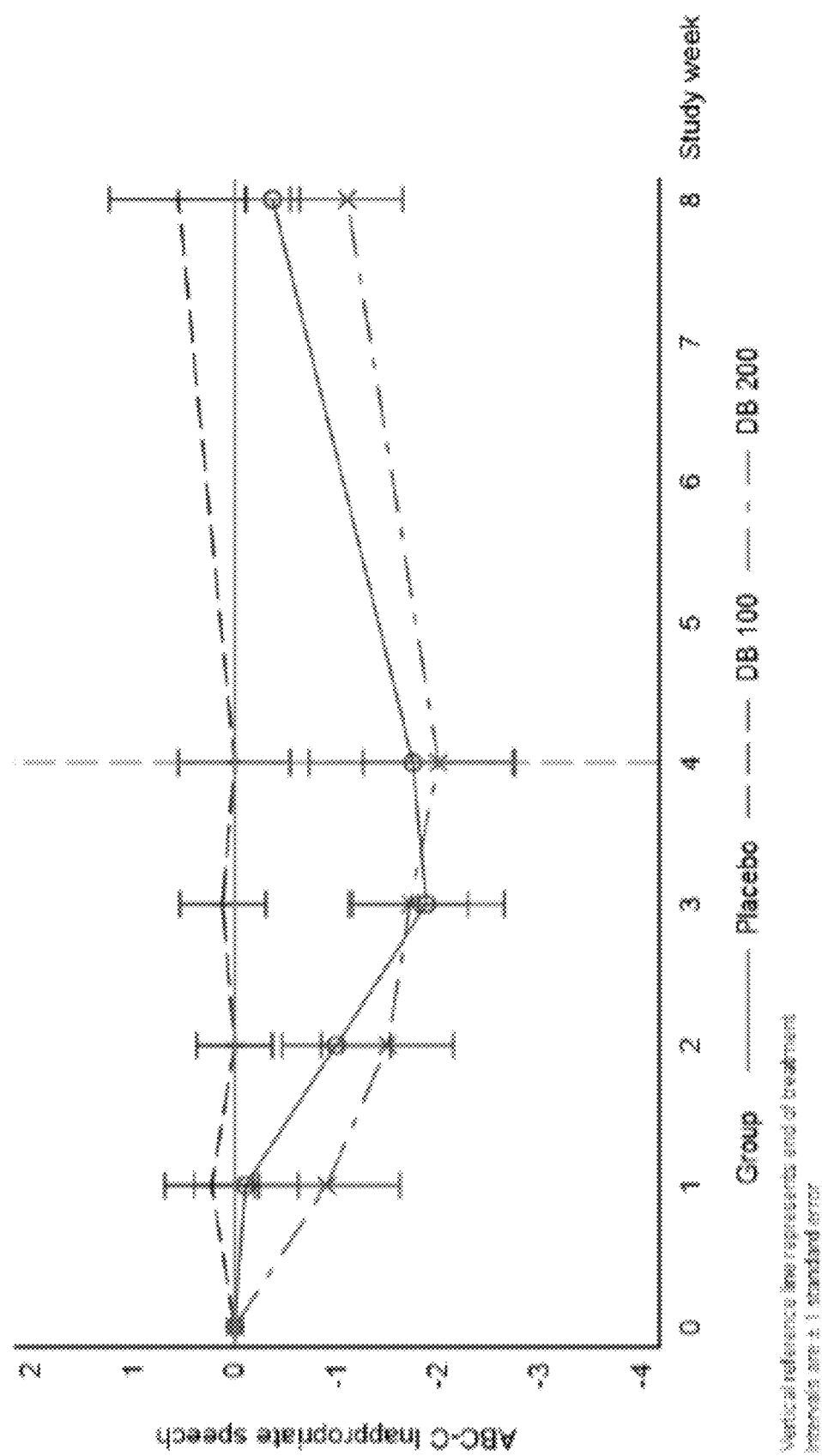
FIG. 32 shows the change from Baseline in ABC-C Inappropriate Speech Domain, Week 0-Week 8 (ITT Population, Draft).
Figure 33:
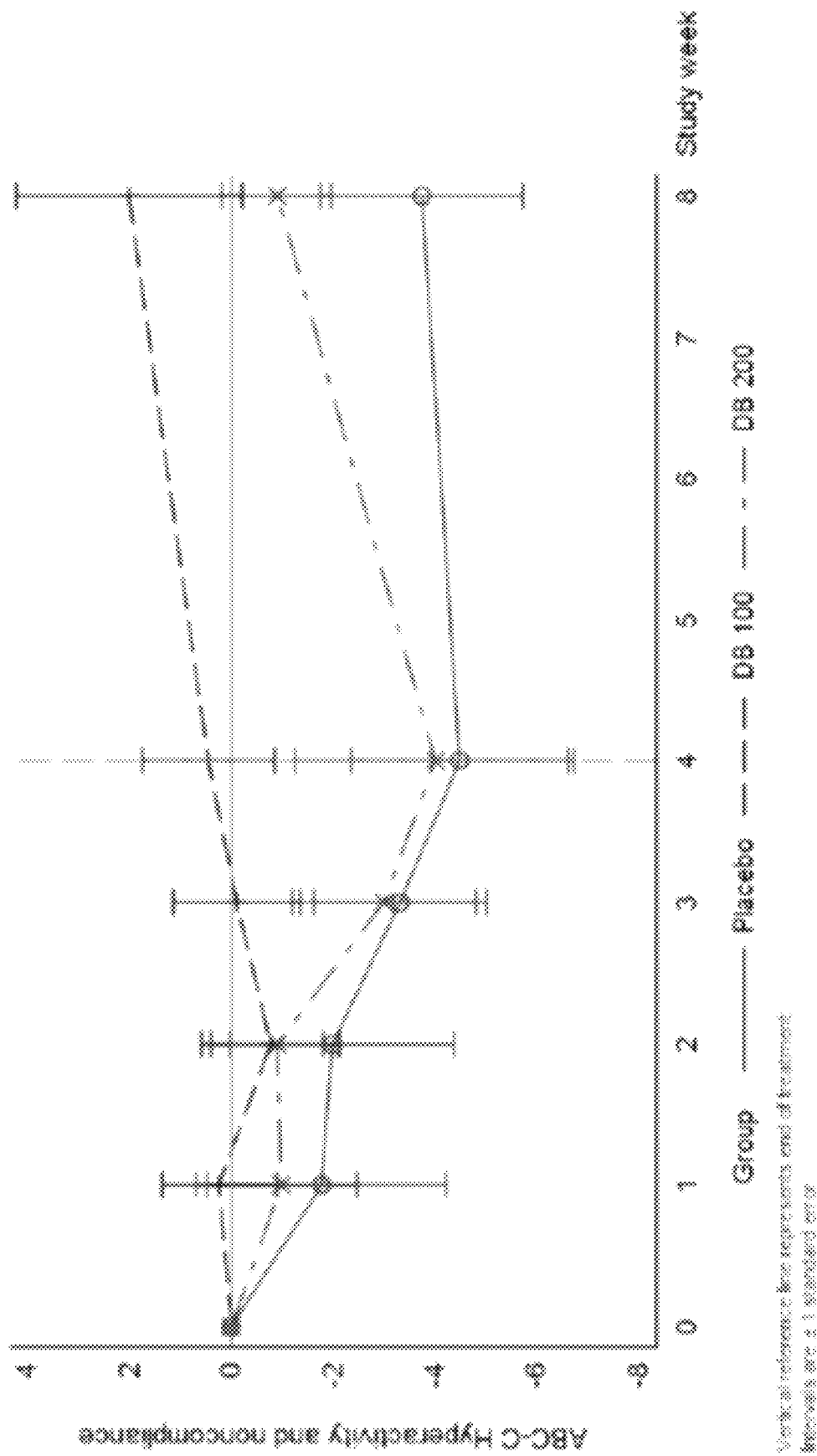
FIG. 33 shows the change from Baseline in ABC-C Hyperactivity and Noncompliance Domain, Week 0-Week 8 (ITT Population, Draft).
Figure 34:
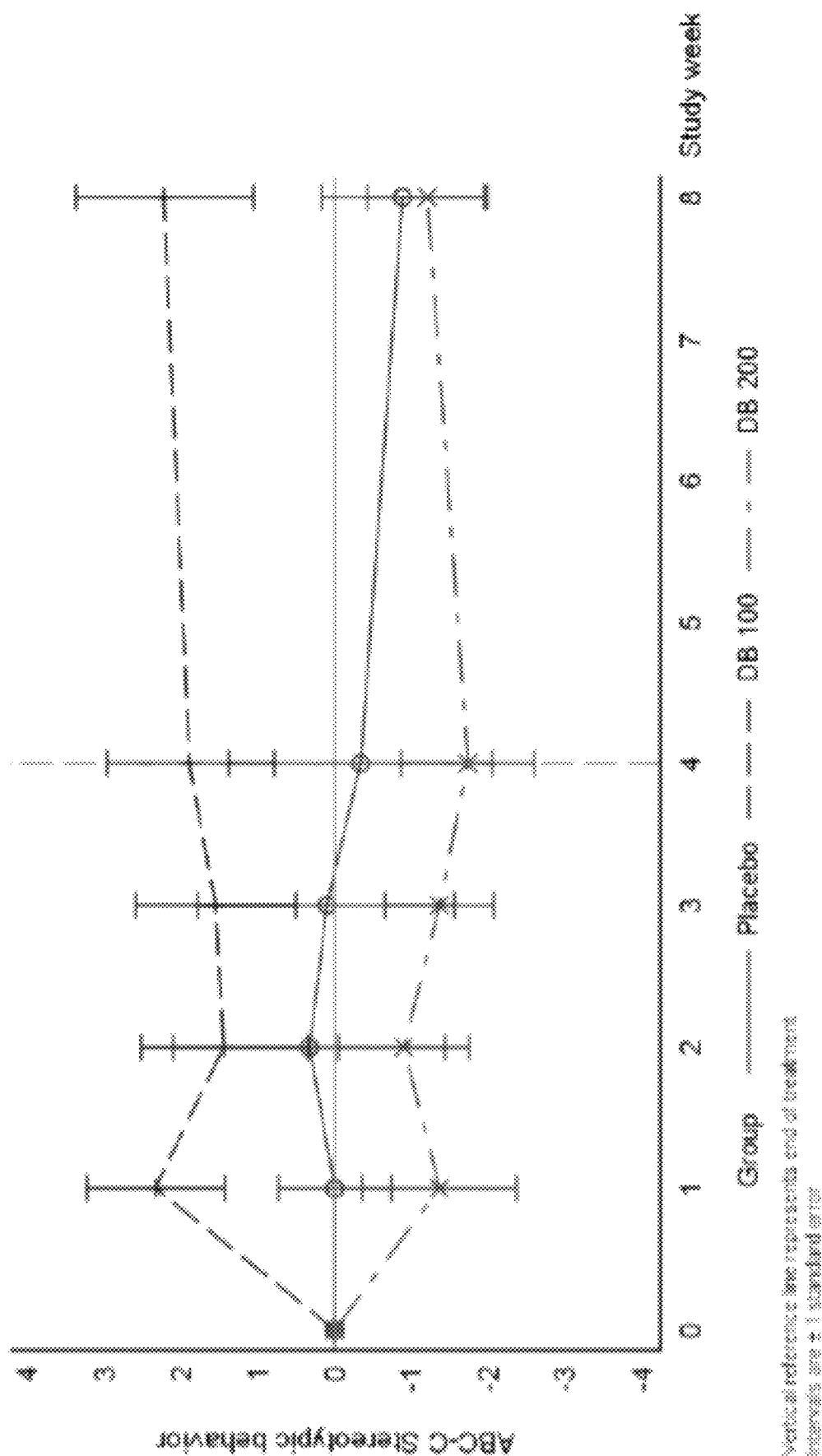
FIG. 34 shows the change from Baseline in ABC-C Stereotypic Behavior Domain, Week 0-Week 8 (ITT Population, Draft).
Figure 35:
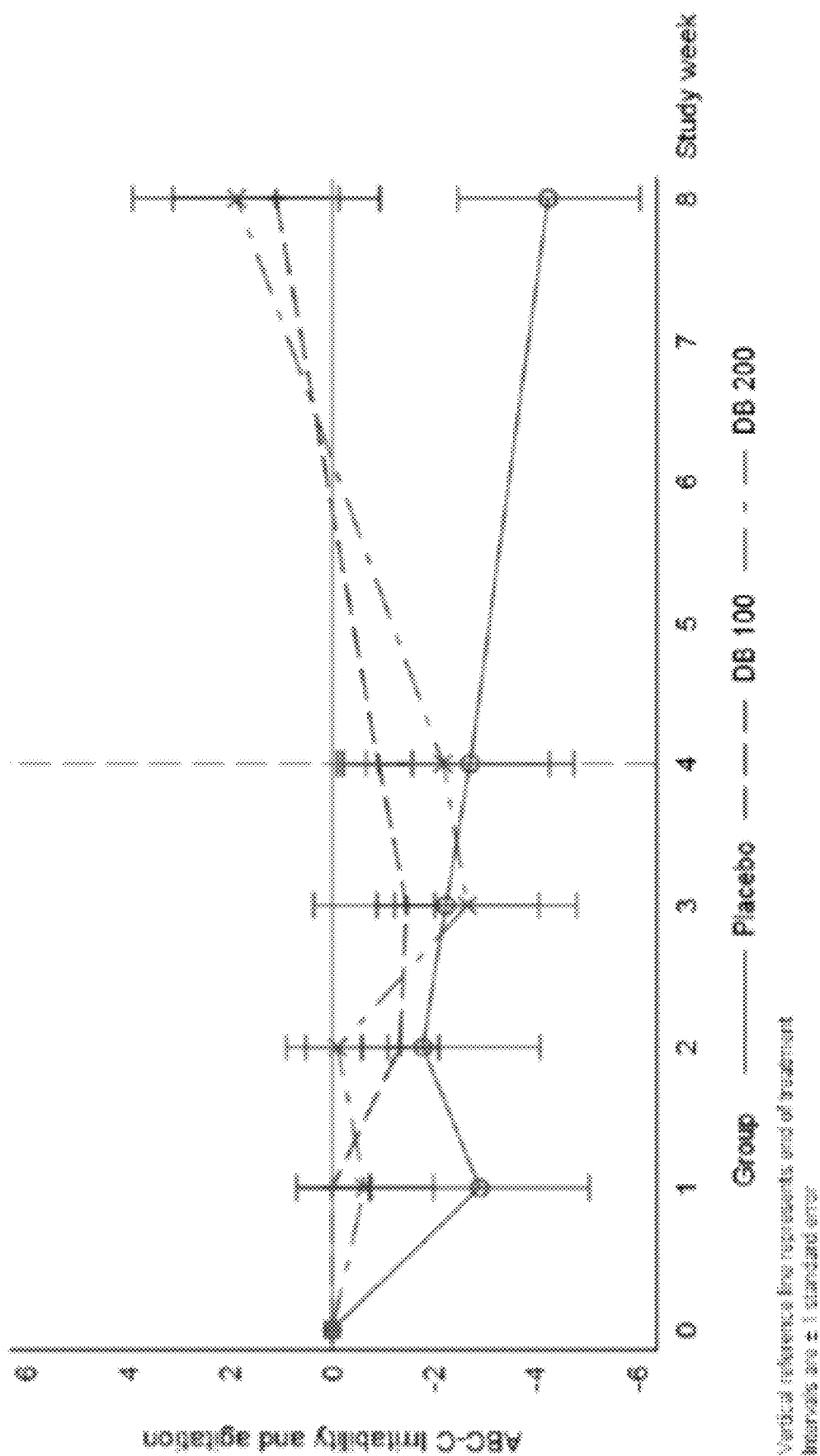
FIG. 35 shows the change from Baseline in ABC-C Irritability and Agitation Domain, Week 0-Week 8 (ITT Population, Draft).

The consistency of this effect across multiple patients is suggested by the summary of the change in ADOS-2 Total Score from Screening to Week 4 displayed in FIG. 17.

Social Responsiveness Scale, Second Edition (SRS-2)

The change from Baseline in SRS-2 Total T-score, SRS-2 DSM-5 Social, Communication and Interaction T-score, SRS-2 Social Communication T-score, SRS-2 Social-Motivation T-score and SRS-2 DSM-5 Restrictive and Repetitive Behavior T-score for L1-79 compared to placebo over time are displayed graphically in FIG. 18, FIG. 19, FIG. 20, FIG. 21 and FIG. 22, respectively.

The SRS-2 Total, SRS-2 DSM-5 Social Communication and Interaction, SRS-2 Social Communication and SRS-2 Social Motivation T-scores improved by close to 8 points or more on average in the L1-79 200 mg treated group (FIG. 18, FIG. 19, FIG. 20 and FIG. 21). The Social Communication and Interaction scale are comprised of the DSM-5 criteria that make up the social communication and social interaction deficits required for the diagnosis of ASD. Of considerable interest is the finding that patients with baseline scores between 60 and 83 who dropped by 8 points or more were likely to demonstrate categorical changes in clinical severity, since the classifications of "Within Normal Limits" (below 60 T-score), "Mild Range" (60 to 65 T-score), "Moderate Range" (66 to 75 T-score) and "Severe Range" (76 T-score or greater) of symptom severity are defined within those T-score ranges.

A summary of the change in SRS-2 Total T-score, SRS-2 DSM-5 Social, Communication and Interaction T-score, SRS-2 Social Communication T-score, and SRS-2 Social-Motivation T-score from baseline to Week 4 for each patient are displayed in FIG. 23, FIG. 24, FIG. 25, and FIG. 26, respectively.

For SRS-2 Total, SRS-2 DSM-5 Social Communication and Interaction, SRS-2 Social Communication, and SRS-2 Social Motivation T-scores, both the magnitude and number of responders observed were greater with L1-79 200 mg, compared to placebo (FIG. 27, FIG. 28, FIG. 29 and FIG. 30). For the SRS-2 Total T-Score, 3 patients had sufficient improvement to change categories of severity in the L1-79 200 mg group, compared to 2 in both the L1-79 100 mg and placebo groups. For the SRS-2 Social Motivation T-score, 6 patients demonstrated categorical changes in clinical severity in the L1-79 200 mg group, compared to 4 and 3 patients in the 100 mg and placebo groups, respectively. For the SRS-2 DSM-5 Social, Communication and Interaction T-score, 4 patients had changes in severity categorization in the 200 mg group, compared to 2 and 3 patients in the 100 mg and placebo groups, respectively. Similarly, for the SRS-2 Social Communication T-score, 4 patients demonstrated categorical improvement in the 200 mg group, compared to 3 in both the placebo and 100 mg groups.

Responder analyses (defined as an improvement or no worsening) are presented for SRS-2 Total T-score, SRS-2 DSM-5 Social, Communication and Interaction T-score, SRS-2 Social Communication T-score, and SRS-2 Social- Motivation T-score at Week 4 or LOCF in FIG. 27, FIG. 28, FIG. 29, and FIG. 30, respectively.

FIGS. 27-30 demonstrate that the percent of responders (as defined by improvement or no worsening were greater with L1-79 200 mg, compared to placebo; see Responder Definition (section above).

Aberrant Behavior Checklist-Community (ABC-C)

The change from Baseline in ABC-C Lethargy and Social Withdrawal Domain, ABC-C Inappropriate Speech Domain, ABC-C Hyperactivity and Noncompliance Domain, ABC-C Stereotypic Behavior Domain and ABC-C Irritability and Agitation Domain for L1-79 compared to placebo over time are displayed graphically in FIG. 31, FIG. 32, FIG. 33, FIG. 34 and FIG. 35, respectively.

Figure 36:
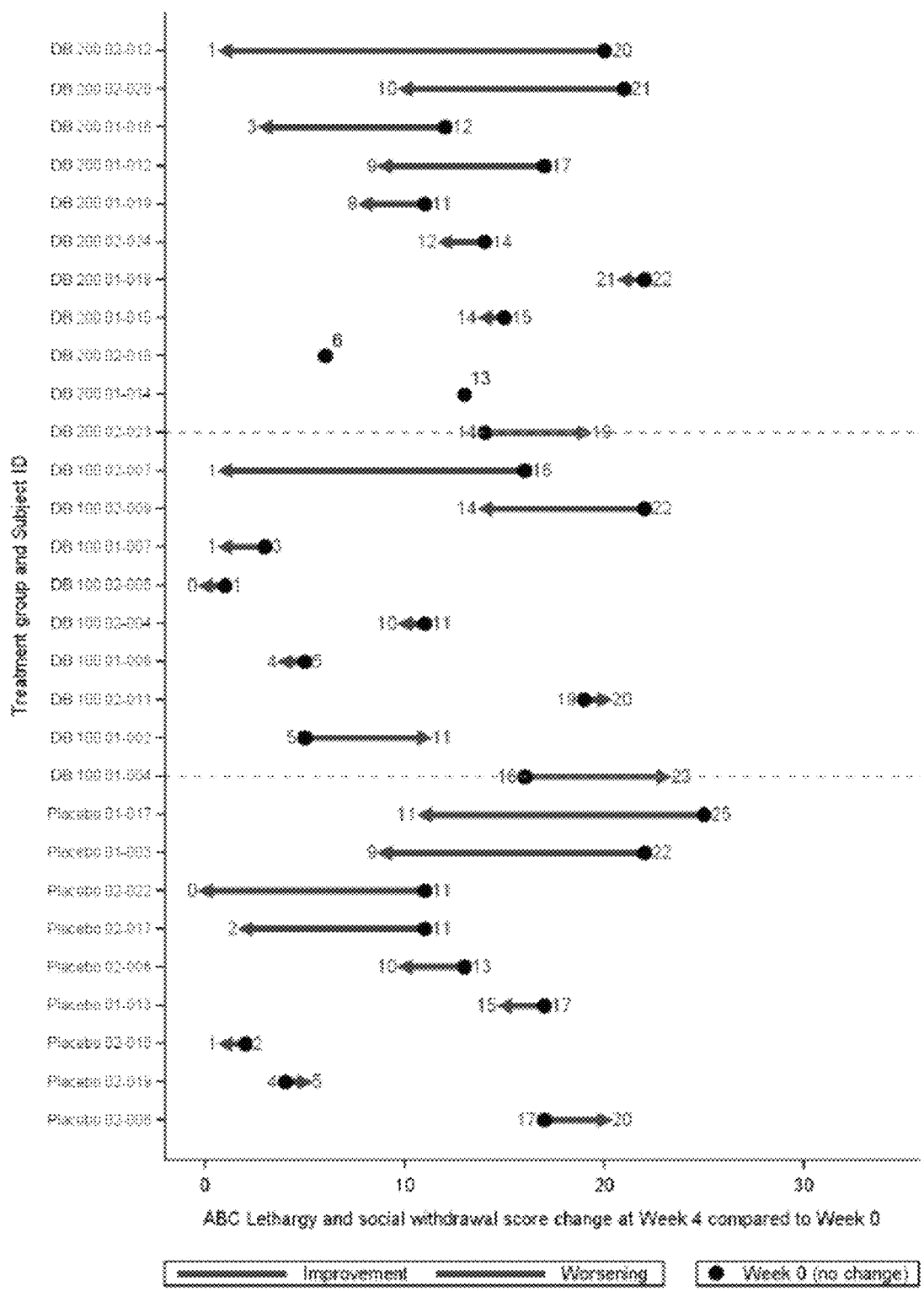
FIG. 36 shows the change in ABC-C Lethargy and Social Withdrawal Domain from Baseline to Week 4 by Patient (ITT Population, Draft).
Figure 37:
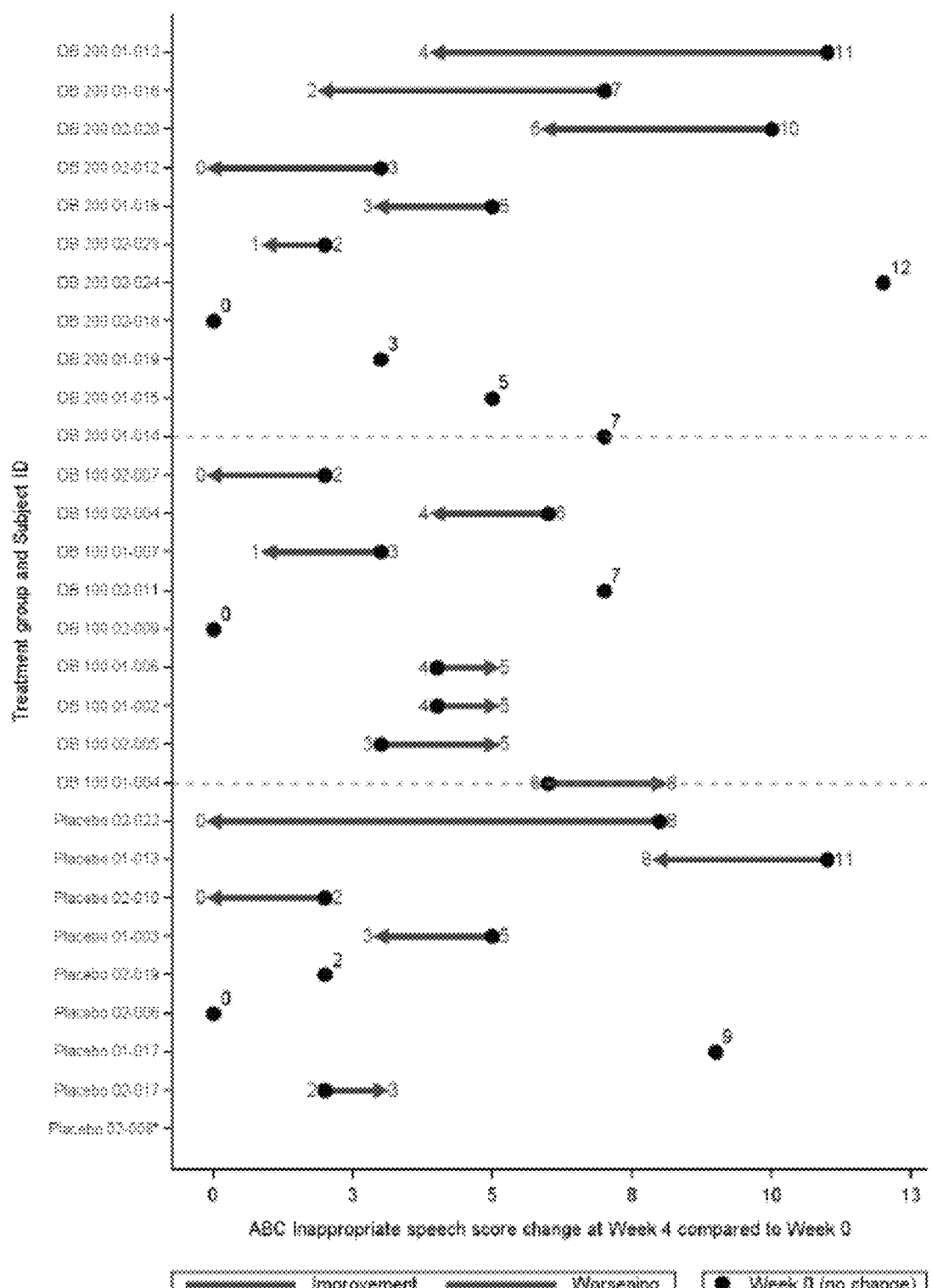
FIG. 37 shows the change in ABC-C Inappropriate Speech Domain from Baseline to Week 4 by Patient (ITT Population, Draft).
Figure 38:
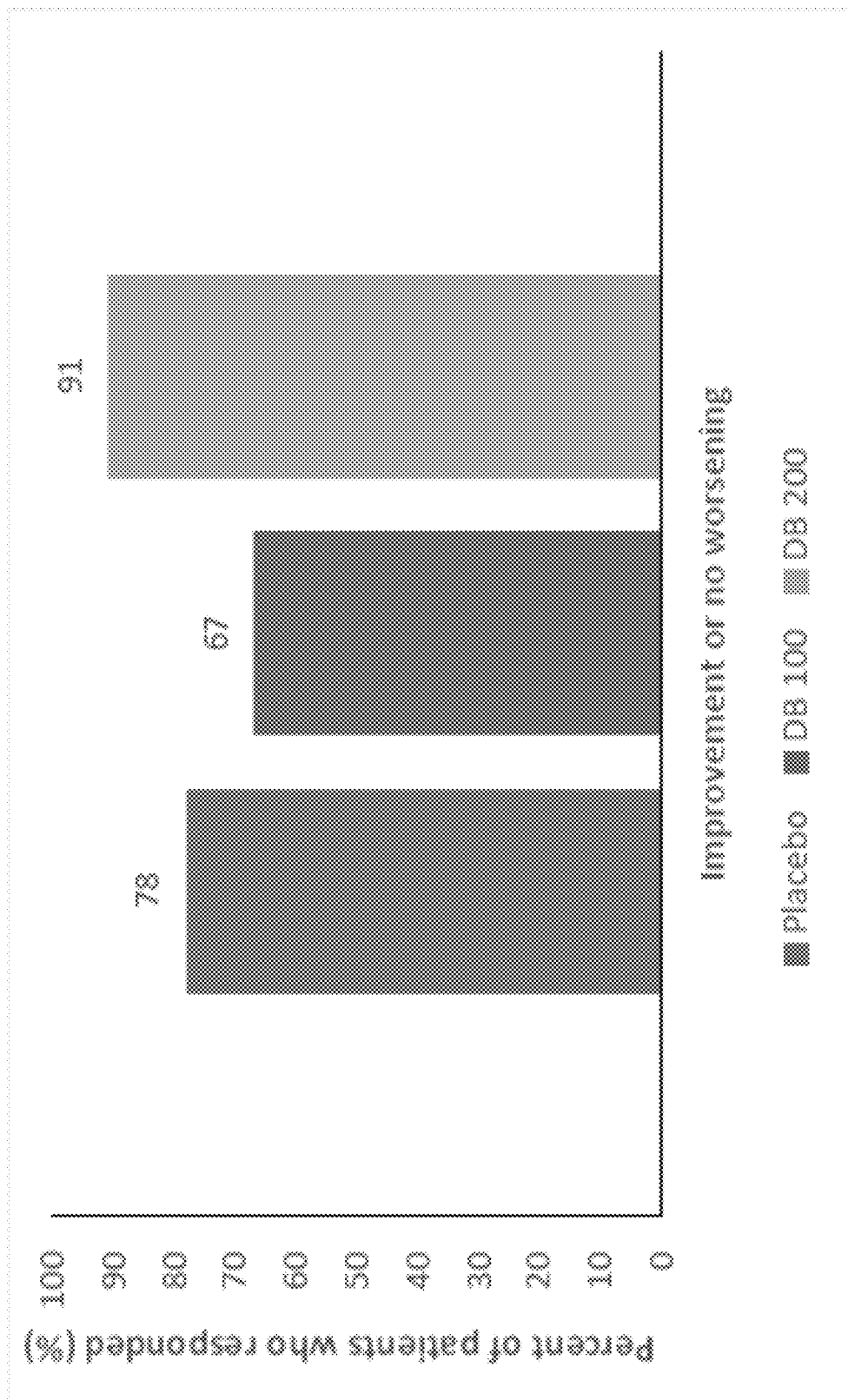
FIG. 38 shows the responder analysis for ABC-C Lethargy and Social Withdrawal Domain at Week 4/LOCF (ITT Population, Draft).
Figure 39:
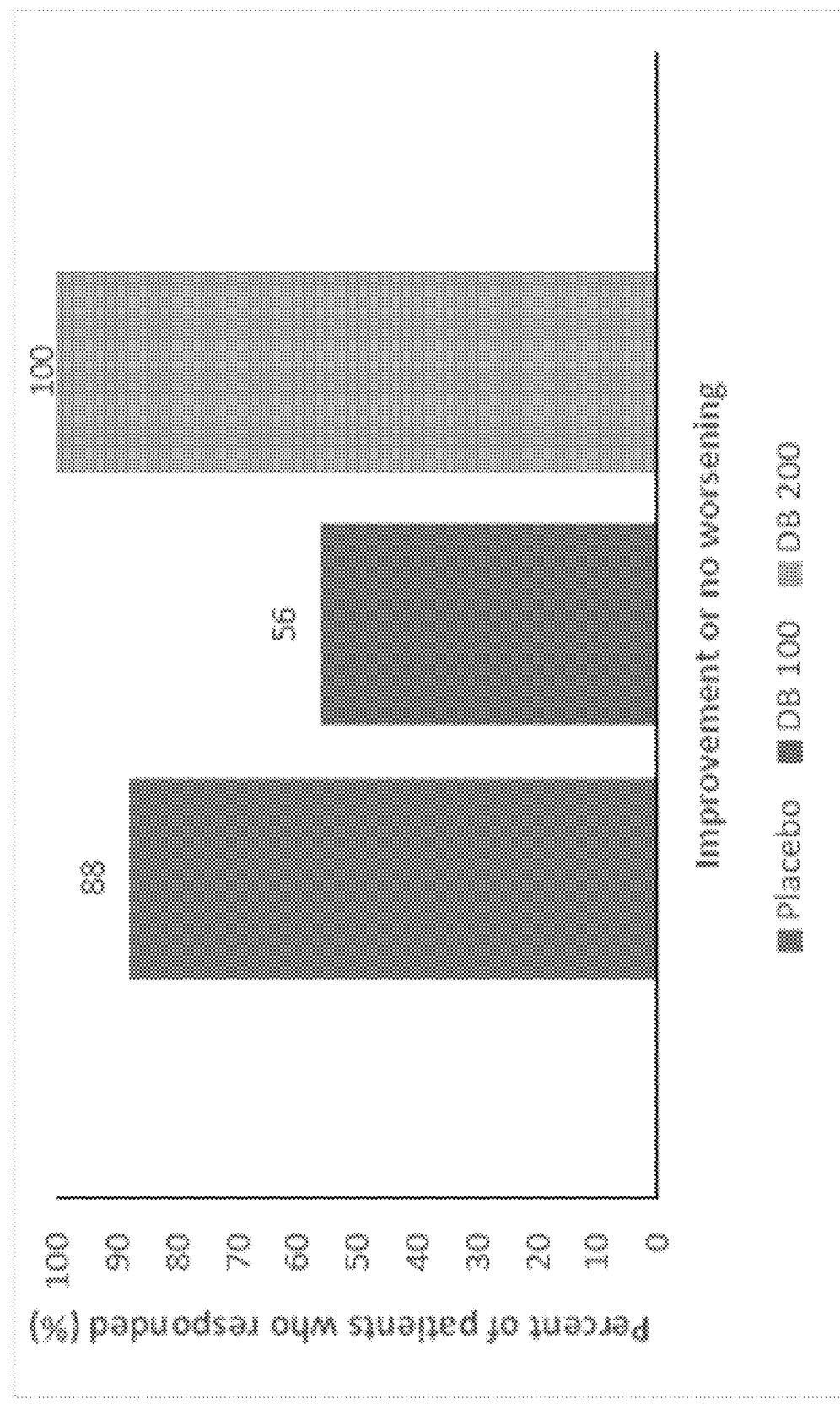
FIG. 39 shows the responder Analysis for ABC-C Inappropriate Speech Domain at Week 4/LOCF (ITT Population, Draft).

A summary of the change in ABC-C Lethargy and Social Withdrawal Domain and ABC-C Inappropriate Speech Domain from Baseline to Week 4 are displayed by patient in FIG. 36 and FIG. 37, respectively. While there was no separation between the 200 mg and placebo groups in mean change from baseline scores, responder analyses did demonstrate a greater tendency for patients to respond with improvement or no worsening of behaviors in the 200 mg group compared to placebo, as shown in FIG. 38 and FIG. 39, respectively.

As with the SRS-2, both the number of responders and magnitude of response for those patients given L1-79 200 mg demonstrated a trend toward separation for the social and speech domains of the ABC-C. Equally notable was the observation that 90 to 100% of patients with L1-79 200 mg demonstrated stability or improvement of these domains, which are known to vary significantly in intensity over shorter periods of time.

Repetitive Behavior Scale-Revised (RBS-R)

The change from Baseline in RBS-R Total Score, RBS-R Restrictive Behavior, RBS-R Ritualistic Behavior, RBS-R Sameness Behavior, RBS-R Compulsive Behavior, RBS-R Stereotypic Behavior, and RBS-R Self-injurious Behavior for L1-79 compared to placebo over time is displayed graphically in FIG. 40, FIG. 41, FIG. 42, FIG. 43, FIG. 44, FIG. 45, and FIG. 46.

Figure 40:
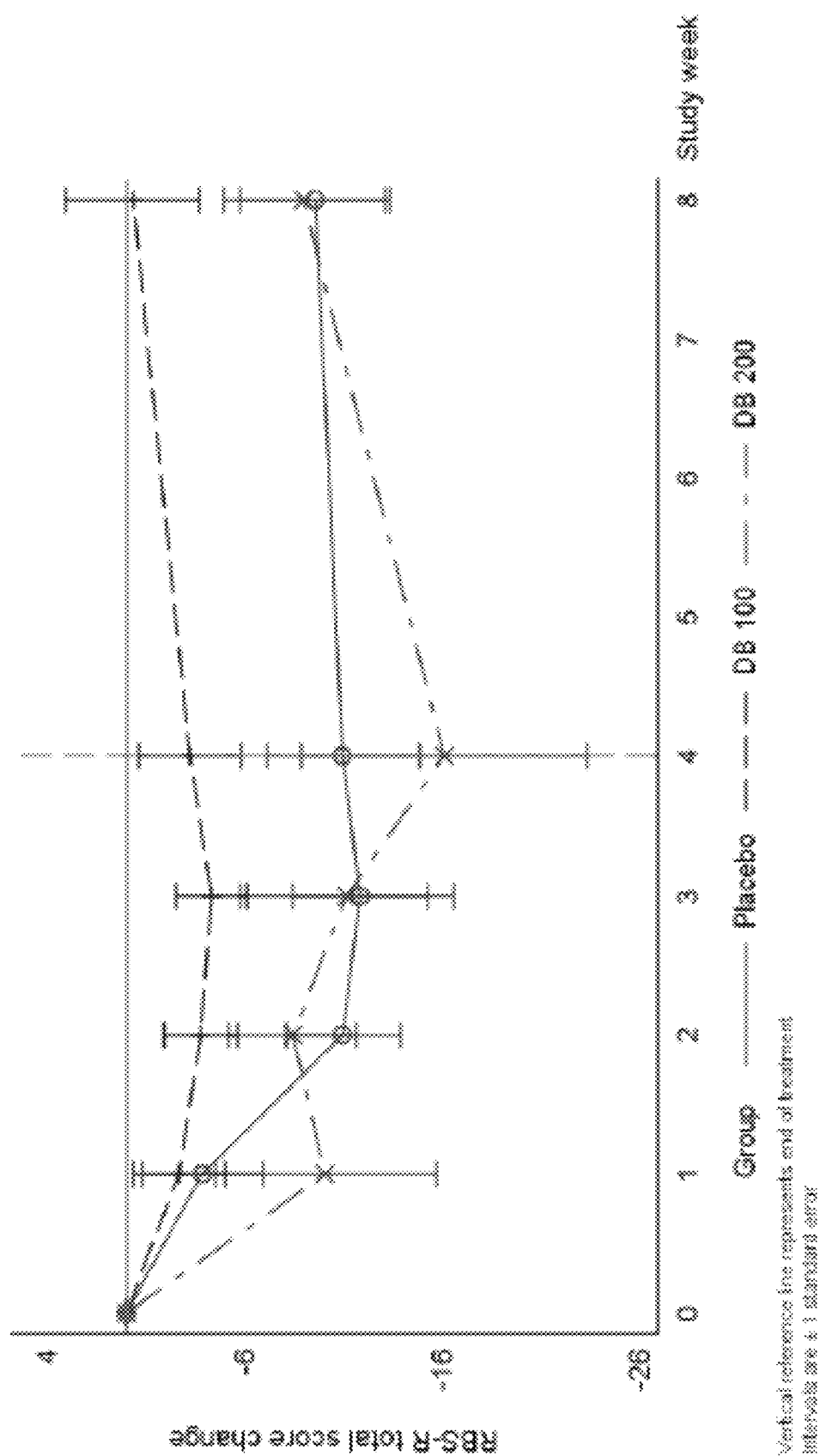
FIG. 40 shows the change from Baseline in RBS-R Total Score, Week 0-Week 8 (ITT Population, Draft).
Figure 41:
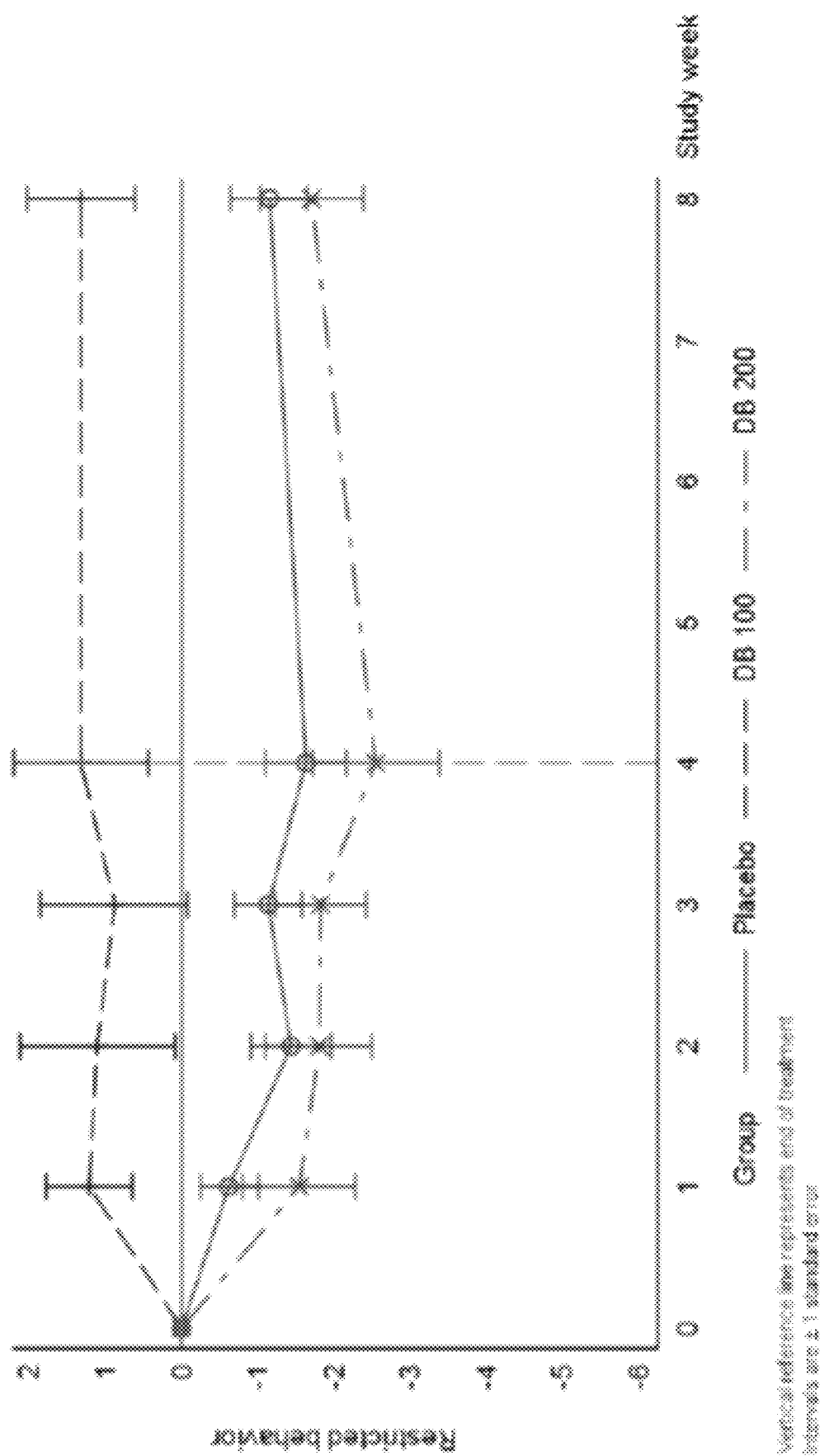
FIG. 41 shows the change from Baseline in RBS-R Restrictive Behavior, Week 0-Week 8 (ITT Population, Draft). There were mean improvements in RBS-R Total Score as noted by a decrease in score for L1-79 200 mg compared to placebo.
Figure 42:
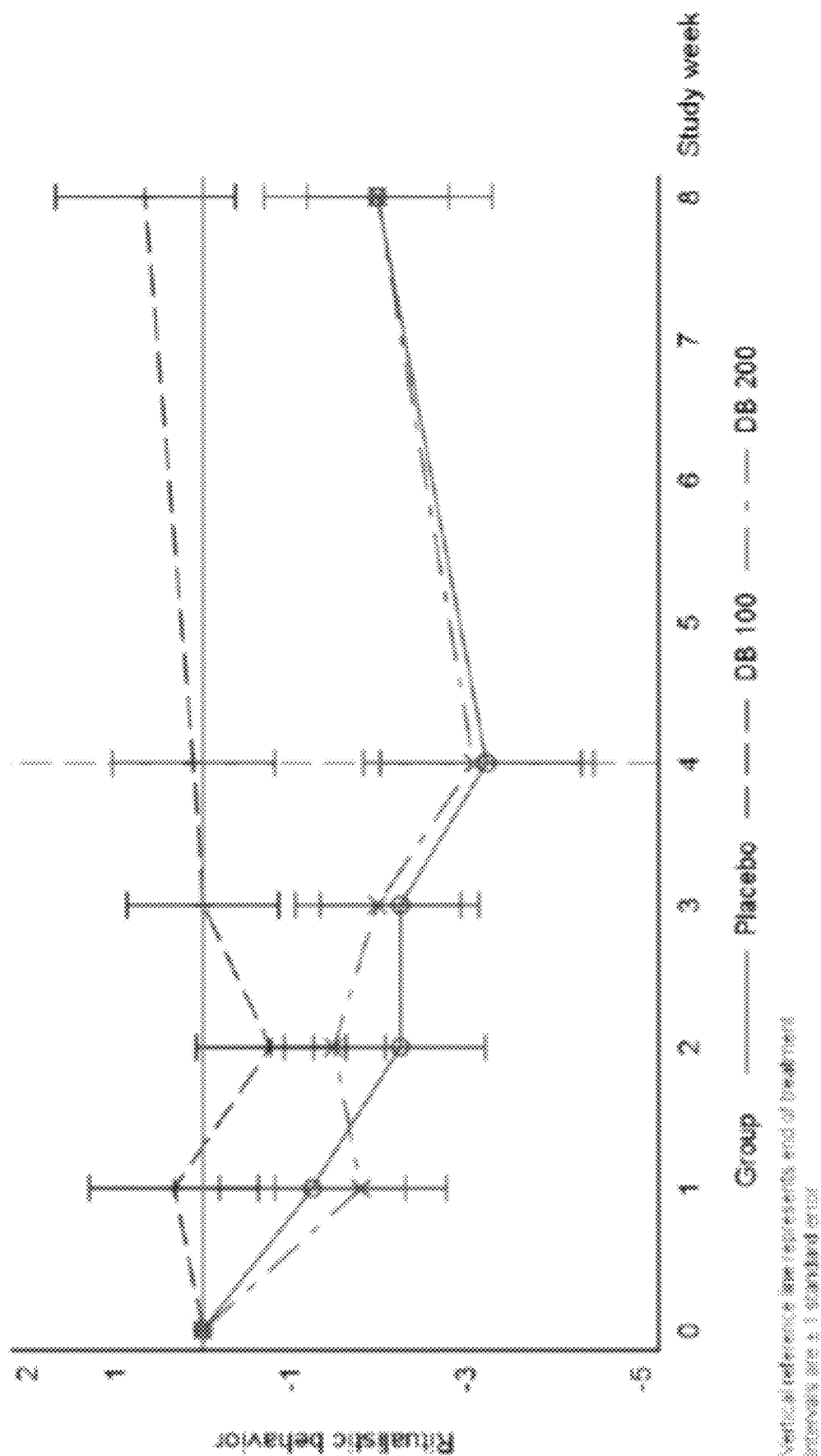
FIG. 42 shows the change from Baseline in RBS-R Ritualistic Behavior, Week 0-Week 8 (ITT Population, Draft).
Figure 43:
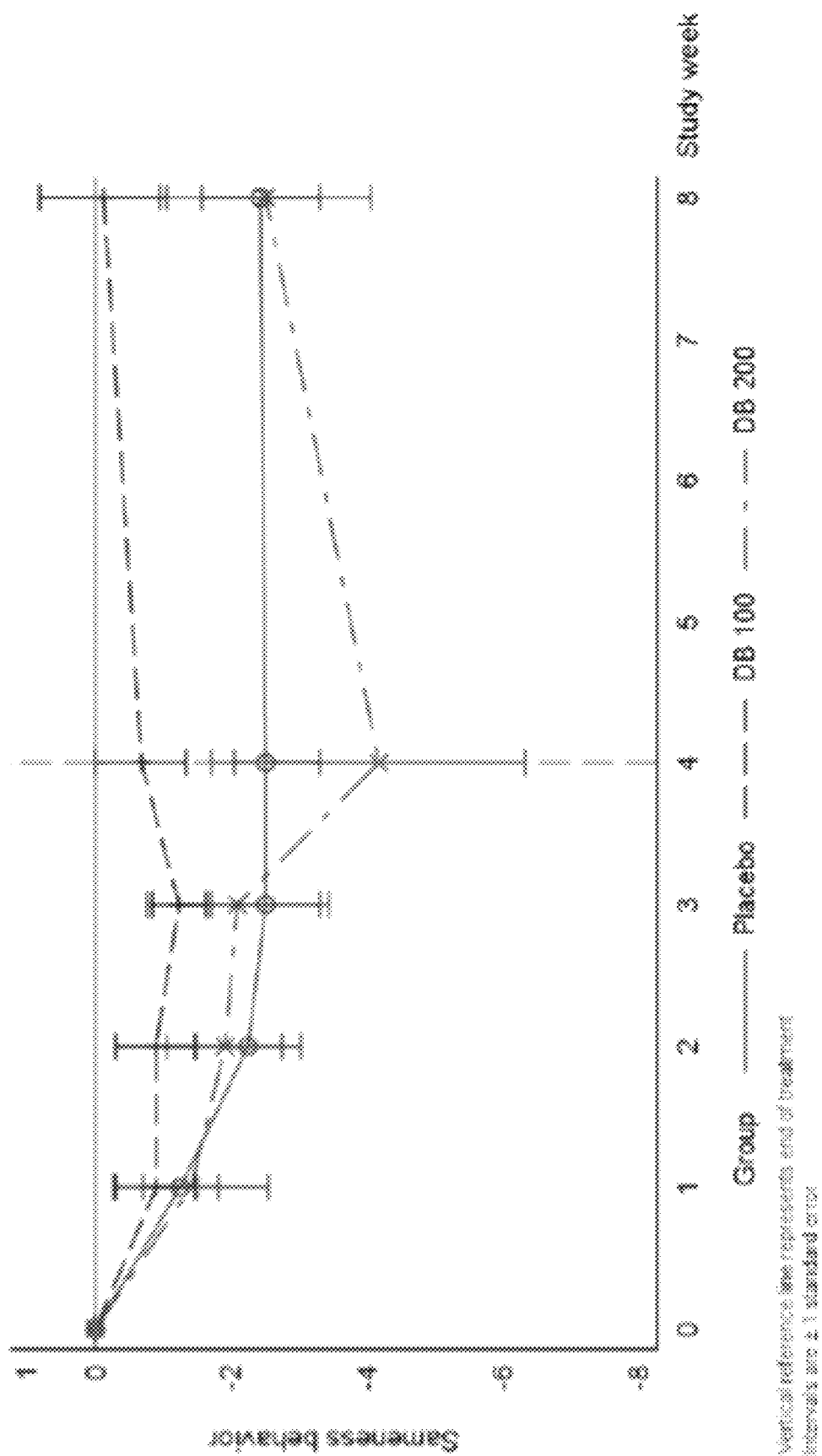
FIG. 43 shows the change from Baseline in RBS-R Sameness Behavior, Week 0-Week 8 (ITT Population, Draft).
Figure 44:
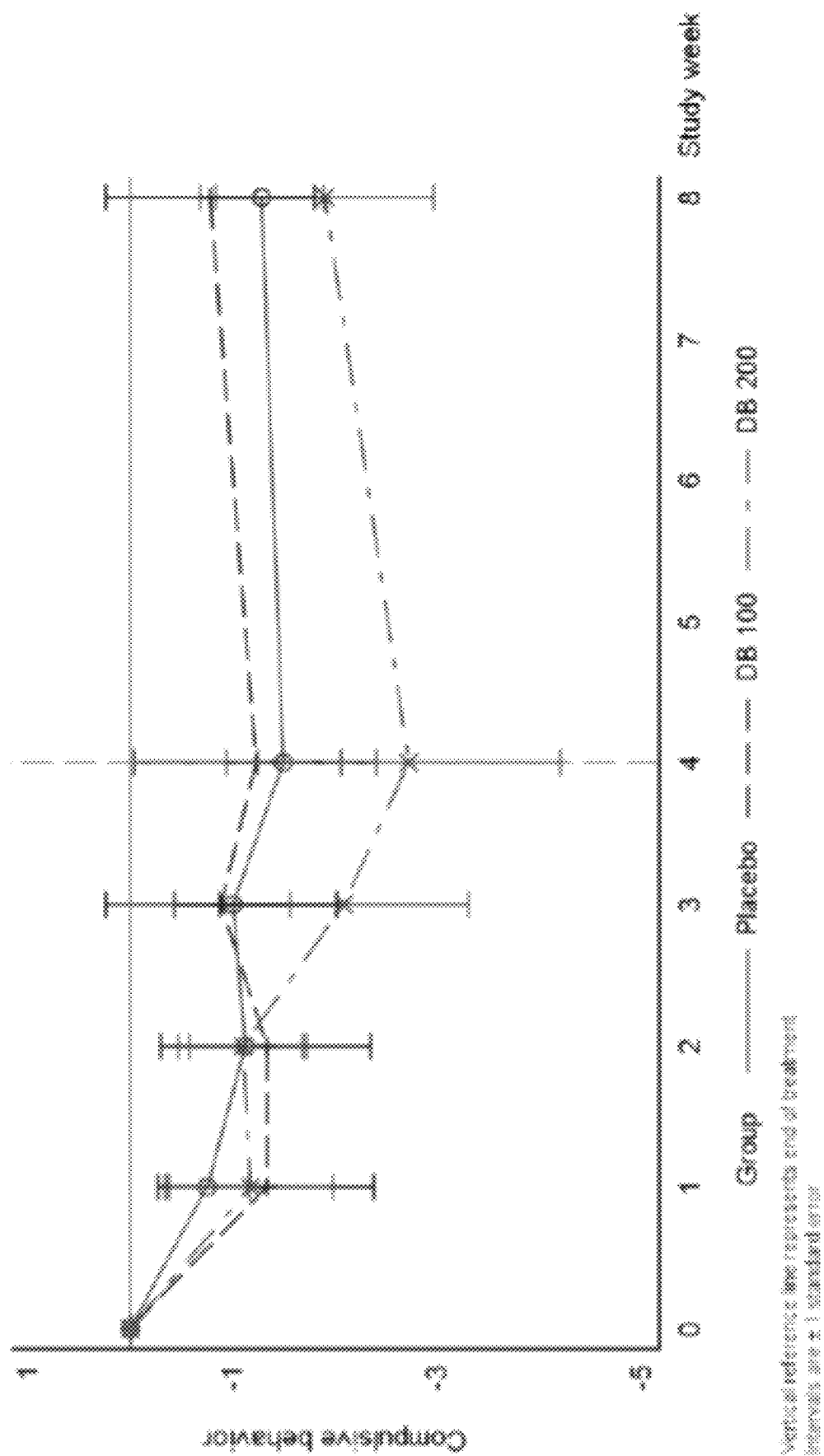
FIG. 44 shows the change from Baseline in RBS-R Compulsive Behavior, Week 0-Week 8 (ITT Population, Draft).
Figure 45:
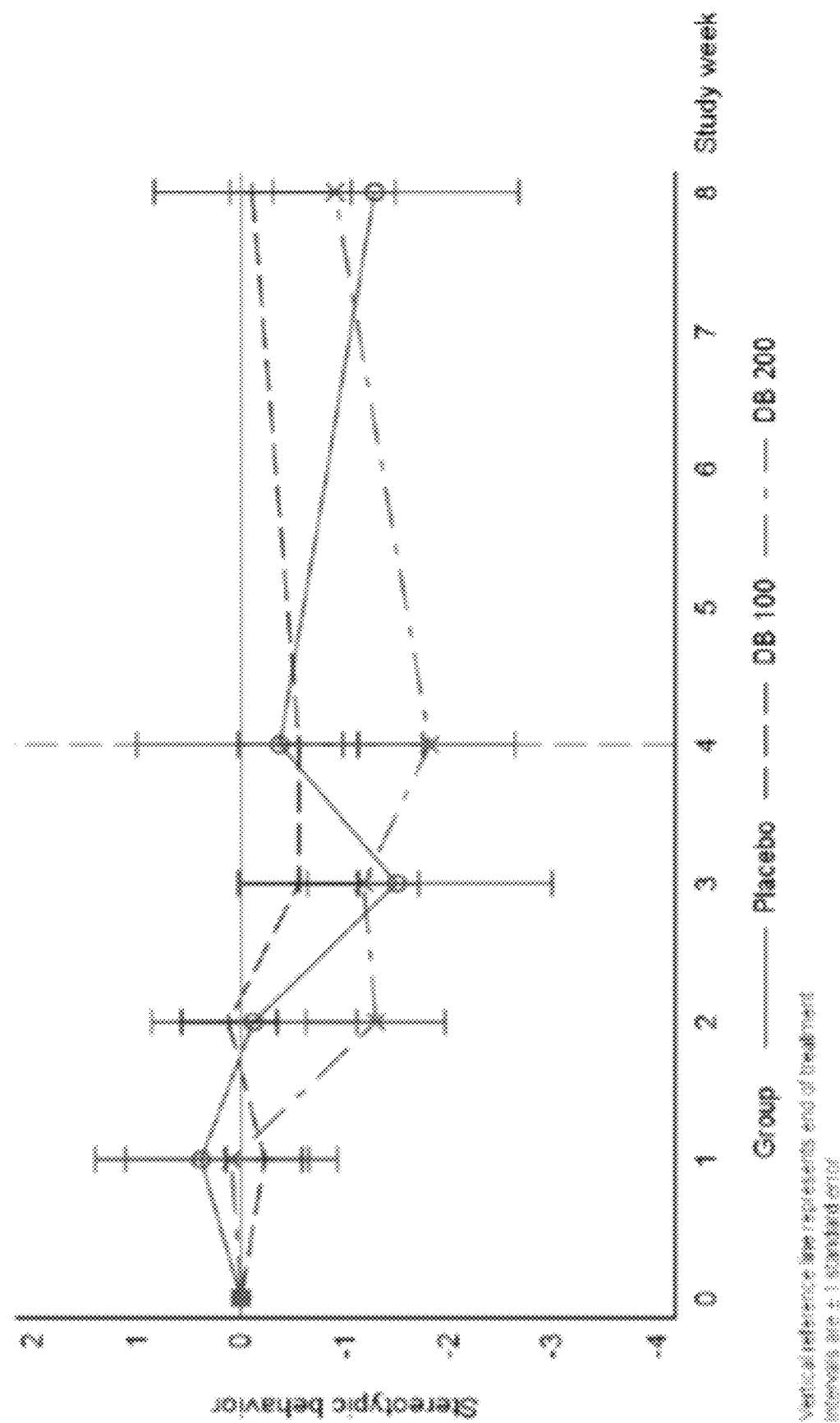
FIG. 45 shows the change from Baseline in RBS-R Stereotypic Behavior, Week 0-Week 8 (ITT Population, Draft).
Figure 46:
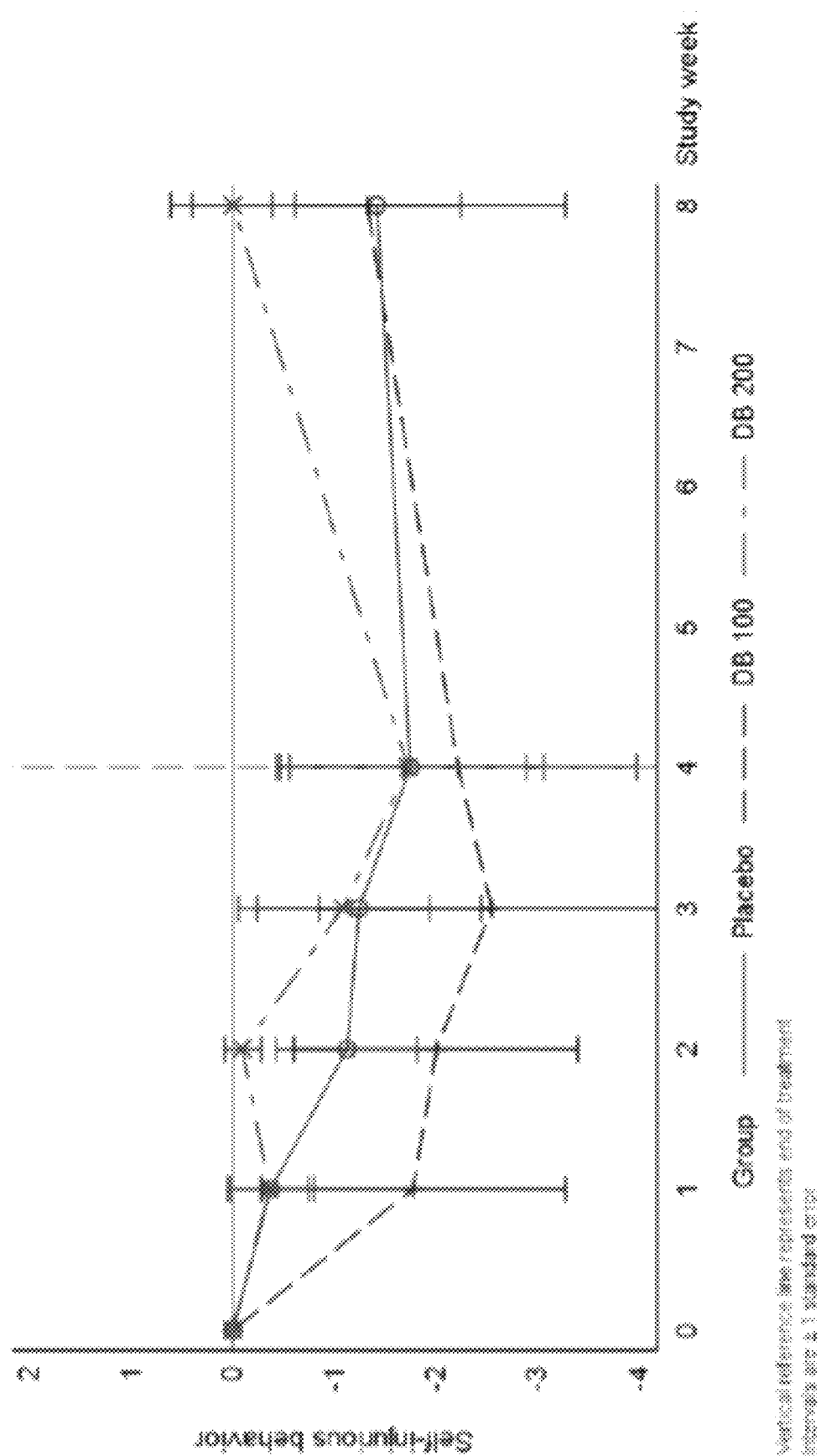
FIG. 46 shows the change from Baseline in RBS-R Self-injurious Behavior, Week 0-Week 8 (ITT Population, Draft).

There were mean improvements in RBS-R Total Score as noted by a decrease in score for L1-79 200 mg compared to placebo. (FIG. 40).

Figure 47:
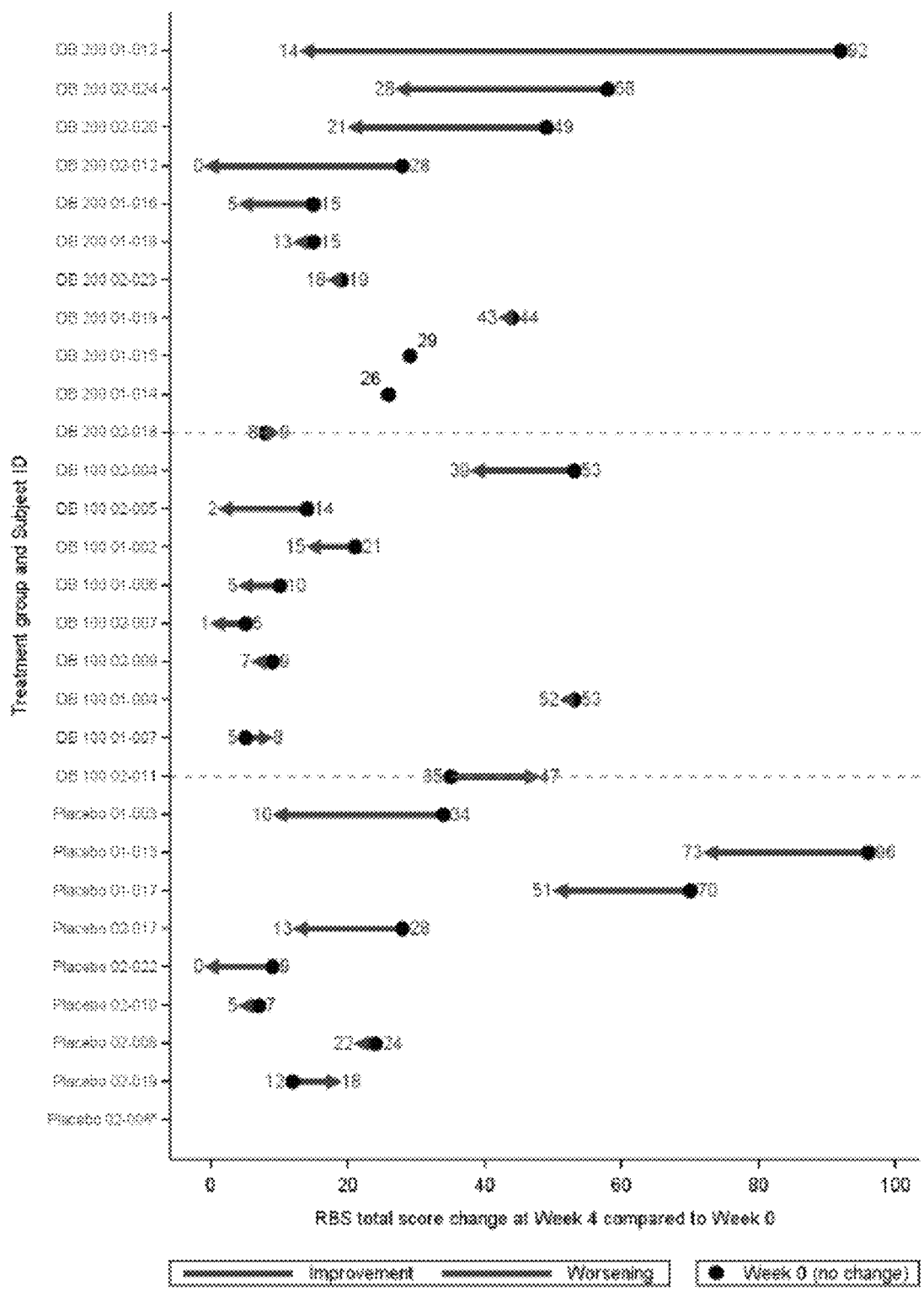
FIG. 47 shows the change in RBS-R Total Score from Baseline to Week 4 by Patient (ITT Population, Draft)
Figure 48:
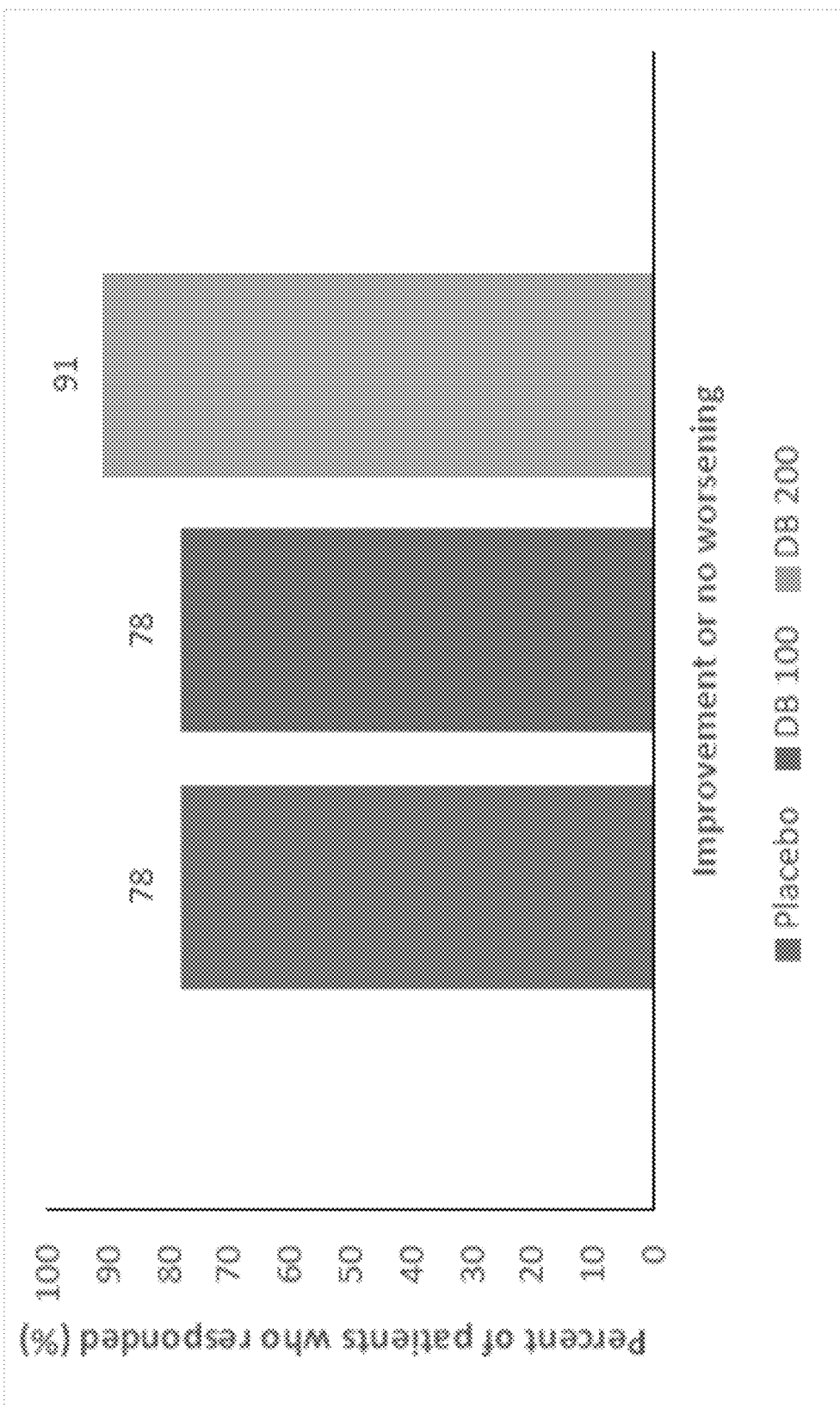
FIG. 48 shows the responder analyses (defined as an improvement or no worsening) for RBS-R Total Score at Week 4 or LOCF.

A summary of the change in RBS-R Total Score from Baseline to Week 4 is displayed by patient in FIG. 47. In addition, responder analyses (defined as an improvement or no worsening) are presented for RBS-R Total Score at Week 4 or LOCF in FIG. 48.

Consistent with the ABC-C Lethargy and Social Withdrawal and ABC-C Inappropriate Speech Domains, the RBS-R Total Score demonstrated a clear trend toward a greater magnitude of reduction in restricted and repetitive behaviors with L1-79 200 mg compared to placebo. This is further demonstrated by the responder analysis, which shows that 91% of patients treated with L1-79 200 mg had improvement or stabilization of symptoms compared to 78% with placebo.

Overall Conclusions

Currently available therapies for children and adults with ASD only target collateral symptoms associated with the disorder (irritability, agitation, impulsivity, hyperactivity) and have side effects that require monitoring metabolic parameters through blood tests. While phlebotomy is unpleasant for most neurotypical children and adults, it is quite traumatic for those with extreme sensory sensitivities who are unable to adequately communicate their fears. Indeed, it is a catch-22 for these individuals, in that many of the aberrant behaviors they exhibit are likely due to an inability to interact, communicate and connect with others. The potential to provide them with a therapy that not only improves upon the core symptoms responsible for those behaviors, but to do so without the need for invasive monitoring will go a long way to improve the quality of life for these children.

Results from Study HT 02-121 provide proof of concept that L1-79 appears to provide benefit in treating the core symptoms of ASD. ASD is defined primarily as persistent deficits in social communication and social interaction as well as restricted and repetitive behavior patterns, interests or activities. Preliminary evidence from multiple independent assessments specifically used to measure both the social and behavioral intensity of these core symptoms demonstrated consistent trends that were repeatable across multiple instruments. While the limited size and short duration of the study precluded any expectation or ability to demonstrate statistically significant improvements in the outcome measures used, the agreement between the multiple measures utilized in this study is very encouraging. In less than one month of treatment, the blinded assessment by the clinicians involved in the study demonstrated a nearly one-point change in the CGI-S compared to baseline. Similarly, patients receiving L1-79 improved by nearly one point from baseline in ADOS-2 scores within the same time period.

Previous experience (see Example 5) with open-label administration of L1-79 in 10 patients with autism clearly demonstrated that L1-79 has the potential to improve the core symptoms of autism. In Study HT 02-121, multiple independent efficacy measures including the CGI-S, ADOS-2, SRS-2, ABC-C and RBS-R demonstrated consistent improvements in the target score social domains affected by ASD despite the short treatment period and small number of patients. Over the 28-day treatment period, L1-79 was safe and well tolerated. At the conclusion of the study, many parents wanted their children to continue receiving treatment with L1-79. As a result, a roundtable videos were filmed at both clinical sites with the intent of allowing these parents to speak directly with FDA about the impact of L1-79 on their children with autism.

Example 7

A Randomized, Double-Blind, Placebo-Controlled Adaptive Trial of L1-79 for the Treatment of the Core Deficits in Social-Communication Function and Adolescents and Adults with Autism Spectrum Disorder The completed Study HT 02-121 (Example 6) was a Phase II safety study of L1-79 for the treatment of autism. Study HT 02-121 was a randomized double-blind, placebo-controlled two-cohort, 4-week dose-escalation study that incorporated 2 open-label treatment groups to assess the safety and efficacy of L1-79 100 mg and 200 mg TID in male patients between the ages of 13 and 21 years of age with autism. Results from Study HT 02-121 provide proof of concept that L1-79 appears to provide benefit in treating the core symptoms of ASD. Preliminary evidence from multiple independent assessments specifically used to measure both the social and behavioral intensity of these core symptoms demonstrated consistent trends that were repeatable across multiple instruments. While the limited size and short duration of the study precluded any expectation or ability to demonstrate statistically significant improvements in the outcome measures used, the agreement between the multiple measures utilized in this study is very encouraging. Following a review of the results from Study HT 02-121 the FDA allowed L1-79 to begin registration trials leading toward a marketing approval and awarded the L1-79 IND 128673 a Fast Track designation.

As a result, the inventors are proposing an adaptive trial approach in a Phase III setting that will allow an expedient yet thorough approach to evaluating L1-79 as a therapy for treating the defining core deficits in social communication and interaction. Based on the results from Study HT 02-121 (Example 6), proposed are two Phase III randomized, double-blind, parallel group, placebo controlled, clinical studies (Study 301 and Study 302) utilizing adaptive designs in order to evaluate optimal inclusion criteria, sample size and outcome measures during the first segment of Study 301 to quantify the safety and efficacy of L1-79 administered TID at doses of 200 or 300 mg to subjects with a diagnosis of autism based upon their Autism Diagnostic Observation Schedule-2 (ADOS-2) results in a prospectively randomized and double-blind manner.

Most of the clinical experience with L1-79 for the treatment of autism is with doses of 100-200 mg TID. The study of Example 8 (also referred to herein as "Study 301") seeks to quantify the safety and efficacy of L1-79 administered TID at doses of 200 or 300 mg to subjects with a diagnosis of autism based upon their Autism Diagnostic Observation Schedule-2 (ADOS-2) results in a prospectively randomized and double-blind manner.

The dosage form is a capsule containing 100 mg of DL-α-methyl-para-tyrosine capsules (hereafter referred to as "L1-79"). The intended dosing regimen of L1-79 for Phase III clinical studies (Study 301 and Study 302) is 2 or 3 capsules administered orally three times daily (TID).

Rationale for Study Design:

ASD is a disorder marked by deficits in social interaction and the presence of restricted, repetitive patterns of behavior, interests, or activities during childhood development (Swedo, S. E., Baird, G., Cook, E. H., Happe', F. G., Harris, J. C., Kaufmann, W. E., . . . Wright, Harry, H. (Eds.). (2013). Neurodevelopmental Disorders. In *American Psychiatric Association. Diagnostic and statistical manual of mental disorders* (5th ed.). American Psychiatric Association.). Recent literature has implicated peripheral and autonomic nervous system involvement in children and adults with ASD (Baker, 2017; Fenning, 2017). As a result, electrodermal skin testing may serve as an important biomarker for the population of patients more likely to respond to treatments targeting the sympathetic nervous system.

Primary Objective(s):

The primary objectives of the study are to evaluate the efficacy, safety, and tolerability of L1-79 compared to placebo for the treatment of the core deficits in social communication and interaction in adolescents and adults with autism spectrum disorder (ASD).

Secondary Objective(s):

Secondary objectives of the study include the following:
1. to evaluate optimal inclusion criteria, sample size, and outcome measures during the first segment of this adaptive trial;
2. to evaluate the effect of L1-79 compared to placebo on reducing repetitive and restrictive behaviors in ASD;
3. to evaluate the effect of L1-79 compared to placebo on reducing aberrant behaviors in ASD, including hyperactivity, agitation, and irritability; and
4. to perform additional modeling of pharmacokinetics (PK) and pharmacodynamics (PD) for L1-79 in a subset of subjects through timed intermittent sparse sampling.

Study Design:

Eligible participants will be adolescents and adults between the ages of 12 and 21 years who meet the Diagnostic and Statistical Manual of Mental Disorders-5th edition (DSM-5) criteria for ASD, based upon clinician interview and assessment of ASD symptoms on the ADOS-2, and a Clinical Global Impression of Severity (CGI-S) rating of 4 or greater (moderate or higher).

Subjects will be randomized to placebo, L1-79 200 mg, or L1-79 300 mg three times daily (TID) groups in a 1:2:2 ratio.

Subjects in the 200 and 300 mg group will be started on 200 mg TID. Subjects in the 300 mg group will titrate up to 300 mg TID after 7 days.

Screening assessments will include the ADOS-2, a review of ASD criteria from the DSM-5 and the CGI-S.

An adaptive design will be used with a proposed interim analysis being used to make decisions on the following criteria; potential endpoints for the primary outcome, modification of the defined study population, and estimated sample size. The data monitoring committee and independent statistical group will implement the interim analysis and make recommendations to the sponsor regarding proposed changes in the study based on predefined criteria. The sample size recalculation will depend on the primary outcome and potential study populations that will be determined at the interim analysis. The sample size recalculation will be based on blinded data.

A schedule of events is provided in Table 30.

TABLE 30

Schedule of Events

| Evaluation | Screening Days −30 to −1 | Visit 1 Day 0 | Treatment Period | | | | Follow-up |
| | | | Visit 2 Day 14 ± 3 | Visit 3 Day 28 ± 3 | Visit 4 Day 60 ± 3 | Visit 5 Day 84 ± 3 | Visit 6 Day 120 ± 3 |
|---|---|---|---|---|---|---|---|
| Informed Context | X | | | | | | |
| Inclusion/Exclusion Criteria | X | | | | | | |
| Demographics | X | | | | | | |
| Medical History[1] | X | X | | | | | |
| Physical Examination | X[2,3] | X[4] | | | | | X[2] |
| Vital Signs[3] | X | X | X | X | X | X | X |
| Urine Drug Screen[6] | X | X | | | | | |
| Pregnancy Test[7] | X | X | | | | | |
| Pharmacokinetics (PK) - 1 hr post dose | | X | | | | | |
| PK - Random (known time after dose) | | | | X[8] | X[8] | X | |
| Laboratory Tests[9] | X | | | | X | | X |
| Randomization | | X | | | | | |

TABLE 30-continued

Schedule of Events

| | | | | Treatment Period | | | Follow-up |
|---|---|---|---|---|---|---|---|
| Evaluation | Screening Days −30 to −1 | Visit 1 Day 0 | Visit 2 Day 14 = 3 | Visit 3 Day 28 = 3 | Visit 4 Day 60 = 3 | Visit 5 Day 84 = 3 | Visit 6 Day 120 = 3 |
| 12-Lead ECG | X | | | X | | X | X |
| Drug Administration | | X | X | X | X | | |
| Drug Accountability | | | X | X | X | X | |
| Adverse Event (AE) Assessment | | X | X | X | X | X | X |
| Prior/Concomitant Medication Assessment | X | X | X | X | X | X | X |
| ADOS-2[10] | X | | | | | X | |
| CGI-S | X | X | | | | X | X |
| CGI-C | | | | X | X | X | X |
| VABS-3[11] | | X | | X | X | X | X |
| SRS-2 | | X | | X | X | X | X |
| ABC-C | | X | | X | X | X | X |
| RBS-R | | X | | X | X | X | X |
| PSI | | X | | | | X | X |
| SSP | | X | | | | X | |
| WASI-2 | | X | | | | | |
| DSM-5 criteria for ASD | X | | | | | | |
| Skin Reactivity Testing (SRT) | | X | | | | X | X |

ABC-C = Aberrant Behavior Checklist-Community;
ADOS-2 = Autism Diagnostic Observation Scale-2;
ASD = autism spectrum disorder;
CGI-C = Clinical Global Impression of Change;
CGI-S = Clinical Global Impression of Severity;
DSM-5 = Diagnostic and Statistical Manual of Mental Disorders-5th edition;
PSI = Parenting Stress Index;
RBS-R = Repetitive Behavior Scale-Revised;
SAS = Spence Anxiety Scale;
SSP = Spence Anxiety Scale;
SRS-2 = Social Responsiveness Scale-2;
VABS-3 = Vineland Adaptive Behavior Scales - 3rd Edition;
WASI-2 - Weschler Abbreviated Scales of Intelligence
[1]Includes a review of previous/ongoing medications
[2]Complete examination, including assessments of the skin, head, eyes, ears, nose, throat, neck, thyroid, lungs, heart, abdomen, lymph nodes, extremities, and body weight
[3]Height will be measured at screening only.
[4]Partial examination, to update findings from the examination performed at screening
[5]Includes respiratory rate, oral temperature, sitting and standing orthostatic blood pressure and pulse
[6]Includes amphetamines, barbiturates, cocaine metabolites, opiates, benzodiazepines, cannabinoids, and cotinine
[7]Only for females who are post-menarche
[8]Subject will only have random PK done for one of Visits 2, 3, or 4.
[9]Includes serum chemistry, hematology (including coagulation), and urinalysis
[10]ADOS-2 Will be videotaped for potential use as an additional review for Reciprocal Social Interaction by Blinded reviewer
[11]Adaptive Behavior Composite domains only Inclusion Criteria:
1. Subjects must be male or female adolescents or adults up to age 21
2. Subjects must be between the ages of 13 and 21 years of age
3. Post menarche females must be on birth control if appropriate.
4. Diagnosis of ASD based upon an assessment tool that utilizes the DSM-5 criteria [e.g., Autism Symptom Rating Scale (ASRS), Childhood Autism Rating Scale-2 (CARS2), or Autism Diagnostic Interview-Revised (ADI-R)], and confirmed with the ADOS-2, with a CGI-S score of 4 or greater.
5. Subject must be stable on no more than one concomitant medication, and no planned changes in psychosocial interventions during the trial
6. Subjects and caregiver must be willing and able to participate in the testing procedures sufficient to obtain valid scores on the tests used herein.
7. Subjects must have a caregiver who has known the them for over a year, spends at least 10 hours per week with them, and is willing to accompany them to each appointment.
8. Subjects must, in the opinion of the Investigator, be sufficiently tolerant and capable of complying with the requirements of this trial. For example, patients who will not tolerate blood draws or ECG are not qualified candidates for this study.
9. Subjects must be able to swallow capsules
10. Subjects and their care givers must be willing to sign informed consent or to have informed consent provided by their legal guardians or proxies. All subjects <18 years old or those unable to care for themselves must have the caregiver's consent.

Exclusion Criteria:
1. Sexually active males and females
2. Uncontrolled intercurrent illness including, but not limited to, ongoing or active infection, symptomatic cardiovascular disease, hepatic disease, renal disease, skeletomuscular disease, HIV, HCVA, HBV, or psychiatric illness/social situations that would limit compliance with study requirements.
3. Any disease that requires treatment with immunosuppressive drugs
4. A diagnosis of Fragile-X syndrome, Rett syndrome, or other neurological disorder that could be the basis for the subjects autistic symptoms (e.g., congenital or acquired brain injury, brain malformations, stroke, neurogenetic or metabolic disorder).

5. A DSM-5 diagnosis of schizophrenia, schizoaffective disorder, alcohol use disorder or ADHD, Current or lifetime diagnosis of severe psychiatric disorder (e.g., bipolar disorder, etc.);
6. The Presence of any active chronic medical problem including, but not limited to uncontrolled seizure disorder, heart disease, cancer, asthma, genetic disease, or any disease or syndrome that requires continuous drug therapy.
7. Subjects requiring more than 1 medication for the treatment of autism, or who have not been weaned to their lowest tolerable dose of medication.
8. Subjects with any disease that requires treatment with immunosuppressive drugs.
9. The presences of out of range hepatic or renal function tests or other unexplained abnormal laboratory value that is deemed clinically significant by the Investigator.
10. Any subject or caregiver who is unwilling or unable to give informed consent.

Study Population:
  350 patients are planned.

Test Product, Dose, and Mode of Administration:
  D-L alpha-methyl-tyrosine (L1-79) encapsulated as 100 and 200 mg. Two dose arms will be tested as 200 mg TID (one 200 mg dose combined with placebo) and 300 mg TID (one 200 mg capsule and one 100 mg capsule)

Duration of Treatment:
  12 weeks (84 days)

Efficacy Assessments:
  Baseline assessments not included in the measurement of efficacy include the Weschler Abbreviated Scales of Intelligence (WASI-2) and the Spence Anxiety Scale (SAS). Electrodermal testing will be performed at baseline to determine if greater autonomic nervous system variability correlates with response to treatment. (See Study Rationale). The primary outcome measure will be the change from baseline at Week 12 on a 5-factor composite measure comprising the Socialization (SOC), Communication (COM), and Daily Living Skills (DLS) domains from the Adaptive Behavior Composite (ABC) of the Vineland Adaptive Behavior Scales—3rd Edition (VABS-3) and the Socialization, Communication and Interaction (SCI) and Restricted Interests and Repetitive Behavior (RRB) subscales of the Social Responsiveness Scale-2 (SRS-2). The primary secondary outcome measure will be based on the change from baseline CGI-S at Week 12.

Additional secondary outcome measures will be assessed in a gated fashion (to be determined during the interim analysis) for the change from baseline scores at Week 12 for:
1. Aberrant Behavior Checklist-Community (ABC-C) Social Withdrawal/Lethargy and Inappropriate Speech Domains
2. ABC-C, Irritability, Hyperactivity, and Stereotypy Domains
3. Repetitive Behavior Scale-Revised (RBS-R)
4. Parenting Stress Index (PSI) Short Form
5. Sensory Profile-Short Form (SSP)
6. Spence Anxiety Scale (SAS)
7. ADOS-2 Total Score* (ADOS-2 will be videotaped at screening and at end of study for potential use in blinded review of reciprocal interaction.)

Safety Assessments:
  Safety assessments include physical examination, orthostatic measurements of blood pressure and pulse, standard hematology and clinical chemistry assessments, concomitant medication use, urinalysis, ECGs, and spontaneously reported adverse events.

PK Assessments:
  In order to gain a greater understanding of the PK and PD of L1-79 in patients with ASD, sparse sampling will be utilized to assist in modeling PK parameters and comparing the same to data obtained from more thorough studies done in young healthy adults. Sparse sampling will limit the number of phlebotomy procedures, an important consideration in children with ASD who are typically much more traumatized by blood drawing procedures than peers without ASD.

Statistical Methods:
  The adaptive design will assess three components of the study; the outcome variable, a potential modification of the inclusion criteria, and a sample size recalculation based on the decisions made at the time of the interim analysis. The modification of the inclusion criteria will be based on an evaluation of potential endophenotypes for ASD of baseline severity of the following characteristics known to directly influence treatment and intervention strategies for people with ASD: 1) Severity of anxiety based on assessment by the Spence Anxiety Scale, IQ as assessed by the Weschler Abbreviated Scale of Intelligence and disruptive behavior symptom severity, based on the ABC-C irritability and hyperactivity subscales. In addition, skin reactivity testing to determine autonomic sensitivity will be used as an exploratory biomarker for responder phenotype (See Study Rationale for justification for these subgroups). The choice of primary outcome(s) will be based on a conditional power analysis of the 5-factor composite measure comprising the Socialization (SOC), Communication (COM), and Daily Living Skills (DLS) domains from the Adaptive Behavior Composite (ABC) of the Vineland Adaptive Behavior Scales—3rd Edition (VABS-3) and the Socialization, Communication and Interaction (SCI) and Restricted Interests and Repetitive Behavior (RRB) subscales of the Social Responsiveness Scale-2 (SRS-2). After selection of the outcomes and inclusion criteria, the sample size will be recalculated based on blinded data.

It will be appreciated by those skilled in the art that changes could be made to the embodiments described above without departing from the broad inventive concept thereof. It is understood, therefore, that this invention is not limited to the particular embodiments disclosed, but it is intended to cover modifications that are within the spirit and scope of the invention, as defined by the appended claims.

What is claimed is:
1. A method for treating an autism in a subject in need thereof, the method comprising administering to said subject a composition comprising a therapeutically effective amount of α-methyl-DL-tyrosine, and a pharmaceutically acceptable carrier.
2. The method of claim 1, wherein the composition comprises α-methyl-DL-tyrosine in an amount ranging from about 50 mg (w/w) to about 1000 mg (w/w).
3. The method of claim 1, wherein the composition comprises α-methyl-DL-tyrosine in an amount of about 100 mg (w/w/).
4. The method of claim 1, wherein the composition comprises α-methyl-DL-tyrosine in an amount of about 200 mg (w/w/).
5. The method of claim 1, wherein the composition comprises α-methyl-DL-tyrosine in an amount of about 250 mg (w/w/).
6. The method of claim 1, wherein the composition comprises α-methyl-DL-tyrosine in an amount of about 300 mg (w/w/).
7. The method of claim 1, wherein the composition is administered in a plurality of divided doses.

8. The method of claim 1, wherein the composition is administered in a plurality of divided doses.

9. The method of claim 1, wherein the composition is administered as a single sustained release daily dose.

10. The method of claim 1, wherein the composition is administered as a chewable dosage form for pediatric patients.

11. The method of claim 1, wherein the composition is administered two times per day.

12. The method of claim 1, wherein the composition is administered three times per day.

13. The method of claim 1, further comprising administering to said subject a therapeutically effective amount of a central nervous system (CNS) agent.

14. The method of claim 13, wherein said agent is Y-aminobutyric acid (GABA).

15. The method of claim 13, wherein said agent is beta-adrenergic agonist.

16. The method of claim 1, wherein the composition is administered orally.

17. The method of claim 16, wherein the composition is in a form of a capsule or a tablet.

18. The method of claim 1, wherein said subject is a human patient between 3 years of age and 21 years of age.

19. The method of claim 1, wherein said subject is an adult human patient.

* * * * *